US012129502B2

(12) United States Patent
Alphandery

(10) Patent No.: US 12,129,502 B2
(45) Date of Patent: Oct. 29, 2024

(54) METHOD FOR REMOVING IMPURITIES FROM NANOPARTICLES

(71) Applicant: NANOBACTERIE, Paris (FR)

(72) Inventor: Edouard Alphandery, Paris (FR)

(73) Assignee: NANOBACTERIE, Paris (FR)

( * ) Notice: Subject to any disclaimer, the term of this patent is extended or adjusted under 35 U.S.C. 154(b) by 1222 days.

(21) Appl. No.: 16/589,394

(22) Filed: Oct. 1, 2019

(65) Prior Publication Data

US 2020/0102229 A1 Apr. 2, 2020

(30) Foreign Application Priority Data

Oct. 2, 2018 (FR) ....................................... 1801033
Oct. 2, 2018 (FR) ....................................... 1801034

(51) Int. Cl.

| | |
|---|---|
| ***C12P 3/00*** | (2006.01) |
| ***B82Y 35/00*** | (2011.01) |
| ***B82Y 40/00*** | (2011.01) |
| ***C01G 49/08*** | (2006.01) |
| ***C12N 1/20*** | (2006.01) |
| ***C12N 1/38*** | (2006.01) |

(52) U.S. Cl.

CPC ................ *C12P 3/00* (2013.01); *C01G 49/08* (2013.01); *C12N 1/20* (2013.01); *C12N 1/38* (2013.01); *B82Y 35/00* (2013.01); *B82Y 40/00* (2013.01); *C01P 2004/64* (2013.01)

(58) Field of Classification Search

CPC ........... B82Y 40/00; B82Y 35/00; B82Y 5/00; C12P 3/00; C01G 49/08; C01G 49/06; C01G 49/02; C12N 1/20; C12N 1/38; C01P 2004/64; C01P 2002/88; C01P 2004/61; C01P 2004/62; C01P 2006/80; A61K 33/26; A61K 9/14; A61K 9/50

See application file for complete search history.

(56) References Cited

FOREIGN PATENT DOCUMENTS

| | | | |
|---|---|---|---|
| CN | 101372364 | A | 2/2009 |
| EP | 2666456 | A1 | 11/2013 |
| FR | 2974815 | A1 | 11/2012 |
| WO | WO 00/46867 | * | 8/2000 |

OTHER PUBLICATIONS

Bharde et al (Bacterial Aerobic Synthesis of Nanocrystalline Magnetite, JACS, 2005) (Year: 2005).*

(Continued)

*Primary Examiner* — Colin W. Slifka
*Assistant Examiner* — Logan Edward Laclair
(74) *Attorney, Agent, or Firm* — Maier & Maier, PLLC

(57) ABSTRACT

A method for removing at least one impurity from metal-based nanoparticles, including at least two heating steps. During step 1, the temperature of the nanoparticles is increased to a temperature $T_1$, and is then maintained at $T_1$ during a heating time that is included between 1 second and 20 years, where $T_1$ is included between 50° C. and 300° C. During step 2, the temperature of the nanoparticles is increased to a temperature $T_2$, and is then maintained at $T_2$ during a heating time that is included between 1 second and 20 years, where $T_2$ is included between 300° C. and 600° C.

14 Claims, 5 Drawing Sheets

(56) References Cited

OTHER PUBLICATIONS

Search Report issued on Aug. 23, 2019 in corresponding application No. FR1801033, 14 pgs.
Search Report issued on Jul. 26, 2019 in corresponding application No. FR1801034, 25 pgs.
Matthew J. O'Hara et al: "Magnetic iron oxide and manganese-doped iron oxide nanoparticles for the collection of alpha-emitting radionuclides from aqueous solutions", RSC Advances, vol. 6, No. 107, (Jan. 1, 2016), pp. 105239-105251, 13 pgs.
Cynthia L. Warner et al: "Manganese Doping of Magnetic Iron Oxide Nanoparticles: Tailoring Surface Reactivity for a Regenerable Heavy Metal Sorbent", LANGMUIR, vol. 28, No. 8, (Feb. 13, 2012), pp. 3931-3937, 7 pgs.
Scott J. Kemp et al: "Monodisperse magnetite nanoparticles with nearly ideal saturation magnetization", RSC Advances, vol. 6, No. 81, (Aug. 8, 2016), pp. 77452-77464, 13 pgs.
Panchal Vineet et al: "Control ling magnetic properties of iron oxide nanoparticles using post-synthesis thermal treatment", Applied Physics a Materials Science & Processing, Springer Berlin Heidelberg, Berlin/Heidelberg, vol. 114, No. 2, (Feb. 12, 2013), pp. 537-544, 9 pgs.
Zhang Z J et al: Magnetic greigite (Fe3S4) nanomaterials: Shape-controlled solvothermal synthesis and their calcination conversion into hematite (α-Fe2O3) nanomaterials, Journal of Alloys and Compounds, Elsevier Sequoia, Lausanne, CH, vol. 488, No. 1, (Nov. 20, 2009), pp. 339-345, 7 pgs.
Edouard Alphandery: "Applications of Magnetosomes Synthesized by Magnetotactic Bacteria in Medicine", Frontiers in Bioengineering and Biotechnology, vol. 2, (Mar. 11, 2014), 6 pgs.
Matsunaga T et al: "Enhancement of Magnetic Particle Production By Nitrate and Succinate Fed-Batch Culture of *Magnetospirillum* Sp. AMB-1", Biotechnology Techniques, Chapman & Hall, vol. 10, No. 5, (Jan. 1, 1996), pp. 485-500, 6 pgs.
U. Heyen et al: "Growth and magnetosome formation by microaerophilic Magnetospirillum strains in anoxygen-controlled fermentor", Applied Microbiology and Biotechnology, vol. 61, No. 5-6, (Feb. 20, 2003), pp. 536-544, 9 pgs.
Jian-Bo Sun et al: "High-yield growth and magnetosome formation by Magnetospirillum gryphiswaldense MSR-1 in an oxygen-controlled fermenter supplied solely with air", Applied Microbiology and Biotechnology, Springer, Berlin, DE, vol. 79, No. 3, (Apr. 19, 2008) , pp. 389-397, 9 pgs.
Yang Chen-Dong et al: "Effects of growth medium composition, iron sources and atmospheric oxygen concentrations on production of luciferase-bacterial magnetic particle complex by a recombinantMagnetospirillum magneticumAMB-1", Enzyme and Microbial Technology, Stoneham, MA, US, vol. 29, No. 1, (Apr. 23, 2017) , pp. 13-19, 7 pgs.
Edouard Alphandéry et al: "Chains of Magnetosomes Extracted from AMB-1 Magnetotactic Bacteria for Application in Alternative Magnetic Field Cancer Therapy", HAL archives-ouvertes.fr, (Jun. 30, 2017), pp. 1-16, 18 pgs.
Jacob Jobin John et al: "Magnetotactic bacteria and magnetosomes—Scope and challenges", Materials Science and Engineering C, Elsevier Science S.A, CH, vol. 68, (Jul. 20, 2016), pp. 919-928, 10 pgs.
Dirk Schuler et al: "Iron-limited growth and kinetics of iron uptake in Magnetospirillum gryphiswaldense", Archives of Microbio, Springer Berlin Heidelberg, Berlin/Heidelberg, vol. 166, No. 5, (Nov. 1, 1996), pp. 301-307, 7 pgs.
Sarah Staniland et al., "Controlled cobalt doping of magnetosomes in vivo", Nature Nanotechnology, V. 3, p. 158 (2008), 5 pgs.
Search Report issued on Feb. 24, 2020 in corresponding European Application No. 19020544.3; 13 pages.
Search Report issued on Mar. 2, 2020 in corresponding European Application No. 19020545.0; 20 pages.
Araujo et al., "Magnetotactic Bacteria as Potential Sources of Bioproducts", Marine Drugs, vol. 13, No. 1, Jan. 16, 2015, pp. 389-430.
Ali et al., "Yield cultivation of magnetotactic bacteria and magnetosomes: A review", Journal of Basic Microbiology, vol. 57, No. 8, May 2, 2017, pp. 643-652.
Bazylinski et al., "*Magnetovibrio blakemorei* gen. nov., sp nov., a magnetotactic bacterium (Alphaproteobacteria: Rhodospirillaceae) isolated from a salt marsh", International Journal of Systematic and Evolutionary Microbiology, vol. 63, No. Pt 5, Sep. 14, 2012, pp. 1824-1833.
Bazylinski et al., "Supplementary Methods. Collection, enrichment and isolation of strain MV-1", Jan. 1, 2012, pp. 1-5.
Xiang et al., "Purified and sterilized magnetosomes from Magnetospirillum gryphiswaldense MSR-1 were not toxic to mouse fibroblasts in vitro", Letters in Applied Microbiology, vol. 45, No. 1, Jul. 1, 2007, pp. 75-81.
Faivre et al., "Magnetotactic Bacteria and Magnetosomes", Chemical Reviews, vol. 108, No. 11, Nov. 12, 2008, pp. 4875-4898.

* cited by examiner

METHOD FOR REMOVING IMPURITIES FROM NANOPARTICLES

FIELD

The field of the invention is that of methods for purifying nanoparticles.

BACKGROUND

Nanoparticles often comprise impurities, such as toxic Cobalt, (S. Staniland et al, Nature Nanotechnology, V. 3, P. 158 (2008)), which should be avoided according to regulation. It therefore appears necessary to develop new methods to remove these impurities such as that presented in this invention.

SUMMARY

The invention relates to a method for removing at least one impurity from metal-based nanoparticles, comprising at least two heating steps in which:

- during a step 1, the temperature of the nanoparticles is increased to a temperature $T_1$, and is then maintained at $T_1$ during a heating time that is comprised between 1 second and 20 years, where $T_1$ is comprised between 150° C. and 300° C., and
- during a step 2, the temperature of the nanoparticles is increased to a temperature $T_2$, and is then maintained at $T_2$ during a heating time that is comprised between 1 second and 20 years, where $T_2$ is comprised between 300° C. and 600° C.

The invention also relates to a method for removing at least one impurity from metal-based nanoparticles, comprising at least two heating steps in which or during which:

- During a step 1, the temperature of the nanoparticles is increased to a temperature $T_1$, and is then maintained at $T_1$ during a heating time that is comprised between 1 second and 20 years, where $T_1$ is comprised between 150° C. and 250° C.
- During a step 2, the temperature of the nanoparticles is increased to a temperature $T_2$, and is then maintained at $T_2$ during a heating time that is comprised between 1 second and 20 years, where $T_2$ is comprised between 350° C. and 45° C.

The invention also relates to the method according to the invention, comprising an additional step between steps 1 and 2, preferentially designated as step 3, in which the temperature of the nanoparticles in increased to a temperature $T_3$ and is then maintained at $T_3$ during a heating time that is comprised between 1 second and 20 years, where $T_3$ is comprised between 250° C. and 350° C. The invention also relates to a method for removing at least one impurity from metal-based nanoparticles, comprising at least one heating step, preferentially chosen among step(s) 1, 2, and/or 3.

DETAILED DESCRIPTION

Figure 1:
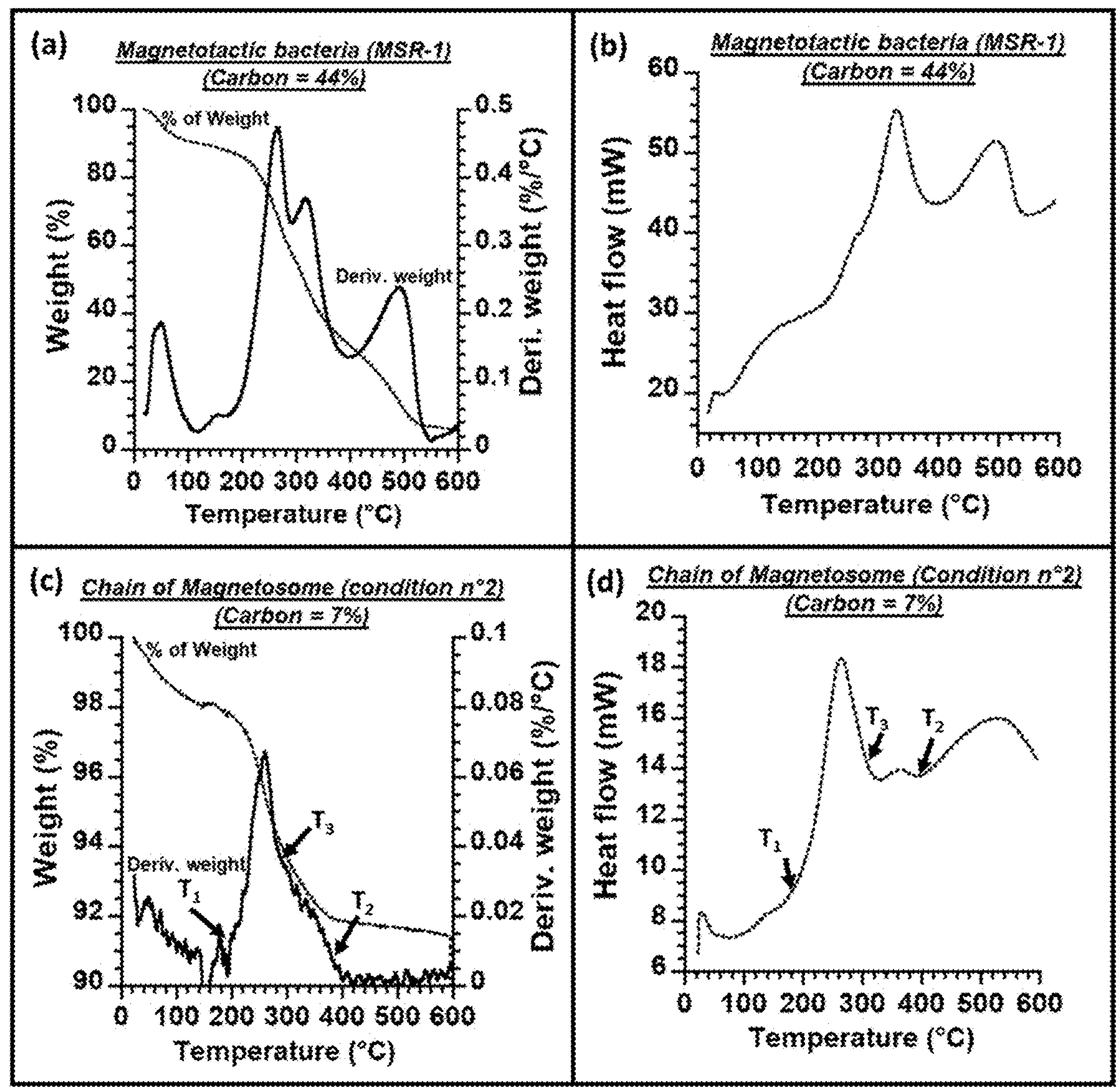
FIG. 1: TGA-DSC analysis of whole magnetotactic bacteria and magnetosomes extracted from magnetotactic bacteria according to condition 2 of lysis. (a) The variation of the percentage in weight as a function of temperature as well as the derivative of this variation as a function of temperature for a sample comprising 3 mg of lyophilized magnetotactic bacteria when it is heated between 20° C. and 600° C. at a rate of 6° C./min. (b) Heat flow in mW as a function of temperature produced by a sample comprising 3 mg of lyophilized magnetotactic bacteria when it is heated between 20° C. and 600° C. at a rate of 6° C./min (c) The variation of the percentage in weight as a function of temperature as well as the derivative of this variation as a function of temperature for a sample comprising 3 mg of lyophilized magnetosomes extracted from whole bacteria according to condition 2 of lysis when the sample is heated between 20° C. and 600° C. at a rate of 6° C./min. (d) Heat flow in mW as a function of temperature produced by a sample comprising 3 mg of lyophilized magnetosomes extracted from whole bacteria according to condition 2 of lysis when the sample is heated between 20° C. and 600° C. at a rate of 6° C./min. Concerning (a) and (c), the y axis can be replaced by the percentage in mass, leading to the same plots.

In one embodiment of the invention, the temperature of the nanoparticles is maintained at the temperature $T_1$, $T_2$, and/or $T_3$, during a heating time that is smaller than 100 years, 50 years, 20 years, 10 years, 5 years, 2 years, 1 year, 11 months, 6 months, 3 months, 2 month, 1 month, 3 weeks, 2 weeks, 1 week, 6 days, 5 days, 3 days, 1 day, 23 hours, 12 hours, 6 hours, 1 hour, 50 minutes, 30 minutes, 20 minutes, 10 minutes, 5 minutes, 2 minutes, 1 minute, 50 seconds, 30 seconds, 10 seconds, 1 seconds, 1 millisecond or 1 microsecond.

In another embodiment of the invention, the temperature of the nanoparticles is maintained at the temperature $T_1$, $T_2$, and/or $T_3$, during a heating time that is larger than 1 microsecond, 1 millisecond, 1 second, 10 seconds, 30 seconds, 50 seconds, 1 minute, 2 minutes, 5 minutes, 10 minutes, 1 hour, 6 hours, 12 hours, 23 hours, 1 day, 3 days, 5 days, 6 days, 1 week, 2 weeks, 3 weeks, 1 month, 2 months, 3 months, 6 months, 11 months, 1 year, 2 years, 5 years, 10 years, 20 years, 50 years or 100 years.

In still another embodiment of the invention, the temperature of the nanoparticles is maintained at the temperature $T_1$, $T_2$, and/or $T_3$, during a heating time that is comprised between 1 microsecond and 100 years, 1 second and 20 years, 1 second and 1 year, 1 second and 1 month, 1 second and 1 day, 1 minute and 1 day, 5 minutes and 1 day, 10 minutes and 12 hours, 30 minutes and 6 hours or between 30 minutes and 3 hours.

In an embodiment of the invention, the heating time is larger than the time during which the temperature is increased to $T_1$, $T_2$, and/or $T_3$, preferentially by a factor of more than 1.001, 1.1, 1.5, 2, 5, 10, $10^3$, $10^5$ or $10^{10}$.

In an embodiment of the invention, $T_1$ is comprised between −273° C. and 250° C., −200° C. and 250° C., −100 and 250° C., 50 and 250° C., 50 and 250° C., 150 and 250° C., or between 180 and 220° C.

In an embodiment of the invention, $T_2$ is comprised between 200 and $10^5$, 250 and $10^5$, 300 and $10^5$, 350 and $10^5$, 350 and $10^3$, 350 and 500, 350 and 450, or between 360 and 400° C.

In some cases, $T_3$ is comprised between −273 and $10^5$, −200 and $10^3$, −100 and 500, −50 and 200, 0 and 500, 100 and 500, 200 and 500, 200 and 400, or between 250 and 350° C.

In still another embodiment of the invention, $T_3$ is comprised between $T_1$ and $T_2$. In some cases, $T_3$ is lower than $T_2$, preferentially by a factor of more than 1.0001, 1.1, 1.2, 1.5, 2, 5, 10, $10^3$ or $10^5$. In some other cases, $T_3$ is larger than $T_1$, preferentially by a factor of more than 1.0001, 1.1, 1.2, 1.5, 2, 5, 10, $10^3$ or $10^5$.

In one embodiment of the invention, the temperature of the nanoparticles is the temperature of the heating apparatus or furnace used to heat the nanoparticles and/or comprising the nanoparticles, preferentially before, during, or after the treatment of the nanoparticles by the method.

In one embodiment of the invention, the method comprises at least two heating steps designated as step 1 or heating step 1 and step 2 or heating step 2.

In one embodiment of the invention, $[T_1, T_2]$ is the temperature interval in which: i) the variation or loss as a function of temperature of the weight or mass of the nanoparticles is the largest, or ii) the derivative of the variation or loss as a function of temperature of the weight or mass of the nanoparticles is the largest.

In one embodiment of the invention, the ratio $[\% W(T_2)-\% W(T_1)]/(T_2-T_1)$, where $\% W(T_2)$ and $\% W(T_1)$ are the percentages in weight of the nanoparticles at $T_2$ and $T_1$, respectively, is larger than $10^{-50}$, $10^{-30}$, $10^{-20}$, $10^{-10}$, $10^{-5}$, 0.01, 0.02, 0.03, 0.05, 0.1, 0.2, 0.3, 0.5, 1, 10 or $10^5$%/° C. In some cases, this ratio is large when the percentage in mass of carbon in the nanoparticles, preferentially before treating the nanoparticles by or with the method, is large, preferentially larger than $10^{-20}$, $10^{-10}$, $10^{-5}$, $10^{-2}$, $10^{-1}$, 1, 5, 10, 20, 50, 75, 85, 95 or 100%/° C.

In another embodiment of the invention, the ratio $[\% W(T_2)-\% W(T_1)]/(T_2-T_1)$ is lower than $10^{50}$, $10^{30}$, $10^{20}$, $10^{10}$, $10^5$, 10, 5, 2, 1, 0.5, 0.05, $10^{-3}$, $10^{-5}$, $10^{-10}$ or $10^{-20}$%/° C. In some cases, this ratio is low when the percentage in mass of carbon in the nanoparticles, preferentially before treating the nanoparticles by or with the method, is low, preferentially lower than 100, 95, 80, 70, 50, 30, 20, 10, 5, 2, 1, $10^{-1}$, $10^{-3}$, $10^{-5}$, $10^{-10}$ or $10^{-20}$%/° C.

In another embodiment of the invention, the ratio $[\% W(T_2)-\% W(T_1)]/(T_2-T_1)$ is larger than the ratio $[\% W(T_1)-\% W(T_{<T1})]/(T_1-T_{<T1})$, in some cases preferentially by a factor of more than 1.00001, 1.001, 1.01, 1.1, 1.2, 1.5, 2, 5, 10, $10^3$, $10^5$ or $10^{10}$, in some other cases preferentially by a factor of less than $10^{10}$, $10^5$, $10^3$, 10, 5, 2, 1.5, 1.2, 1.1, 1.01, 1.001 or 1.00001, where $\% W(T_{<T1})$ is the percentages in weight of the nanoparticles at $T_{<T1}$ and $T_{<T1}$ is a temperature smaller than $T_1$, in some cases preferentially by a factor of more than 1.00001, 1.001, 1.01, 1.1, 1.2, 1.5, 2, 5, 10, $10^3$, $10^5$ or $10^{10}$, in some other cases preferentially by a factor of less than $10^{10}$, $10^5$, $10^3$, 10, 5, 2, 1.5, 1.2, 1.1, 1.01, 1.001 or 1.00001. In some cases, this situation occurs when the variation in weight of the nanoparticles is larger between $T_1$ and $T_2$ than between $T<T_1$ and $T_1$. In some cases, $T_{<T1}$ is not sufficient or is too small to remove a significant amount of organic, carbon or carbonaceous material from the nanoparticles.

In another embodiment of the invention, the ratio $[\% W(T_2)-\% W(T_1)]/(T_2-T_1)$ is larger than the ratio $[\% W(T_{>T2})-\% W(T_2)]/(T_{>T2}-T_2)$, in some cases preferentially by a factor of more than 1.00001, 1.001, 1.01, 1.1, 1.2, 1.5, 2, 5, 10, $10^3$, $10^5$ or $10^{10}$, in some other cases preferentially by a factor of less than $10^{10}$, $10^5$, $10^3$, 10, 5, 2, 1.5, 1.2, 1.1, 1.01, 1.001 or 1.00001, where $\% W(T_{>T2})$ is the percentages in weight of the nanoparticles at $T_{22\ T2}$ and $T_{>T2}$ is a temperature larger than $T_2$, in some cases preferentially by a factor of more than 1.00001, 1.001, 1.01, 1.1, 1.2, 1.5, 2, 5, 10, $10^3$, $10^5$ or $10^{10}$, in some other cases preferentially by a factor of less than $10^{10}$, $10^5$, $10^3$, 10, 5, 2, 1.5, 1.2, 1.1, 1.01, 1.001 or 1.00001. In some cases, this situation occurs when the variation in weight of the nanoparticles is larger between $T_1$ and $T_2$ than between $T_2$ and $T_{>T2}$. In some cases, $T_{>T2}$ is too large to remove a significant amount of organic, carbon or carbonaceous material from the nanoparticles. In some other cases, $T_{>T2}$ has crystallized the organic, carbon or carbonaceous of the nanoparticles, preferentially preventing its removal from the nanoparticles. In still some other cases, $T_{>T2}$ has destroyed the nanoparticles.

In one embodiment of the invention, $T_1$ is larger than $T_{<T1}$ and/or $T_2$ is lower than $T_{>T2}$.

In one embodiment of the invention, the temperature of the nanoparticles is maintained at a given temperature $T_i$, when the temperature of the nanoparticles varies by less than $10^5$, $10^3$, 90, 80, 70, 60, 50, 40, 30, 20, 10, 5, 3, 2, 1, $10^{-5}$, $10^{-10}$ or $10^{-20}$%. In some cases, this percentage is equal to $T_{imax}-T_{imin}/T_{iav}$, where $T_{imax}$, $T_{imin}$, and $T_{iav}$ are the maximum, minimum, and average temperatures reached during the heating time or during the heating step, preferentially after the temperature is maintained at a temperature $T_i$, which is preferentially $T_1$, $T_2$, and/or $T_3$. In some cases, this percentage is low when the furnace or heating apparatus enables to maintain the temperature stable without large fluctuations and/or when the nanoparticles are not prone to endothermic and/or exothermic reactions. In some cases, the endothermic reaction is a reaction in which heat or energy is transferred from the medium surrounding the nanoparticles to the nanoparticles. In some other cases, the exothermic reaction is a reaction in which heat or energy is transferred from the nanoparticles to the medium surrounding the nanoparticles.

In one embodiment of the invention, the temperature of the nanoparticles is not maintained at a given temperature $T_i$, when the temperature of the nanoparticles varies by more than $10^5$, $10^3$, 90, 80, 70, 60, 50, 40, 30, 20, 10, 5, 3, 2, 1, $10^{-5}$, $10^{-10}$ or $10^{-20}$%. In some cases, this percentage is large when the furnace or heating apparatus does not enable to maintain the temperature stable without large fluctuations and/or when the nanoparticles are prone to endothermic and/or exothermic reactions.

In one embodiment of the invention, the method according to the invention comprises an additional step (step 3) of heating the nanoparticles at a temperature $T_3$, which is preferentially comprised between $T_1$ and $T_2$. In some cases, $T_3$ is lower than $T_2$, in some cases preferentially by more than 0.001, 0.1, 1, 5, 10, 50, 100 or $10^3$° C., in some other cases preferentially by a factor of less than $10^3$, 100, 50, 10, 5, 2, 1, 0.1 or 0.001° C. In some other cases, $T_3$ is larger than $T_1$, in some cases preferentially by more than 0.001, 0.1, 1, 5, 10, 50, 100 or $10^3$° C., in some other cases preferentially by less than $10^3$, 100, 50, 10, 5, 2, 1, 0.1 or 0.001° C.

The invention relates to a method for removing at least one impurity from metal-based nanoparticles, comprising at least two heating steps during which:

During step 1, the temperature of the nanoparticles is preferentially increased up to a temperature $T_1$ and is maintained at this temperature, comprised between 190° C. and 210° C., during a heating time comprised between 5 min and 24 hours.

During an optional step, which is between step 1 and step 2, the temperature of the nanoparticles is preferentially increased up to a temperature $T_3$ and is maintained at this temperature, comprised between 290 and 310° C., during a heating time, comprised between 5 min and 24 hours.

During step 2, the temperature of the nanoparticles is preferentially increased up to a temperature $T_2$ and is maintained at this temperature, comprised between 370 and 400° C., during a heating time, comprised between 5 min and 24 hours.

In one embodiment of the invention, the method according to the invention is a method of removal of impurities from nanoparticles or of purification of nanoparticles or of treatment of nanoparticles.

In some cases, the method according to the invention can be preceded by steps of: i) extraction or isolation of nanoparticles from a medium or from cells, ii) fabrication of nanoparticles, iii) contamination of nanoparticles by impurity(ies), carbon, carbonaceous material, parts or whole cells, living organisms, endotoxins, lipopolysaccharide, or iv) capture or attraction of impurity(ies) by nanoparticle(s).

In on embodiment of the invention, the metal-based nanoparticle(s) are designated as (the) nanoparticle(s). In some cases, the nanoparticle(s) can designate the nanoparticle(s) before treatment by the method according to the invention. In some other cases, the nanoparticle(s) can designate the nanoparticle(s) during the treatment by the method. In still some other cases, the nanoparticle(s) can designate the nanoparticle(s) after treatment by the method according to the invention.

In one embodiment of the invention, the nanoparticle(s) comprise(s) or is/are assemblies of more than 1, 2, 5, 10, $10^3$, $10^5$, $10^{10}$, $10^{20}$, $10^{50}$ or $10^{100}$ nanoparticle(s).

In another embodiment of the invention, the nanoparticle(s) comprise(s) or is/are assemblies of less than $10^{100}$, $10^{50}$, $10^{20}$, $10^{10}$, $10^5$, $10^3$, 100, 50, 10, 5 or 2 nanoparticle(s).

In one embodiment of the invention, the metal-based nanoparticles comprise at least one metal or one metallic chemical element, preferentially selected from the group consisting of: Actinium, Aluminium, Americium, Barium, Berkelium, Beryllium, Bismuth, Bohrium, Cadmium, Calcium, Californium, Cerium, Cesium, Chromium, Cobalt, Copper, Curium, Darmstadtium, Dubnium, Dysprosium, Einsteinium, Erbium, Europium, Fermium, Francium, Gadolinium, Gallium, Gold, Hafnium, Hassium, Holmium, Indium, Iridium, Iron, Lanthanum, Lawrencium, Lead, Lithium, Lutetium, Magnesium, Manganese, Meitnerium, Mendelevium, Mercury, Molybdenum, Neodymium, Neptunium, Nickel, Niobium, Nobelium, Osmium, Palladium, Platinum, Plutonium, Polonium, Potassium, Praseodymium, Promethium, Protactinium, Radium, Rhenium, Rhodium, Roentgenium, Rubidium, Ruthenium, Rutherfordium, Samarium, Scandium, Seaborgium, Silver, Sodium, Strontium, Tantalum, Technetium, Terbium, Thallium, Thorium, Thulium, Tin, Titanium, Tungsten, Ununbium, Ununhexium, Ununpentium, Ununquadium, Ununtrium, Uranium, Vanadium, Ytterbium, Yttrium, Zinc, and Zirconium.

In another embodiment of the invention, the metal-based nanoparticles comprise or consist of metal oxide(s), preferentially of chemical formula $M_\alpha O_\beta$, where M is a metallic chemical element, O is oxygen, and $\alpha$, $\beta$ are coefficients, preferentially stoichiometric coefficients. In some cases, $\alpha$ and/or $\beta$ is/are equal to 0, 1, 2, 3, 4, 5, 6, 7, 8, 9, 10, 11, 12, 13, 14, 15, 16, 18, 19, or 20. In some other cases, $\alpha$ and/or $\beta$ is/are larger than 0, 1, 2, 3, 4, 5, 6, 7, 8, 9, 10, 11, 12, 13, 14, 15, 16, 18, 19, 20, $10^2$, $10^3$ or $10^{10}$. In still some other $\alpha$ and/or $\beta$ is/are lower than $10^{10}$, $10^3$, $10^2$, 20, 19, 18, 17, 16, 15, 14, 13, 12, 11, 10, 9, 8, 7, 6, 5, 4, 3, 2, 1 or 0.

In one embodiment of the invention, the nanoparticles comprise a predominant chemical element, which is the metal or metal oxide. In some cases, it can be designated as nanoparticle predominant chemical element. Its presence or percentage, preferentially in mass, which is preferentially the quantity, preferentially the mass, of this chemical element per quantity, preferentially the mass, of nanoparticle, can be larger than 10, 50, 75, 90 or 99%.

In one embodiment of the invention, the impurity is the impurity of or comprised in the nanoparticle. In some cases, it can be designated as nanoparticle impurity. Its presence or percentage, preferentially in mass, can be estimated as a quantity, preferentially mass, of this impurity, per quantity, preferentially mass, of the nanoparticle.

In one embodiment of the invention, the nanoparticle(s) also comprise a doping material.

In an embodiment of the invention, the impurity differs from the doping material or at least one property of the impurity differs from at least one property of the doping material. For example, the presence of the doping material in the nanoparticles can increase or decrease the coercivity, remanent magnetization, saturating magnetization of the nanoparticles, preferentially by a factor of more than 1.0001, 1.1, 1.2, 1.5, 5, 10, $10^3$ or $10^6$, compared with un-doped nanoparticles, whereas the presence of impurity(ies) in the nanoparticles does not change the coercivity, remanent magnetization, saturating magnetization of the nanoparticles, preferentially by a factor of more than 1.0001, 1.1, 1.2, 1.5, 5, 10, $10^3$ or $10^6$, of the nanoparticles.

In an embodiment of the invention, the impurity is the same as the doping material or the impurity has at least one property in common with the doping material.

In one embodiment of the invention, the impurity is or comprises a chemical element different from the predominant chemical element and/or doping material.

The invention also relates to the method according to the invention, wherein the nanoparticle(s) comprise(s): i) the predominant chemical element, ii) the predominant chemical element and the impurity, iii) the predominant chemical element and the doping material, or iv) the predominant chemical element and the impurity and the doping material.

In one embodiment of the invention, the nanoparticle(s) does/do not comprise at least one impurity or comprise(s) less than $10^{50}$, $10^{20}$, $10^{10}$, $10^5$, $10^3$, 1, $10^{-1}$, $10^{-3}$, $10^{-5}$, $10^{-10}$, $10^{-20}$, or $10^{-50}$ impurity(ies) or impurities per gram of nanoparticles or gram of impurities per gram of nanoparticles. The nanoparticles preferentially comprise a low concentration of impurity following their treatment by the method.

In one embodiment of the invention, the nanoparticle(s) does/do not comprise at least one impurity or comprise(s) more than $10^{-50}$, $10^{-20}$, $10^{-10}$, $10^{-5}$, $10^{-3}$, 1, 2, 5, 10, $10^3$, $10^5$, $10^{10}$, $10^{20}$, or $10^{50}$ impurity(ies) or impurities per gram of nanoparticles or gram of impurities per gram of nanoparticles.

In one embodiment of the invention, the nanoparticle(s) comprise(s) a lower quantity of impurities, preferentially by a factor larger than 0.001, 0.01, 0.1, 1, 10, 100, $10^3$, $10^5$, $10^{10}$, $10^{20}$ or $10^{50}$, after than before the treatment by the method.

In one embodiment of the invention, the impurity or doping material comprises at least one chemical element.

In some cases, the impurities can be the same impurities, i.e. preferentially impurities comprising the same chemical elements.

In some other cases, the impurities can be different impurities, i.e. preferentially impurities comprising at least one different chemical element.

In some cases, the predominant chemical elements can be the same predominant chemical elements, i.e. preferentially predominant chemical elements comprising the same chemical elements.

In some other cases, the predominant chemical elements can be different predominant chemical elements, i.e. preferentially predominant chemical elements comprising at least one different chemical element.

In one embodiment of the invention, the chemical element(s), predominant chemical element(s), doping material(s), and/or impurity(ies), are/is or represent(s) more than 1, 10, $10^3$, $10^5$, $10^{10}$, $10^{20}$, $10^{50}$ or $10^{100}$ chemical element(s), predominant chemical element(s), doping material(s), and/or impurity(ies).

In another embodiment of the invention, the chemical element(s), predominant chemical element(s), doping material(s), and/or impurity(ies), is/are or represent(s) less than $10^{100}$, $10^{50}$, $10^{20}$, $10^{10}$, $10^5$, $10^3$, 100, 50, 10, 5 or 2 chemical element(s), predominant chemical element(s), doping material(s), and/or impurity(ies).

In some cases, the chemical element(s), predominant chemical element(s), doping material(s), and/or impurity(ies), can be comprised inside the nanoparticle(s).

In some other cases, the chemical element(s), predominant chemical element(s), doping material(s), and/or impurity(ies), can be comprised at the surface of the nanoparticle(s).

In still some other cases, the chemical element(s), predominant chemical element(s), doping material(s), and/or impurity(ies), can be comprised outside of the nanoparticle(s).

In one embodiment of the invention, the chemical element(s), predominant chemical element(s), doping material(s), and/or impurity(ies), is/are comprised inside or occupy or is/are inserted in: i), the crystalline structure, ii), the amorphous structure, iii), a defect, and/or iv), a vacancy of the nanoparticle(s).

In one embodiment of the invention, the chemical element(s), predominant chemical element(s), doping material(s), and/or impurity(ies), is/are in interaction, such as electrostatic, strong, weak, nuclear, metallic, Van der Waals, Debye, London, or hydrogen interactions, with the nanoparticle(s).

In one embodiment of the invention, the chemical element(s), predominant chemical element(s), doping material(s), and/or impurity(ies), is/are located at a distance from the nanoparticle(s), preferentially from the center, central part, or surface of the nanoparticle(s), which is lower than $10^{50}$, $10^{20}$, $10^{10}$, $10^5$, $10^3$, 100, 10, 5 or 1 nm.

In still another embodiment of the invention, the chemical element(s), predominant chemical element(s), doping material(s), and/or impurity(ies), is/are located at a distance from nanoparticle(s), preferentially from the center, central part, or surface of the nanoparticle(s), which is larger than 0.001, 0.01, 0.1, 1, 10, 100, $10^3$, $10^5$, $10^{10}$, $10^{20}$ or $10^{50}$ nm.

In one embodiment of the invention, the chemical element(s), preferentially comprised in the impurity, is/are selected from the group consisting of: actinide, actinium, aluminium, americium, antimony, argon, arsenic, astatine, barium, berkelium, beryllium, bismuth, bohrium, boron, bromine, caesium, calcium, californium, carbon, cerium, chlorine, chromium, cobalt, copernicum, cadmium, copper, curium, darmstadtium, dubnium, dysprosium, einsteinium, erbium, europium, fermium, fleovium, fluorine, francium, gadolinium, gallium, germanium, gold, hafnium, helium, hessium, holmium, hydrogen, indium, iodine, iridium, iron, krypton, lanthanide, lanthanum, lawrencium, lead, lithium, livermorium, lutetium, magnesium, manganese, meitherium, mendelevium, mercury, molybdenum, neodymium, neon, neptunium, nickel, niobium, nitrogen, nobelium, osmium, oxygen, palladium, phosphorus, platinum, plutonium, polonium, potassium, praseodymium, proctactinium, promethium, radium, radon, rhenium, rhodium, roentgenium, rubidium, ruthenium, rutherfordium, samarium, selenium, silicon, silver, sodium, strontium, sulphur, scandium, seaborgium, tellurium, terbium, thorium, thulium, tin, tantalum, technetium, thallium, titanium, tungsten, ununoctium, ununpentium, ununseptium, ununtrium, uranium, vanadium, xenon, ytterbium, yttrium, zinc, zirconium, and any derivative of these chemical elements.

In one embodiment of the invention, the impurity is or comprises at least one chemical element that is different from at least one chemical element comprised in the predominant chemical element and/or doping material. For example, the impurity can be a toxic chemical element whereas the predominant chemical element and/or doping material are non-toxic.

In some cases, toxicity can be measured at the same concentration for the impurity, predominant chemical element, and doping material.

In some cases, toxicity can be toxicity towards cell or animal, or toxicity that can destroy, denature, kill, dessassemble at least one cell or one animal.

In another embodiment of the invention, the impurity is or comprises at least one chemical element that is the same as at least one chemical element comprised in the predominant chemical element and/or doping material. For example, the impurity can be made of the same chemical element as the doping material or predominant chemical element, but in a different ionic form. For example, the impurity can be made of $Fe^{2+}$, while the predominant chemical element can be made of $Fe^{3+}$.

In an embodiment of the invention, the doping material is or comprises at least one chemical element that is different from at least one chemical element comprised in the predominant chemical element and/or impurity.

In another embodiment of the invention, the doping material is or comprises at least one chemical element that is the same as at least one chemical element comprised in the predominant chemical element and/or impurity.

In another embodiment of the invention, the predominant chemical element is or comprises at least one chemical element that is different from at least one chemical element comprised in the impurity and/or doping material.

In another embodiment of the invention, the predominant chemical element is or comprises at least one chemical element that is the same as least one chemical element comprised in the impurity and/or doping material.

In one embodiment of the invention, the impurity is carbon or carbonaceous material.

In one embodiment of the invention, the doping material is carbon or carbonaceous material.

In one embodiment of the invention, the percentage, preferentially in mass, of the predominant chemical element(s) comprised inside or at the surface of the nanoparticle(s) is larger than $10^{-40}$, $10^{-20}$, $10^{-10}$, $10^{-5}$, $10^{-2}$, $10^{-1}$, 1, 5, 10, 25, 50, 75, 80 or 90%. In some cases, this situation can occur when the nanoparticles comprise a low quantity of impurity(ies) and/or doping material.

In another embodiment of the invention, the percentage, preferentially in mass, of the predominant chemical element(s) comprised inside or at the surface of the nanoparticle(s) is lower than $10^{40}$, $10^{20}$, $10^{10}$, $10^{5}$, $10^{2}$, 10, 5, 1, 0.1 or 0.001%. In some cases, this situation can occur when the nanoparticles comprise a large quantity of impurity(ies) and/or doping material.

According to the invention, this percentage can in some cases be defined as the ratio between the number of atoms, quantity, mass, or volume of predominant chemical element(s) comprised in the nanoparticle(s) divided by the total number of atoms, quantity, mass, or volume of all chemical element(s) comprised in the nanoparticle(s).

In one embodiment of the invention, the percentage, preferentially in mass, of the impurity(ies) comprised inside or at the surface of the nanoparticle(s) is larger than $10^{-40}$, $10^{-20}$, $10^{-10}$, $10^{-5}$, $10^{-2}$, $10^{-1}$, 1, 5, 10, 25, 50, 75, 80 or 90%. In some cases, this situation can occur before the nanoparticles have been treated by the method or when the treatment of the nanoparticles by the method does not lead to a large quantity of impurity(ies) removed from the nanoparticles.

In another embodiment of the invention, the percentage, preferentially in mass, of the impurity(ies) comprised inside or at the surface of the nanoparticle(s) is lower than $10^{40}$, $10^{20}$, $10^{10}$, $10^{5}$, $10^{2}$, 10, 5, 1, 0.1 or 0.001%. In some cases, this situation can occur after the nanoparticles have been treated by the method or when the treatment of the nanoparticles by the method leads to a large quantity of impurity(ies) removed from the nanoparticles.

According to the invention, this percentage can in some cases be defined as the ratio between the number of atoms, quantity, mass, or volume of impurity(ies) comprised in the nanoparticle(s) divided by the total number of atoms, quantity, mass, or volume of all chemical element(s) comprised in the nanoparticle(s).

In one embodiment of the invention, all chemical element(s) comprised in the nanoparticle(s) is/are the sum of the predominant chemical element(s) and impurity(ies) and doping material comprised in the nanoparticle(s).

In one embodiment of the invention, the concentration of the impurity(ies) comprised inside or at the surface of the nanoparticle(s) is lower than $10^{50}$, $10^{30}$, $10^{10}$, $10^{5}$, $10^{3}$, 500, 100, 50, 10, 1, $10^{-1}$, $10^{-3}$, $10^{-5}$, $10^{-10}$ or $10^{-50}$ μg of impurity(ies) per gram of nanoparticle(s). In some cases, this situation can occur after the nanoparticles have been treated by the method or when the treatment of the nanoparticles by the method leads to a large quantity of impurity(ies) removed from the nanoparticles.

In still another embodiment of the invention, the concentration of impurity(ies) comprised inside or at the surface of the nanoparticle(s) is larger than $10^{-100}$, $10^{-50}$, $10^{-20}$, $10^{-10}$, $10^{-5}$, $10^{-3}$, $10^{-2}$, $10^{-1}$, 1, 10, 50, 100, $10^{3}$, $10^{5}$ or $10^{10}$ μg of impurity(ies) per gram of nanoparticle(s). In some cases, this situation can occur before the nanoparticles have been treated by the method or when the treatment of the nanoparticles by the method does not lead to a large quantity of impurity(ies) removed from the nanoparticles.

In one embodiment of the invention, the concentration of the predominant chemical element(s) comprised inside or at the surface of the nanoparticle(s) is lower than $10^{50}$, $10^{30}$, $10^{10}$, $10^{5}$, $10^{3}$, 500, 100, 50, 10, 1, $10^{-1}$, $10^{-3}$, $10^{-5}$, $10^{-10}$ or $10^{-50}$ μg of predominant chemical element(s) per gram of nanoparticle(s). In some cases, this situation can occur when the quantity of impurity(ies) and/or doping material in the nanoparticles is large.

In still another embodiment of the invention, the concentration of the predominant chemical element(s) comprised inside or at the surface of the nanoparticle(s) is larger than $10^{-100}$, $10^{-50}$, $10^{-20}$, $10^{-10}$, $10^{-5}$, $10^{-3}$, $10^{-2}$, $10^{-1}$, 1, 10, 50, 100, $10^{3}$, $10^{5}$ or $10^{10}$ μg of predominant chemical element(s) per gram of nanoparticle(s). In some cases, this situation can occur when the quantity of impurity(ies) and/or doping material in the nanoparticles is low.

In another embodiment of the invention, the percentage, concentration, number of atoms, quantity, mass, or volume of predominant chemical element comprised inside or at the surface of the nanoparticle(s) is larger, preferentially by a factor of at least 1.00001, 1.001, 1.1, 2, 5, 10, 50, $10^{2}$, $10^{3}$, $10^{5}$, $10^{10}$, $10^{20}$, or $10^{50}$, than the percentage, concentration, number of atoms, quantity, mass, or volume of impurity(ies) comprised inside or at the surface of the nanoparticle(s). In some cases, this situation occurs before, during, or after the treatment of the nanoparticles by the method. In some cases, the factor can be larger after than before the treatment of the nanoparticles by the method.

In some cases, the surface of the nanoparticle can designate at least one chemical element, predominant chemical element, impurity, or doping material that is located at a distance of less than $10^{9}$, $10^{6}$, $10^{3}$, 10, 1 or 0.1 nm from the nanoparticle or that is located in the environment of the nanoparticle.

In some other cases, the surface of the nanoparticle can designate at least one chemical element, predominant chemical element, impurity, or doping material that is located at a distance of more than 0.1, 1, 5, 10, $10^3$, $10^6$ or $10^9$ nm from the nanoparticle.

In another embodiment of the invention, the nanoparticle(s) according the invention comprise(s) a core, also designed as the core, which is preferentially crystalized, preferentially magnetic, with a size preferentially comprised between 0.1 nm and 10 μm.

In one embodiment of the invention, the core of the nanoparticle is the part of the nanoparticle that cannot be removed or destroyed by the method. In some cases, the core can be oxidized when the nanoparticles are treated by the method, for example from a magnetite or intermediate composition between magnetite and maghemite to a full maghemite composition or from a magnetite or maghemite composition to a hematite composition.

In one embodiment of the invention, the method oxidizes the nanoparticles to an intermediate composition between magnetite and maghemite or to a full maghemite. Such composition can be desired since maghemite is stable, leads to ferrimagnetic behavior in some cases, and can be less toxic than magnetite.

In another embodiment of the invention, the method oxidizes the nanoparticles to hematite. Such composition can in some cases be avoided since hematite does not lead to a ferrimagnetic behavior.

In another embodiment of the invention, the nanoparticle(s) comprise(s) a coating, also designed as the coating, which preferentially surrounds the core of the nanoparticle(s). The coating preferentially has a thickness between 0.1 nm and 10 μm, and/or preferentially comprises a large percentage of carbonaceous material. Preferentially, the coating enables the stabilization and/or the homogenous distribution of the nanoparticle(s).

In another embodiment of the invention, the coating can be removed and released from the nanoparticles by the method or destroyed by the method.

In one embodiment of the invention, the nanoparticle(s) is/are or is/are made of or consists of or comprise(s) the core of the nanoparticle(s). In some cases, the nanoparticle(s) is/are not or do/does not comprise or is/are not made of the coating of the nanoparticle(s).

In one embodiment of the invention, the nanoparticle(s) is/are or is/are made of or consists of or comprise(s) the coating of the nanoparticle(s). In some cases, the nanoparticle(s) is/are not or do/does not comprise or is/are not made of the core of the nanoparticle(s).

In one embodiment of the invention, the nanoparticle(s) is/are or is/are made of or consist of or comprise(s) the core and coating of the nanoparticle(s).

In one embodiment of the invention, the nanoparticle, the core, and/or coating comprise(s) less than 99.99999, 99. 99, 99.9, 99, 95, 90, 80, 50, 40, 20 or 10 percent or percent in mass of carbon or carbonaceous material.

In one embodiment of the invention, the nanoparticle, the core, and/or coating comprise(s) less than 99.99999, 99. 99, 99.9, 99, 95, 90, 80, 50, 40, 20 or 10 percent or percent in mass of impurity(ies).

In some cases, the nanoparticle, the core, and/or coating can comprise a low percentage of impurity(ies) and/or carbonaceous material after the treatment of the nanoparticles by the method according to the invention.

In one embodiment of the invention, the nanoparticle, the core, and/or coating comprise(s) more than 0.00001, 0.001, 0.1, 1, 5, 10, 50 or 75 percent or percent in mass of carbon or carbonaceous material.

In one embodiment of the invention, the nanoparticle, the core, and/or coating comprise(s) more than 0.00001, 0.001, 0.1, 1, 5, 10, 50 or 75 percent or percent in mass of impurity(ies).

In some cases, the nanoparticle, the core, and/or coating can comprise a large percentage of impurity(ies) and/or carbonaceous material before the treatment of the nanoparticles by the method according to the invention.

In still another embodiment of the invention, the core comprises less than 99.99999, 99. 99, 99.9, 99, 95, 90, 80, 50, 40, 20, or 10 percent or percent in mass of carbon or carbonaceous material while the coating comprises more than 0.00001, 0.001, 0.1, 1, 5, 10, 50 or 75 percent or percent in mass of carbon or carbonaceous material.

In still another embodiment of the invention, the core comprises less than 99.99999, 99. 99, 99.9, 99, 95, 90, 80, 50, 40, 20 or 10 percent or percent in mass of impurity(ies) while the coating comprises more than 0.00001, 0.001, 0.1, 1, 5, 10, 50 or 75 percent or percent in mass of impurity(ies).

In still another embodiment of the invention, the core comprises more than 99.99999, 99. 99, 99.9, 99, 95, 90, 80, 50, 40, 20 or 10 percent or percent in mass of predominant chemical element(s) while the coating comprises less than 0.00001, 0.001, 0.1, 1, 5, 10, 50 or 75 percent or percent in mass of predominant chemical element(s).

In one embodiment of the invention, the carbonaceous material comprises at least one carbon atom, preferentially but not necessarily mixed or assembled with other chemical element(s) than carbon.

In one embodiment of the invention, the percentage of carbonaceous material is the ratio between the quantity, volume, number of atoms, or mass, of carbonaceous material in the core and/or coating of the nanoparticle(s) divided by the total quantity, number of atoms, or mass, of all chemical element(s) comprised in the core and/or coating of the nanoparticle(s).

In still another embodiment of the invention, the carbonaceous material originates from, is produced by, or comes from the cell(s).

In one embodiment of the invention, the nanoparticle(s), the core, and/or coating of the nanoparticle(s), has/have at least one of the following properties:

(a) magnetic, diamagnetic, superparamagnetic, ferromagnetic, ferrimagnetic, and/or paramagnetic behavior(s) or property(ies), preferentially observed under the application of magnetic field of strength preferentially larger than $10^{-50}$, $10^{-40}$, $10^{-20}$, $10^{-10}$, $10^{-5}$, $10^{-2}$ or $10^{-1}$ T, preferentially observed at temperatures lower than $10^{10}$, $10^5$, $10^3$, $10^2$, 10 or 1 K. In some cases, the core can have different magnetic property(ies) from the coating. For example, the core can be ferromagnetic or superparamagnetic while the coating can be diamagnetic or paramagnetic;

(b) a crystalline part or structure comprising at least 1, 2, 5, 10, 50, 100, $10^3$, $10^5$, $10^7$, $10^9$, $10^{20}$ or $10^{50}$ crystalline plane(s) or crystalline ordered structures, which can preferentially be observed or measured under electron microscopy. In some cases, the core can have a different crystalline structure from the coating. For example, the core can comprise more than 1, 5, 10, $10^3$ or $10^5$ crystalline plane(s) or crystalline ordered structure(s) while the coating can have less than $10^5$, $10^3$, 10, 5 or 2 crystalline planes or crystalline ordered structures;

(c) a composition made of metal(s) or metal oxide(s), preferentially iron oxide, most preferentially maghemite and/or magnetite. In some cases, the core comprises a different composition from the coating. For example, the core comprises more than 1, 5, 10, 25, 50, 75, 90, 95 or 99 percent or percent in mass of iron oxide while the coating comprises less than 99, 95, 90, 75, 50, 10, 5 or 1 percent or percent in mass of iron oxide. This percentage can be the ratio between the quantity, volume, number of atoms, mass of iron oxide comprised in the core and/or coating divided by the total quantity, total volume, total number of atoms, total mass, of all chemical element(s) comprised in the core and/or coating;

(d) single domain, or be magnetically mono-domain, (e) comprise a magnetic microstructure, which can be characterized by the presence of magnetic field lines, which can be oriented in a preferential direction such as an axis of easy magnetization or a crystallographic direction of the core of the nanoparticle(s) such as [111], where such a magnetic microstructure can under certain conditions be observable, in particular by electronic holography, (f) a size comprised between 1 nm and $10^5$ μm, 1 nm and $10^3$ μm, 1 nm and 100 μm, 1 nm and 10 μm, 1 nm and 1 μm, 5 nm and 1 μm, 5 and 500 nm, 5 and 250 nm, 5 and 100 nm, 5 and 80 nm, 5 and 60 nm, 10 nm and 1 μm, 10 and 500 nm, 10 and 250 nm, 10 and 100 nm, 10 and 80 nm, 10 and 60 nm, 15 nm and 1 μm, 15 and 500 nm, 15 and 250 nm, 15 and 100 nm, 15 and 80 nm, 15 and 60 nm, 20 nm and 1 μm, 20 and 500 nm, 20 and 250 nm, 20 and 100 nm, 20 and 80 nm or between 20 and 60 nm, (g) a size larger than 0.1, 1, 2, 5, 10, 15, 20, 25, 30, 35 or 40 nm, (h) a size lower than $10^{10}$, $10^5$, $10^4$, 2000, 1000, 500, 400, 300, 200, 150, 120, 100, 95, 90, 80, 75, 70, 65, 60, 55, 50, 45, 40, 35, 30, 25, 20, 15, 10 or 5 nm, (i) a zeta potential, charge, or surface charge comprised between $-10^{10}$ mV and $10^{10}$ mV, $-10^5$ mV and $10^5$ mV, $-10^4$ mV and $10^4$ mV, $-10^3$ mV, $-10^2$ mV and $10^2$ mV, −10 and 10 mV, preferentially at pH comprised between 0 and 14, 1 and 13, 2 and 12, 3 and 11, 4 and 10, 5 and 9 or between 6 and 8, (j) a zeta potential, charge, or surface charge larger than $-10^{50}$, $-10^{20}$, $-10^{10}$, $-10^5$, $-10^3$, −10, −5, −1, 0, 5, 10, 20, 50, or 100 mV, preferentially at pH larger than 0, 1, 2, 3, 4, 5, 6, 7, 8, 9, 10, 11, 12 or 13, (k) a zeta potential, charge, or surface charge larger than $-10^{50}$, $-10^{20}$, $-10^{10}$, $-10^5$, $-10^3$, −10, −5, −1, 0, 5, 10, 20, 50, or 100 mV, preferentially at pH lower than 14, 13, 12, 11, 10, 9, 8, 7, 6, 5, 4, 3, 2, 1, or 0, (l) a zeta potential, charge, or surface charge lower than $10^{50}$, $10^{20}$, $10^{10}$, $10^5$, $10^3$, 10, 5, 1, 0, −5, −10, −20, −50 or −100 mV, preferentially at pH larger than 0, 1, 2, 3, 4, 5, 6, 7, 8, 9, 10, 11, 12 or 13, (m) a zeta potential, charge, or surface charge lower than $10^{50}$, $10^{20}$, $10^{10}$, $10^5$, $10^3$, 10, 5, 1, 0, −5, −10, −20, −50, or −100 mV, preferentially at pH lower than 14, 13, 12, 11, 10, 9, 8, 7, 6, 5, 4, 3, 2, 1 or 0, (n) an isoelectric point comprised between 0 and 14, 1 and 13, 2 and 12, 3 and 11, 4 and 10, 5 and 9 or between 6 and 8, (o) an isoelectric point larger than 0, 1, 2, 3, 4, 5, 6, 7, 8, 9, 10, 11, 12 or 13, and/or (p) an isoelectric point lower than 14, 13, 12, 11, 10, 9, 8, 7, 6, 5, 4, 3, 2, 1 or 0.

In one embodiment of the invention, the core and/or coating is/are produced by at least one nanoparticle-producing cell.

In one embodiment of the invention, the nanoparticle-producing cell(s) synthesize the nanoparticle(s) inside the cell(s). Preferentially nanoparticle(s) is/are synthesized inside cell(s) when they are synthesized, assembled, crystallized, partly or fully: i) by or in or near or inside part of the cell such as an organelle, Golgi vesicle or apparatus, endosome, exosome, ribosome, endoplasmic reticulum, actin filament, nucleus, peroxisome, microtubule, lysosome, mitochondrion, filament, centrosome, flagellum, or the cell membrane, ii) in a region that is located inside the cell(s), or iii) in a region located at a distance from part of the cell(s) that is lower than $10^5$, $10^3$, 100, 10 or 1 nm.

In another embodiment of the invention, the nanoparticle-producing cell(s) synthesize the nanoparticle(s) outside the cell(s). Preferentially nanoparticle(s) is/are synthesized outside the cell(s) when it/they is/are synthesized, assembled, crystallized, partly or fully: i) in a region that is located outside the cell(s), or ii) in a region located at a distance from part of the cell(s) that is larger 1, 10, 100, $10^3$ or $10^5$ nm.

In one embodiment of the invention, the cell(s) comprise(s) or is/are assemblies of more than 1, 10, $10^3$, $10^5$, $10^{10}$, $10^{20}$, $10^{50}$, or $10^{100}$ cell(s), preferentially per liter of growth medium.

In another embodiment of the invention, the cell(s) comprise(s) or is/are assemblies of less than $10^{100}$, $10^{50}$, $10^{20}$, $10^{10}$, $10^5$, $10^3$, 100, 50, 10, 5 or 2 cell(s), preferentially per liter of growth medium.

In one embodiment of the invention, the nanoparticle-producing cell(s) is/are eukaryotic cell(s), preferentially belonging to mammalians, humans, animals, plants, trees, flours, branches, mushrooms, fungi, archae, birds, fishes, pigeons, trout, mammals, ants, bees, or insects.

In one embodiment of the invention, the nanoparticle-producing cell(s) is/are prokaryotic cell(s) or bacteria.

In some cases, the nanoparticle-producing cells can be Mycobacterium, preferentially Mycobacterium paratuberculosis, Shewanella, preferentially Shewanella oneidensi, Geothrix, preferentially Geothrix fermentans. These bacteria preferentially synthesize nanoparticle(s) outside the cells.

In some other cases, the nanoparticle-producing cells can be magnetotactic bacteria, such as Magnetospirillum magneticum strain AMB-1, magnetotactic coccus strain MC-1, three facultative anaerobic vibrios strains MV-1, MV-2 and MV-4, the Magnetospirillum magnetotacticum strain MS-1, the Magnetospirillum gryphiswaldense strain MSR-1, a facultative anerobic magnetotactic spirillum, Magnetospirillum magneticum strain MGT-1, and an obligate anaerobe, Desulfovibrio magneticus RS-1. These bacteria preferentially synthetize nanoparticle(s) inside the cell(s).

In another embodiment of the invention, the core and/or coating is/are not produced by the nanoparticle-producing cell(s).

In one embodiment of the invention, the core of the nanoparticle(s) is produced by the nanoparticle-producing cell(s) while the coating of the nanoparticle(s) is not produced by the nanoparticle-producing cell(s).

In another embodiment of the invention, the coating of the nanoparticle(s) is produced by the nanoparticle-producing cell(s) while the core of the nanoparticle(s) is not produced by the nanoparticle-producing cell(s).

In one embodiment of the invention, the method is preceded by additional step(s) of isolating or extracting the nanoparticles from the nanoparticle-producing cells. In some cases, the preceding step is a step of recovering the nanoparticles. In some cases, the preceding step is carried out by: i) mixing the cells, preferentially obtained from the growth step, with a detergent such as KOH or NaOH, ii) heating the cells at a temperature larger than −270, −250, −200, −150, −100, −50, −30, −10, −5, 0, 5, 10, 20, 30, 50, 75, 100, 150, 200, 500, $10^3$, $10^5$ or $10^{10}$° C. or comprised between −270 and $10^{10}$, −100 and $10^5$, or between 0 and 100° C., iii) inducing a temperature gradient larger than $10^{-50}$, $10^{-20}$, $10^{-10}$, $10^{-5}$, $10^{-3}$, $10^{-1}$, 1, 2, 5, 10, $10^3$, $10^5$, $10^{10}$° C. per hour, minute or second, or comprised between $10^{-50}$ and $10^{10}$° ° C. per hour, minute or second, iii) applying a pressure on the cells, preferentially larger than 1, 10, 100, 500, $10^3$, $10^4$, $10^5$, $10^6$, $10^7$, $10^8$ or $10^9$ atmosphere(s), or comprised between 1 and $10^9$ atmosphere(s), using for example a French press, and/or iv) sonicating the cells, preferentially at a power larger than $10^{-50}$, $10^{-20}$, $10^{-5}$, $10^{-1}$, 1, 10, $10^2$, $10^3$, $10^5$ or $10^{10}$W.

In one embodiment of the invention, the nanoparticles are chemically synthesized nanoparticles. In some cases, a chemical synthesis does not involve cells or living organism to produce the nanoparticles.

In one embodiment of the invention, the presence of impurity in the nanoparticles can come from the chemicals that are used for the synthesis of the nanoparticles or from chemicals comprised in the medium surrounding the nanoparticles such as endotoxins or heavy metals.

In one embodiment of the invention, the method according to the invention comprises the following heating steps in which or during which:

- During step 1, the temperature of the nanoparticles is increased, preferentially from a temperature $T_i$ up to a temperature $T_1$ during a lapse of time $t_{i1}$ and is maintained at temperature $T_1$, preferentially comprised between 190° C. and 210° C., during a heating time $t_1$, preferentially comprised between 5 min and 24 hours.
- During step 2, the temperature of the nanoparticles is preferentially increased from the temperature $T_1$ up to the temperature $T_2$ during a lapse of time $t_{12}$, and is preferentially maintained at temperature $T_2$, preferentially comprised between 370 and 400° C. during a heating time $t_2$, preferentially comprised between 5 min and 24 hours.

In one embodiment of the invention, the method according to the invention comprises the following heating steps in which or during which:

- During step 1, the temperature of the nanoparticles is increased, preferentially from a temperature $T_i$ up to a temperature $T_1$ during a lapse of time $t_{i1}$ and is maintained at temperature $T_1$, preferentially comprised between 190° C. and 210° C., during a heating time $t_1$, preferentially comprised between 5 min and 24 hours.
- During an intermediate step between step 1 and step 2, which is optional, the temperature of the nanoparticles is increased from the temperature $T_1$ up to the temperature $T_3$ during a lapse of time $t_{13}$, and is preferentially maintained at temperature $T_3$, preferentially comprised between 290 and 310° C., during a heating time $t_3$, preferentially comprised between 5 min and 24 hours.
- During step 2, the temperature of the nanoparticles is preferentially increased up from the temperature $T_3$ up to the temperature $T_2$ during a lapse of time $t_{32}$, and is preferentially maintained at temperature $T_2$, preferentially comprised between 370 and 400° C., during a heating time $t_2$, preferentially comprised between 5 min and 24 hours.

In one embodiment of the invention, the temperatures $T_1$ and/or $T_2$ is/are determined by:

i) measuring the variation of the percentage in weight of the nanoparticles as a function of temperature when the nanoparticles are heated between two temperatures, preferentially $T_{T<T1}$ and $T_{T>T2}$, ii) measuring or representing or considering or examining or using at least one peak of the derivative of the variation of this percentage as a function of temperature, iii) estimating or deducing from the variation of the percentage in weight of the nanoparticles as a function of temperature, the interval of temperature in which this variation is maximum, where the minimum and maximum temperatures of this interval are $T_1$ and $T_2$, respectively, and iv) estimating or deducing from the plot of the derivative of the variation of the percentage in weight of the nanoparticles, preferentially being in a y or vertical axis, as a function of temperature, preferentially being an x or an horizontal axis, at least: a) the position and/or existence of at least one peak in this plot, b) the temperature, preferentially $T_1$, corresponding or being at the beginning of this peak or down-stream of this peak or at the location where the peak starts to display an increase of the derivative of the variation of the percentage in weight of the nanoparticles as a function of temperature or at the location where the temperature $T_1$ is lower, preferentially by a factor of more than 1.0001, 1.1, 1.2, 1.5, 2, 5, 10, $10^3$, $10^5$, $10^7$ or $10^{10}$, than the temperature corresponding to or leading to the maximum value of this peak, $T_{maxpeak}$, or at the location where the temperature is lower, preferentially by a factor of more than $10^{-10}$, $10^{-5}$, $10^{-3}$, $10^{-1}$, 1, 5, 10 or 100° C. than $T_{maxpeak}$ or at the location where the temperature $T_1$ is lower, preferentially by a factor of more than 1.0001, 1.1, 1.2, 1.5, 2, 5, 10, $10^3$, $10^5$, $10^7$ or $10^{10}$, than the temperature corresponding to or leading to the minimum value of the FWHM of this peak, $T_{minFWHM}$, or at the location where the temperature is lower, preferentially by a factor of more than $10^{-10}$, $10^{-5}$, $10^{-3}$, $10^{-1}$, 1, 5, 10 or 100° C. than $T_{minFWHM}$, c) the temperature, preferentially $T_2$, corresponding or being at the end of this peak or up-stream of this peak or at the location where the peak finishes to display a decrease of the derivative of the variation of the percentage in weight of the nanoparticles as a function of temperature or at the location where the temperature $T_2$ is larger, preferentially by a factor of more than 1.0001, 1.1, 1.2, 1.5, 2, 5, 10, $10^3$, $10^5$, $10^7$ or $10^{10}$, than the temperature corresponding to or leading to the maximum value of this peak, $T_{maxpeak}$, or at the location where the temperature is larger, preferentially by a factor of more than $10^{-10}$, $10^{-5}$, $10^{-3}$, $10^{-1}$, 1, 5, 10 or 100° C. than $T_{maxpeak}$ or at the location where the temperature $T_2$ is larger, preferentially by a factor of more than 1.0001, 1.1, 1.2, 1.5, 2, 5, 10, $10^3$, $10^5$, $10^7$ or $10^{10}$, than the temperature corresponding to or leading to the maximum value of the FWHM of this peak, $T_{maxFWHM}$, or at the location where the temperature is larger, preferentially by a factor of more than $10^{-10}$, $10^{-5}$, $10^{-3}$, $10^{-1}$, 1, 5, 10 or 100° C. than $T_{maxFWHM}$.

Figure 4:
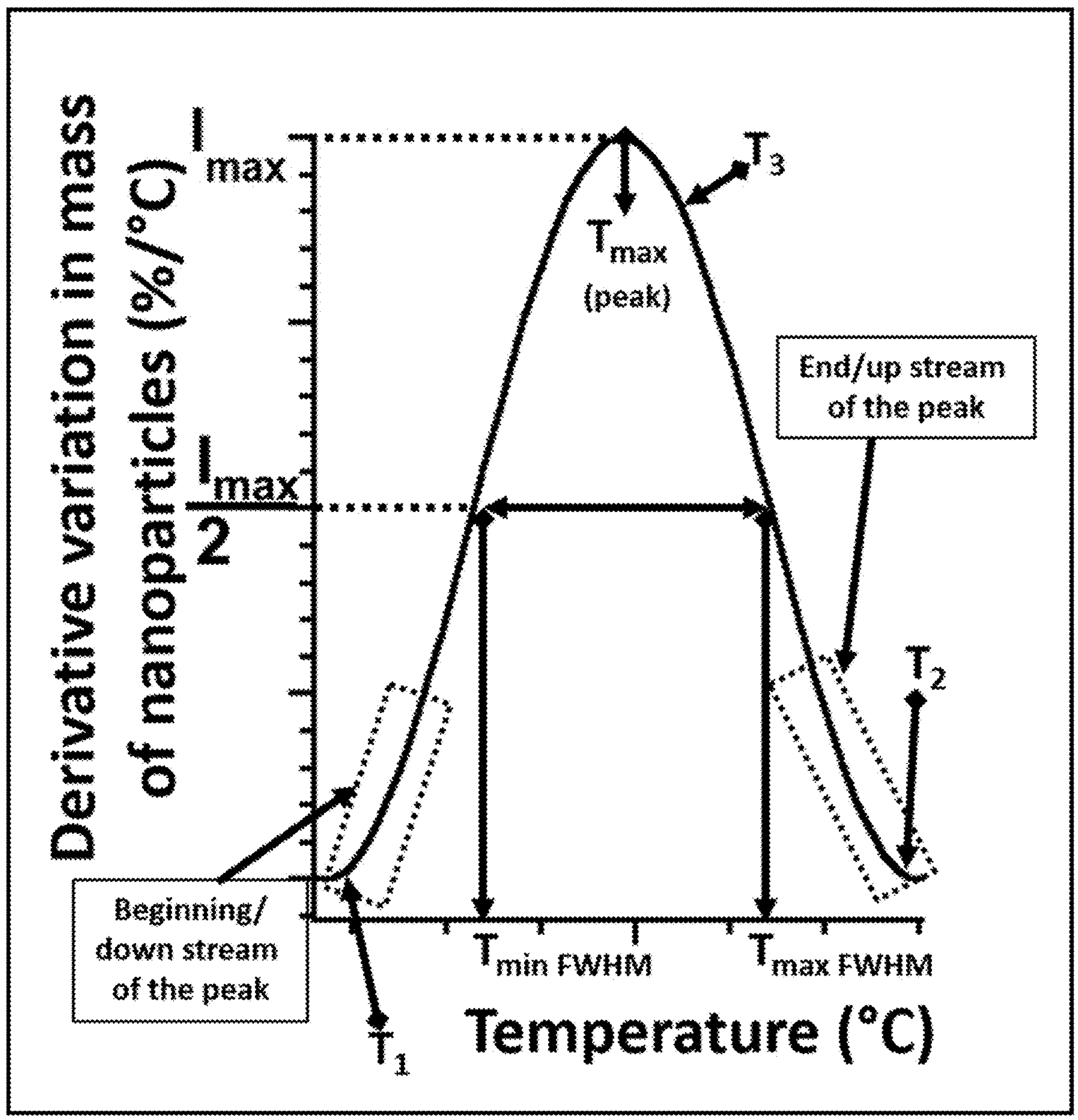
FIG. 4: Schematic diagram representing a peak due to the variation as a function of temperature of the derivative of the variation in mass of the nanoparticles as a function of temperature. $T_{max(peak)}$, $T_{minFWHM}$, $T_{maxFWHM}$, are the temperature leading to the maximum value of the heat flow ($I_{max}$) for $T_{max(peak)}$, the values of the heat flow equal to $I_{max}/2$ for the temperatures $T_{minFWHM}$ and $T_{maxFWHM}$, where $T_{minFWHM}<T_{maxFWHM}$. The regions of: i) the beginning or downstream of the peak and ii) the end or upstream of the peak are indicated. The locations of $T_1$, $T_2$, and $T_3$, relatively to the peak, are indicated.
Figure 5:
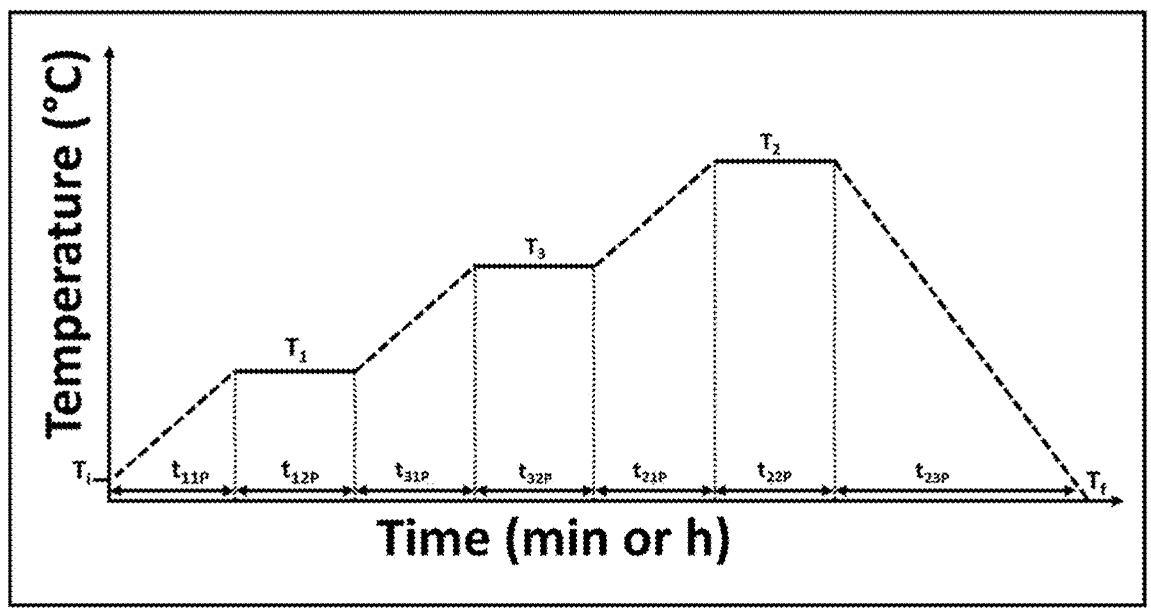
FIG. 5: Schematic diagram representing a typical heat treatment that was used to heat the nanoparticles, where the temperature of the nanoparticles was increased from a temperature $T_i$ to a temperature $T_1$ during a time $t_{11P}$, then the temperature of the nanoparticles was maintained at temperature $T_1$ during $t_{12P}$, then the temperature of the nanoparticles was increased from $T_1$ to $T_3$ during $t_{31P}$, then the temperature of the nanoparticles was maintained at a temperature $T_3$ during $t_{32P}$, then the temperature of the nanoparticles was increased from $T_3$ to $T_2$ during $t_{21P}$, then the temperature of the nanoparticles was maintained at $T_2$ during $t_{22P}$, then the temperature of the nanoparticles was decreased from $T_2$ to $T_f$ during $t_{23P}$.

In one embodiment of the invention, FIG. 4 indicates for the peak of the derivative of the variation in mass of the nanoparticles, the position of $T_{minFWHM}$, $T_{maxFWHM}$, $T_{maxpeak}$, $T_1$, $T_2$, $T_3$, the beginning/downstream of this peak, the end/upstream of this peak.

In one embodiment of the invention, the temperature where or for which or at which the peak starts to display an increase of the derivative of the variation of the percentage in weight of the nanoparticles as a function of temperature is the temperature where or for which or at which the peak displays an increasing slope of the derivative of the variation of the percentage in weight of the nanoparticles as a function of temperature.

In one embodiment of the invention, the temperature where or for which or at which the peak stops to display an increase of the derivative of the variation of the percentage in weight of the nanoparticles as a function of temperature is the temperature where or for which or at which the peak displays a decreasing slope of the derivative of the variation of the percentage in weight of the nanoparticles as a function of temperature.

In another embodiment of the invention, the heat flux of the nanoparticles is the heat flux produced by the nanoparticles or released from the nanoparticles or originating from the nanoparticles, preferentially when the nanoparticles are heated with a heating apparatus such a furnace. Preferentially, the heat flux can be measured with an apparatus or using a thermo-analytical method, or using Differential thermo-analysis (DTA) or using differential scanning calorimetry (DSC).

In another embodiment of the invention, the temperature $T_i$ (i=1, 2, or 3) is determined by:

i) measuring the variation of the heat flux of the nanoparticles as a function of temperature, when the nanoparticles are heated between two temperatures $T_{T<T1}$ and $T_{T>T2}$, ii) measuring or representing or considering or examining or using at least one peak of the variation of the heat flux of the nanoparticles as a function of temperature, and iii) estimating the temperature $T_i$, corresponding to or being at the beginning of this peak or down-stream of this peak or at the location or temperature where the peak starts to display an increase of the variation of the heat flux of the nanoparticles as a function of temperature or at the location or temperature where the temperature $T_i$ is lower, preferentially by a factor of more than 1.0001, 1.1, 1.2, 1.5, 2, 5, 10, $10^3$, $10^5$, $10^7$ or $10^{10}$, than the temperature corresponding to or leading to the maximum value of this peak, $T_{maxheatflux}$, or at the location where the temperature is lower, preferentially by a factor of more than $10^{-10}$, $10^{-5}$, $10^{-3}$, $10^{-1}$, 1, 5, 10 or 100° C. than $T_{maxheatflux}$ or at the location where the temperature $T_i$ is lower, preferentially by a factor of more than 1.0001, 1.1, 1.2, 1.5, 2, 5, 10, $10^3$, $10^5$, $10^7$ or $10^{10}$, than the temperature corresponding to or leading to the maximum value of the FWHM of this peak, $T_{maxFWHMheatflux}$, or at the location where the temperature is lower, preferentially by a factor of more than $10^{-10}$, $10^{-5}$, $10^{-3}$, $10^{-1}$, 1, 5, 10 or 100° C. than $T_{maxFWHMheatflux}$.

Figure 3:
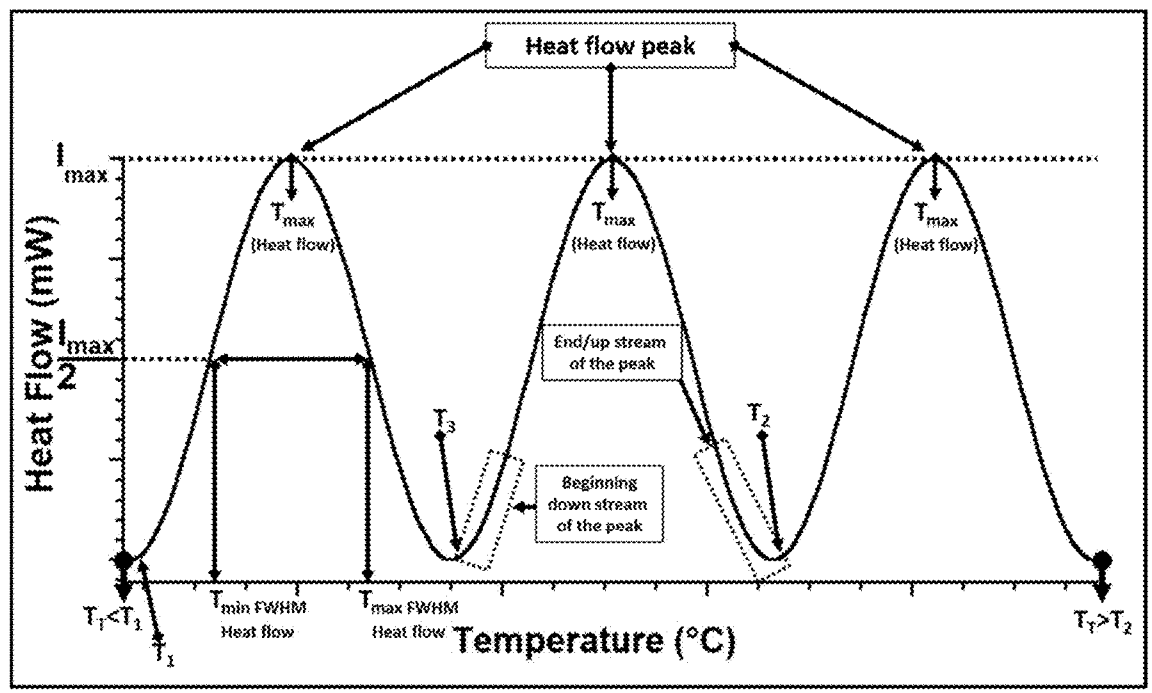
FIG. 3: Schematic diagram representing three different peaks due to the variation of the heat flow of nanoparticles as a function of temperature. $T_{max}$, $T_{minFWHMheatflow}$, $T_{maxFWHMheatflow}$, are the temperature leading to the maximum value of the heat flow ($I_{max}$) for $T_{maxheatflow}$, the values of the heat flow equal to $I_{max}/2$ for the temperatures $T_{minFWHMHeatflow}$ and $T_{maxFWHMHeatflow}$, where $T_{minFWHMHeatflow}<T_{maxFWHMHeatflow}$. The regions of: i) the beginning or downstream of the heat flow peak and ii) the end or upstream of the peak are indicated. The locations of $T_1$, $T_2$, and $T_3$, relatively to the heat flow peak, are indicated.

In one embodiment of the invention, FIG. 3 indicates three heat flow peaks produced when nanoparticles are heated, with the position of $T_1$, $T_2$, $T_3$, $T_{minFWHMheatflow}$, $T_{mawFWHMheatflow}$, $T_{maxheatflow}$.

In one embodiment of the invention, $T_{min\text{-}imp}$ is the minimum temperature above which: impurity(ies) or carbonaceous material or carbon is released or removed from the nanoparticles. In some cases, $T_{min\text{-}imp}$ is the temperature above which more than $10^{-50}$, $10^{-20}$, $10^{-10}$, $10^{-5}$, $10^{-2}$, $10^{-1}$, 1, 5, 10, 50 or 75%, preferentially percentage in mass, of carbonaceous material or carbon preferentially comprised in the nanoparticles, is released or removed from the nanoparticles. This percentage can be high, for example when $T_{min\text{-}imp}$ is a threshold temperature above which a large amount of impurity(ies) is removed or released from the nanoparticles. In some other cases, $T_{min\text{-}imp}$ is the temperature above which less than 75, 50, 10, 5, 1, $10^{-1}$, $10^{-2}$, $10^{-5}$, $10^{-10}$, $10^{-20}$ or $10^{-50}$%, preferentially percentage in mass, of carbonaceous material or carbon preferentially comprised in the nanoparticles, is released or removed from the nanoparticles. This percentage can be low, for example when the impurity(ies) is/are continuously removed from the nanoparticles when the latter are heated.

In another embodiment of the invention, $(T_{min})_i$ is temperature of the nanoparticles before or at the beginning of step i of the method. In some cases, $(T_{min})_i$ can be the temperature of the nanoparticles before the nanoparticles are treated or heated, preferentially with the heating apparatus.

In another embodiment of the invention, $T_{max\text{-}nano}$ is the heating temperature of the nanoparticles above which the nanoparticles are destroyed or denatures or oxidized, preferentially oxidized to induce a significant change in its magnetic properties such as a loss in ferromagnetic or ferrimagnetic properties. In some cases, $T_{max\text{-}nano}$ is the temperature above which the nanoparticles are oxidized, partly or fully, to hematite or to a different type of iron oxide than maghemite or magnetite.

In another embodiment of the invention, $T_{max\text{-}nano}$ is the temperature of the nanoparticles after the nanoparticles are treated by the method or after the nanoparticles are heated, preferentially with the heating apparatus.

In another embodiment of the invention, $(T_{max})_i$ is the temperature of the nanoparticles after or at the end of step i of the method. In some cases, $(T_{max})_i$ can be the temperature of the nanoparticles after the nanoparticles are treated or heated, preferentially with the heating apparatus.

In one embodiment of the invention, $T_{min\text{-}imp}$ and/or $T_{max\text{-}nano}$ and/or $(T_{min})_i$ and/or $(T_{max})_i$ is/are comprised between −273 and $10^{10}$° C., −273 and $10^3$° C., −250 and 100° C., −100 and 50° C., or 5 and 50° C.

In one embodiment of the invention, $T_{min\text{-}imp}$ and/or $T_{max\text{-}nano}$ and/or $(T_{min})_i$ and/or $(T_{max})_i$ is/are lower than $10^{50}$, $10^{20}$, $10^{10}$, $10^5$, $10^3$, $10^2$, 10, 5, 1, 0, −10, −50, −100, −200, −250 or −273° C.

In another embodiment of the invention, $T_{min\text{-}imp}$ and/or $T_{max\text{-}nano}$ and/or $(T_{min})_i$ and/or $(T_{max})_i$ is/are larger than −273, −250, −200, −150, −100, −50, −10, 0, 5, 10, $10^3$, $10^5$, $10^{10}$, $10^{20}$ or $10^{50}$° C.

In one embodiment of the invention, $T_{min\text{-}imp}$ is lower than $T_{max\text{-}nano}$ and/or $(T_{min})_i$ is lower than $(T_{min})_i$, preferentially by a factor of more than 1.0001, 1.1, 1.5, 2, 5, 10, 50 or 100.

In one embodiment of the invention, $T_{min\text{-}imp}$ is lower than $T_1$ and/or $T_2$ and/or $T_3$, preferentially by a factor of more than 1.0001, 1.1, 1.5, 2, 5, 10, 50 or 100.

In one embodiment of the invention, $(T_{min})_i$ is lower than $T_1$ and/or $T_2$ and/or $T_3$, preferentially by a factor of more than 1.0001, 1.1, 1.5, 2, 5, 10, 50 or 100.

In one embodiment of the invention, $T_{max\text{-}nano}$ is larger than $T_1$ and/or $T_2$ and/or $T_3$, preferentially by a factor of more than 1.0001, 1.1, 1.5, 2, 5, 10, 50 or 100.

In one embodiment of the invention, $(T_{max})_i$ is larger than $T_1$ and/or $T_2$ and/or $T_3$, preferentially by a factor of more than 1.0001, 1.1, 1.5, 2, 5, 10, 50 or 100.

In one embodiment of the invention, the peak of the derivative of the variation of the percentage in weight of the nanoparticles is an increase of this derivative, preferentially by a factor of more than 1.1, 1.2, 5, 10, 50, 100, $10^3$, $10^5$, $10^{10}$ or $10^{50}$, preferentially between $T_1$ and $T_3$, followed by a decrease of this derivative, preferentially by a factor of more than 1.1, 1.2, 5, 10, 50, 100, $10^3$, $10^5$, $10^{10}$ or $10^{50}$, preferentially between $T_3$ and $T_2$. In some cases, $T_3$ can lead to or be the maximum of the peak of this derivative.

In one embodiment of the invention, $T_1$ and/or $T_2$ and/or $T_3$ is/are comprised between −273 and $10^{10}$, −273 and $10^3$, −250 and $10^3$, −100 and $10^3$, 0 and $10^3$, 20 and $10^3$, 50 and 500, or between 300 and 500° C.

In one embodiment of the invention, $T_1$ and/or $T_2$ and/or $T_3$ is/are lower than $10^{50}$, $10^{20}$, $10^{10}$, $10^5$, $10^3$, $10^2$, 10, 5, 1, 0, −10, −50, −100, −200, −250 or −273° C.

In another embodiment of the invention, $T_1$ and/or $T_2$ and/or $T_3$ is/are larger than −273, −250, −200, −150, −100, −50, −10, 0, 5, 10, $10^3$, $10^5$, $10^{10}$, $10^{20}$ or $10^{50}$° C.

In one embodiment of the invention, the heating time(s) $t_1$, $t_2$, and/or $t_3$ is/are comprised between $10^{-50}$ and $10^{50}$, $10^{-20}$ and $10^{20}$, $10^{-10}$ and $10^{10}$, $10^{-5}$ and $10^5$, $10^{-3}$ and $10^3$, $10^{-2}$ and $10^3$, $10^{-2}$ and 100, or between $10^{-1}$ and 100 hour(s).

In another embodiment of the invention, the heating time(s) $t_1$, $t_2$, and/or $t_3$ is/are lower than $10^{50}$, $10^{30}$, $10^{20}$, $10^{10}$, $10^5$, $10^3$, 10, 1, $10^{-1}$, $10^{-3}$ or $10^{-5}$ hour(s).

In another embodiment of the invention, the heating time(s) $t_1$, $t_2$, and/or $t_3$ is/are larger than $10^{-50}$, $10^{-30}$, $10^{-20}$, $10^{-10}$, $10^{-5}$, $10^{-3}$, $10^{-1}$, 1, $10^1$, $10^3$ or $10^5$ hour(s).

In one embodiment of the invention, the percentage of variations of temperature when the temperature is maintained at the temperature $T_1$, $T_2$, or $T_3$, during $t_1$, $t_2$, and/or $t_3$, is lower than 100, 99, 90, 80, 70, 50, 30, 20, 10, 5, 2 or 1%. In some cases, this percentage can be $T_{1max}-T_{1min}/T_{1av}$ during step 1, $T_{2max}-T_{2min}/T_{2av}$ during step 2, $T_{3max}-T_{3min}/T_{3av}$ during step 3, where: i), $T_{1max}$, $T_{1min}$, and $T_{1av}$ are the maximum, minimum, and average temperatures reached during the maintenance of temperature at $T_1$ during $t_1$ of step 1, ii), $T_{2max}$, $T_{2min}$, and $T_{2av}$ are the maximum, minimum, and average temperatures reached during the maintenance of temperature at $T_2$ during $t_2$ of step 2, iii), $T_{3max}$, $T_{3min}$, and $T_{3av}$ are the maximum, minimum and average temperatures reached during the maintenance of temperature at $T_3$ during $t_3$ of step 3.

In one embodiment of the invention, the percentage of variations of temperature when the temperature is maintained at the temperature $T_1$, $T_2$, or $T_3$, during $t_1$, $t_2$, and/or $t_3$ of step(s) 1, 2, and/or 3, is lower than 100, 99, 90, 80, 70, 50, 30, 20, 10, 5, 2, 1, $10^{-10}$ or $10^{-50}$%. In some cases, this percentage can be low when the furnace used to heat the nanoparticles enables to maintain a stable temperature and/or when the nanoparticles are not releasing or absorbing heat during the treatment by the method.

In one embodiment of the invention, the percentage of variations of temperature when the temperature is maintained at the temperature $T_1$, $T_2$, or $T_3$, during $t_1$, $t_2$, and/or $t_3$ of step(s) 1, 2, and/or 3, is larger than $10^{-50}$, $10^{-20}$, $10^{-10}$, $10^{-5}$, $10^{-3}$, $10^{-1}$, 1, 5, 10, 20, 50, 75, 80, 90, 95, 99, 99.9 or 100%. In some cases, this percentage can be large when the nanoparticles absorb or release heat or when the temperature of the furnace used to heat the nanoparticles cannot be stabilized.

The invention also relates to a method for removing at least one impurity from metal-based nanoparticles, in which during step i, the temperature of the nanoparticles is increased up to a temperature $T_i$ and is maintained at this temperature during a heating time $t_{i2P}$, where the step i can be repeated n times.

In one embodiment of the invention, the method consists in heating the nanoparticles at n different temperatures $T_1 \ldots T_i \ldots T_n$, during the times $t_1 \ldots t_i \ldots t_n$, respectively, corresponding to the different heating steps $H_1 \ldots H_i \ldots H_n$.

In one embodiment of the invention, the method consists in heating the nanoparticle during at least one heating step or at least two heating steps.

In one embodiment of the invention, each heating step $H_i$ ($1<i<n$) is divided in at least one of the following three phases:

i) A first phase during which the temperature of the nanoparticles increases or is increased, preferentially by the heating apparatus, from an initial temperature $(T_{min})_i$ to a final temperature $T_i$. In some other cases, $(T_{min})_i$ is smaller than $10^{50}$, $10^{20}$, $10^{10}$, $10^5$, $10^2$, 10, 5, 1, −10, −50, −100 or −200° C. In some cases, $(T_{min})_i$ can be smaller, preferentially by a factor of more than 1.00001, 1.2, 1.5, 2, 5, 10, $10^3$ or $10^5$, preferentially by more than 0.0001, 0.1, 0.2, 0.5, 1, 2, 5, 10, 20, 50, 100, $10^3$ or $10^5$° C., than $T_i$. In some other cases, $((T_{min})_i$ can be smaller, preferentially by a factor of less than $10^5$, $10^3$, 100, 50, 20, 10, 5, 2, 1 or 0.1° C., than $T_i$. The initial temperature can be sufficiently low to avoid the melting or the destruction or the denaturation of the nanoparticles. In some cases, $(T_{min})_i$ is larger than −200, −100, −50, −10, 0, 10, $10^2$, $10^3$, $10^5$, or $10^{10}$° C. The initial temperature can be sufficiently large to avoid applying a too large temperature gradient to reach the average temperature of the second phase. In some cases, $(T_{min})_i$ is comprised between −200 and $10^{10}$° C., preferentially between 0 and $10^3$° C., most preferentially between 10 and 100° C. In some other cases, $T_i$ is the temperature of the second phase. In some cases, the temperature is increased from $(T_{min})_i$ to $T_i$ at a rate that is smaller than $10^{50}$, $10^{30}$, $10^{10}$, $10^5$, $10^3$, 10, 5, 2, 1, $10^{-1}$, $10^{-3}$, $10^{-5}$, $10^{-10}$ or $10^{-20}$° C. per minute. In some other cases, the temperature is increased from $(T_{min})_i$ to $T_i$ at a rate that is larger than $10^{-20}$, $10^{-10}$, $10^{-5}$, $10^{-3}$, $10^{-1}$, 1, 2, 5, 10, $10^3$, $10^5$, $10^{10}$, $10^{20}$ or $10^{50}$° C. per minute. In some cases, the time during which the temperature is increased from $(T_{min})_i$ to $T_i$, which is preferentially $t_{i1P}$, is larger than $10^{-50}$, $10^{-20}$, $10^{-10}$, $10^{-5}$, $10^{-3}$, $10^{-1}$, 1, 5, 10, $10^3$, $10^5$, $10^{10}$, $10^{30}$ or $10^{50}$ minute(s). In some other cases, the time during which the temperature is increased from $(T_{min})_i$ to $T_i$, is lower than $10^{50}$, $10^{20}$, $10^{10}$, $10^5$, $10^3$, 10, 5, 1, $10^{-1}$, $10^{-3}$, $10^{-5}$ or $10^{-10}$ minute(s). In some cases, the gradient of temperature during the first phase of step i is preferentially $[T_i-(T_{min})_i]/t_{i1P}$. In some other cases, the gradient of temperature during the first phase of step 1 is $\Delta T_i/\delta t_i$, where $\Delta T_i$ is a or any variation of temperature taking place during the first phase of step i and $\delta t_i$ is the lapse of time during which $\Delta T_i$ is occurring. In some cases, $\Delta T_i/\delta t_i$ or $(T_i-(T_{min})_i)t_{i1P}$ is larger than $10^{-50}$, $10^{-30}$, $10^{-20}$, $10^{-10}$, $10^{-5}$, $10^{-3}$, $10^{-2}$, $10^{-1}$, 1, 5, 10, $10^3$, $10^5$ or $10^{10}$° C. per minute. In some other cases, $\Delta T_i/\delta t_i$ or $(T_i-(T_{min})_i/t_{i1P}$ is lower than $10^{100}$, $10^{50}$, $10^{10}$, $10^5$, $10^3$, $10^2$, 10 or 1° C. per minute.

ii) A second phase during which the temperature of the nanoparticles remains or is maintained, preferentially by the heating and/or cooling apparatus, at a temperature $T_i$, during a time $t_{i2P}$.

iii) A third optional phase during which the temperature of the nanoparticles decreases or is decreased, preferentially with cooling air or gas or the cooling apparatus, from an initial temperature $T_i$ to a final temperature $(T_f)_i$. In some other cases, $(T_f)_i$ is lower than $10^{50}$, $10^{20}$, $10^{10}$, $10^5$, $10^2$, 10, 5, 1, −10, −50, −100 or −200° C. The final temperature can be sufficiently low to avoid the melting or the destruction or the denaturation of the nanoparticles. In some cases, $(T_f)_i$ is lower than −200, −100, −50, −10, 0, 10, $10^2$, $10^3$, $10^5$ or $10^{10}$° C. The final temperature can be sufficiently low to avoid a too large temperature gradient. In some cases, the final temperature is comprised between −200 and $10^{10}$° C., preferentially between 0 and $10^3$° C., most preferentially between 10 and 100° C. In some cases, the temperature is decreased from $T_i$ to $(T_f)_i$ at a rate that is smaller than $10^{50}$, $10^{30}$, $10^{10}$, $10^5$, $10^3$, 10, 5, 2, 1, $10^{-1}$, $10^{-3}$, $10^{-5}$, $10^{-10}$ or $10^{-20}$° C. per minute. In some other cases, the temperature is decreased from $T_i$ to $(T_f)_i$ at a rate that is larger than $10^{-20}$, $10^{-10}$, $10^{-5}$, $10^{-3}$, $10^{-1}$, 1, 2, 5, 10, $10^3$, $10^5$, $10^{10}$, $10^{20}$ or $10^{50}$° C. per minute. In some cases, the time during which the temperature is decreased from $T_i$ to $(T_f)_i$, which is preferentially $t_{i3P}$, is larger than $10^{-50}$, $10^{-20}$, $10^{-10}$, $10^{-5}$, $10^{-3}$, $10^{-1}$, 1, 5, 10, $10^3$, $10^5$, $10^{10}$, $10^{30}$ or $10^{50}$ minute(s). In some other cases, the time during which the temperature is increased from $T_i$ to $(T_f)_i$, which is preferentially $t_{i3P}$, is lower than $10^{50}$, $10^{20}$, $10^{10}$, $10^5$, $10^3$, 10, 5, 1, $10^{-1}$, $10^{-3}$, $10^{-5}$ or $10^{-10}$ minute(s).

In some cases, $t_{i1P}=t_{ii}$, $t_{i2P}=t_i$ and/or $t_{i3P}=t_{if}$, where is preferentially equal to 1, 2, or 3.

In one embodiment of the invention, $T_i$ is larger than −200, −150, −100, −50, −20, −10, −5, 0, 5, 10, 20, 50, 100, 150, 200, 300, 500, 750, $10^3$, $10^5$, $10^{10}$, $10^{20}$ or $10^{50}$° C. In some cases, $T_i$ is sufficiently large to remove impurities that have at least one of the following properties: i) a large binding energy, preferentially a binding energy larger than $10^{-20}$, $10^{-10}$, $10^{-5}$, $10^{-3}$, $10^{-1}$, 1, 10, $10^3$, $10^5$ or $10^{10}$ eV or eV per nanoparticle or eV per nanoparticle per impurity or eV per bound between nanoparticle and impurity, ii) a localization at a large depth inside the nanoparticles, preferentially a localization inside the nanoparticles at a depth larger than 0.1, 0.5, 1, 5, 10 or 20 nm, iii) a large molecular weight, a molecular weight preferentially larger than $10^{-50}$, $10^{-20}$, $10^{-10}$, $10^{-5}$, $10^{-1}$, 1, 10, $10^3$, $10^5$, $10^{10}$, $10^{20}$ or $10^{50}$ kDa, iv) a large molar mass, a molar mass preferentially larger than $10^{-50}$, $10^{-20}$, $10^{-10}$, $10^{-5}$, $10^{-1}$, 1, 10, $10^3$, $10^5$, $10^{10}$, $10^{20}$ or $10^{50}$ gram per mol of impurity.

In another embodiment of the invention, $T_i$ is lower than $10^{50}$, $10^{20}$, $10^{10}$, $10^5$, $10^3$, 10, 5, 2, 1, 0, −5, −10, −50, −100, −150, −200, −250 or −270° C. In some cases, $T_i$ is sufficiently low to remove impurities that have at least one of the following properties: i) a low binding energy, preferentially a binding energy lower than $10^{20}$, $10^{10}$, $10^5$, $10^3$, 10, 1, $10^{-1}$, $10^{-3}$, $10^{-5}$ or $10^{-10}$ eV or eV per nanoparticle or eV per nanoparticle per impurity or eV per bound between nanoparticle and impurity, ii) a localization at a low or shallow depth inside the nanoparticles, preferentially a localization inside the nanoparticles at a depth lower than 0.1, 0.5, 1, 5, 10 or 20 nm, iii) a low molecular weight, a molecular weight preferentially lower than $10^{50}$, $10^{20}$, $10^{10}$, $10^5$, 10, 1, $10^{-1}$, $10^{-3}$, $10^{-5}$, $10^{-10}$, $10^{-20}$ or $10^{-50}$ kDa, iv) a low molar mass, a molar mass preferentially lower than $10^{50}$, $10^{20}$, $10^{10}$, $10^5$, 10, 1, $10^{-1}$, $10^{-3}$, $10^{-5}$, $10^{-1}$, $10^{-20}$ or $10^{-50}$ gram per mol of impurity.

In one embodiment of the invention, $T_i$ is comprised between 190 and 210, 150 and 250, 100 and 300, 50 and 350, 0 and 400, −50 and 450, −100 and 500, −150 and 550, −200 and 600 −250 and 650, 290 and 310, 250 and 350, 200 and 400, 150 and 450, 100 and 500, 50 and 550, 0 and 600, −50 and 650, −100 and 700, −150 and 750, −200 and 800, −250 and 850, 370 and 400, 350 and 450, 300 and 500, 200 and 600, 100 and 700, 0 and 800, −100 and 900, or between −200 and 1000° C.

In one embodiment of the invention, the difference between the heating temperature of the second phase of step i+1, $T_{i+1}$, and the heating temperature of the second phase of step i, $T_i$, which is equal to $T_{i+1}-T_i$, is lower than $10^{50}$, $10^{20}$, $10^{10}$, $10^5$, $10^3$, 10, 5, 2 or 1° C.

In another embodiment of the invention, the difference between the heating temperature of the second phase of step i+1, $T_{i+1}$, and the heating temperature of the second phase of step i, $T_i$, which is equal to $T_{i+1}-T_i$, is larger than $10_{-50}$, $10^{-20}$, $10^{-10}$, $10^{-5}$, $10^{-3}$, $10^{-1}$, 1, 5, 10, $10^2$, $10^3$, $10^5$ or $10^{10}$° C.

In one embodiment of the invention, $(T_i)_{maxHF}$ is the temperatures leading to or of the maximum heat flow, preferentially released or produced by the nanoparticles, during step i, preferentially during the second phase of step i.

In one embodiment of the invention, $(T_i)_{maxW}$ is the temperature leading to the maximum value of the derivative of the variation of mas or weight of the nanoparticles as a function of heating temperature, during step i, preferentially during the second phase of step i.

In one embodiment of the invention, $T_i$ is lower than $(T_i)_{maxHF}$ or $(T_i)_{maxW}$, preferentially by: i) a factor larger than 1.00001, 1.001, 1.1, 1.2, 1.5, 2, 5, 10, $10^3$ or $10^5$, or ii) by more than 0.001, 0.01, 0.1, 1, 5, 10, $10^2$, $10^3$ or $10^5$° C. In some cases, this temperature $T_i$ is $T_1$ or a temperature close to $T_1$ or a temperature that has a similar effect than $T_1$.

In one embodiment of the invention, $T_i$ is larger than $(T_i)_{maxHF}$ or $(T_i)_{maxW}$, preferentially by: i) a factor larger than 1.00001, 1.001, 1.1, 1.2, 1.5, 2, 5, 10, $10^3$ or $10^5$, or ii) by more than 0.001, 0.01, 0.1, 1, 5, 10, $10^2$, $10^3$ or $10^5$° C. In some cases, this temperature $T_1$ is $T_2$ or a temperature close to $T_2$ or a temperature that has a similar effect than $T_2$.

In one embodiment of the invention, $T_i$ is similar than $(T_i)_{maxHF}$ or $(T_i)_{maxW}$, preferentially differing from $(T_i)_{maxHF}$ or $(T_i)_{maxW}$ by: i) a factor lower than 1.00001, 1.001, 1.1, 1.2, 1.5, 2, 5, 10, $10^3$ or $10^5$, or ii) by a factor lower than 0.001, 0.01, 0.1, 1, 5, 10, $10^2$, $10^3$ or $10^5$° C. In some cases, this temperature $T_i$ is $T_3$ or a temperature close to $T_3$ or a temperature that has a similar effect than $T_3$.

In some cases, $T_i$ is a temperature, which is positioned relatively to the peaks of: i) heat flow as a function of temperature, ii) the variation in weight of the nanoparticles as a function of temperature, iii) the derivative as a function of temperature of the variation in weight of the nanoparticles as a function of temperature, which is such that all or most or more than $10^{-50}$, $10^{-30}$, $10^{-10}$, $10^{-5}$, $10^{-3}$, $10^{-1}$, 1, 5, 10, 50, 75, 90 or 99% of impurities are removed or released from the nanoparticles.

In one embodiment of the invention, $T_i$ varies, preferentially during the second phase of step i, by less than $10^{50}$, $10^{20}$, $10^{10}$, $10^5$, $10^3$, $10^2$, 50, 20, 10, 5, 2, 1, 10-1, $10^{-3}$ or $10^{-5}$%. A low percentage of temperature variation can be desired to remove a large quantity of impurity(ies) at the temperature $T_i$.

In another embodiment of the invention, $T_i$ varies by more than $10^{-50}$, $10^{-20}$, $10^{-10}$, $10^{-5}$, $10^{-3}$, $10^{-2}$, $10^{-1}$, 1, 5, 2, 1, 10, 20, 50, 75, 95, 100, $10^3$ or $10^5$%. A large percentage of temperature variation can be reached, for example when the nanoparticles produce chemical endothermic or exothermic reactions.

In some cases, the percentage of temperature variation can be: $(T_{i2Pmax}-T_{i2Pmin})/T_{iav}$, where $T_{i2Pmax}$, $T_{i2Pmin}$, and $T_{iav}$, are the maximum, minimum, and average temperatures reached during the second phase of step i.

In one embodiment of the invention, the temperature gradient of the first, second, and third phase of step i are designated as $\Delta T_{i1P}/(\delta t_{i1P})$, $\Delta T_{i2P}/(\delta t_{i2p})$, or $\Delta T_{i3P}/(\delta t_{i3P})$, where $\Delta T_{i1P}$ and $\delta t_{i1p}$ are the temperature variations and durations of the first phase of step i, $\Delta T_{i2P}$ and $\delta t_{i2P}$ are the temperature variations and durations of the second phase of step i, $\Delta T_{i3P}$ and $\delta t_{i3P}$ are the temperature variations and durations of the third phase of step i.

In one embodiment of the invention, the first and/or second and/or third phase(s) of step i last(s) for less than $10^{50}$, $10^{20}$, $10^{10}$, $10^{5}$, 10, 5, 1, $10^{-1}$, $10^{-2}$, $10^{-5}$, $10^{-10}$, $10^{-20}$ or $10^{-50}$ second(s) or minute(s) or hour(s). In some cases, the first and/or third phase is/are sufficiently short to create during this/these phase(s) a large temperature gradient. In some other cases, the first and/or third phase is/are sufficiently short when the nanoparticles need to be heated for a short time to reach the average temperature of the second phase or need to be cooled down for a short time to reach a sufficiently large temperature decrease from the average temperature of the second phase. In some other cases, the second phase is sufficiently short when the amount of impurity(ies) to be removed is low.

In another embodiment of the invention, the first and/or second and/or third phase(s) of step i last(s) for more than $10^{-50}$, $10^{-20}$, $10^{-10}$, $10^{-5}$, $10^{-1}$, 0, 1, 5, 10, $10^{2}$, $10^{5}$, $10^{10}$, $10^{20}$ or $10^{50}$ second(s) or minute(s) or hour(s). In some cases, the first and/or third phase is/are sufficiently long to avoid a too large temperature gradient during this/these phase(s). In some other cases, the first and/or third phase is/are sufficiently long when the nanoparticles need to be heated for a long time to reach the average temperature of the second phase or need to be cooled down for a long time to reach a sufficiently large temperature decrease from the average temperature of the second phase. In some other cases, the second phase is sufficiently long when the amount of impurity(ies) to be removed is large.

In another embodiment of the invention, the temperature gradient during the first and/or second and/or third phase of step i is/are lower than $10^{10}$, $10^{5}$, $10^{2}$, 50, 10, 5, 1, $10^{-1}$, $10^{-5}$, $10^{-10}$ or $10^{-50}$° C. per second or per minute or per hour. In some cases, the temperature gradient(s) of the first and/or second phase and/or third phase is/are sufficiently low to avoid the destruction, denaturation, degradation of the nanoparticles. In some cases, the temperature gradient(s) of the second phase is sufficiently low to enable that the temperature is maintained at an average temperature without too large fluctuations in temperatures.

In another embodiment of the invention, the temperature gradient during the first and/or second and/or third phase of step i is/are larger than $10^{-10}$, $10^{-5}$, $10^{-2}$, $10^{-1}$, 1, 5, 10, 50, $10^{2}$, $10^{5}$, $10^{10}$ or $10^{50}$° C. per second or per minute or per hour. In some cases, the temperature gradient of the first phase is sufficiently large to enable the nanoparticles to rapidly reach the average temperature of the second phase. In some other cases, the temperature gradient of the third phase is sufficiently large to enable the nanoparticles to rapidly decrease in temperature from the average temperature of the second phase. In still some other cases, the temperature gradient of the second phase is large, for example when the nanoparticles produce an exothermic or endothermic reaction.

In another embodiment of the invention, during step i, the temperature gradient is lower, preferentially by a factor of more than 1.0000001, 1.00001, 1.0001, 1.01, 1.1, 1.2, 1.5, 2, 5, 10, $10^{3}$, $10^{5}$, $10^{7}$ or $10^{9}$, or by a factor comprised between 1.000001 and $10^{9}$, 1.00001 and $10^{7}$, 1.0001 and $10^{5}$, 1.01 and $10^{3}$, 1.1 and $10^{3}$, 1.5 and $10^{3}$, 2 and $10^{3}$, 5 and $10^{3}$ or 5 and 100, during the second phase than during the first and/or third phase(s). In some cases, this situation occurs when the second phase maintains the temperature at some values without too many fluctuations; whereas the first and third phases induce larger temperature increase and temperature decrease, respectively.

In one embodiment of the invention, the average temperatures of the second phase, $T_i$, is determined by an instrument such as a TGA (thermogravimetry) and/or DTA (differential thermal analysis) and/or DSC (differential scanning calorimeter), which enables detecting the impurity(ies) that dissociate(s), disassemble(s), is/are removed from the nanoparticle(s) at $T_i$, preferentially via a combustion mechanism or through the capture by a gas of the impurity(ies).

In some cases, TGA, DTA, and/or DSC can be replaced by another instrument or apparatus that enables to measure at least one similar property of the nanoparticles that the TGA, DTA, and/or DSC.

In one embodiment of the invention, the temperature $T_i$ corresponds to or is the temperature at which the impurity(ies) dissociates, disassembles, is removed from the nanoparticles, wherein, preferentially:

i) The heavier impurities are dissociated, disassembled, or removed at the highest temperatures $T_i$ and/or the lightest chemical elements are dissociated, disassembled, or removed at the lowest temperatures $T_i$.

ii) The impurities bound to the nanoparticles with the largest binding energy are dissociated, disassembled, or removed at the highest temperatures $T_i$ and/or the impurities bound to the nanoparticles with the lowest binding energy are dissociated, disassembled, or removed at the lowest temperatures $T_i$.

iii) The impurities located at the largest depth inside the nanoparticles are dissociated, disassembled, or removed at the highest temperatures $T_i$ and/or the impurities located at the lowest depth inside the nanoparticles are dissociated, disassembled, or removed at the lowest temperatures $T_i$.

In one embodiment of the invention, the impurity(ies) is/are dissociated, disassembled, or removed from the nanoparticle(s) when: i) the distance between the impurity(ies) and the nanoparticle(s) increases, preferentially by a factor of more than 1.00001, 1.001, 1.1, 2, 5, 10, 50, $10^{2}$, $10^{3}$, $10^{5}$, $10^{10}$, $10^{20}$ or $10^{50}$, or above 0.001, 0.1, 1, 5, 10, $10^{3}$ or $10^{5}$ nm, between before and after dissociation, disassembling, or removal of the impurity(ies), ii) the presence of impurity(ies) in the nanoparticle(s) is detected before dissociation, disassembling, or removal of the impurity(ies), and is not detected after dissociation, disassembling, or removal of the impurity(ies), iii) a compound, preferentially a gas, liquid, or solid compound, carrying or comprising the impurity(ies), preferentially without the nanoparticle, is detected after dissociation, disassembling, or removal of the impurity(ies), and/or iv) the quantity of impurity per quantity, preferentially per mass or gram, of nanoparticle, varies, preferentially decreases, preferentially by a factor of more than 1.00001, 1.001, 1.1, 2, 5, 10, 50, $10^{2}$, $10^{3}$, $10^{5}$, $10^{10}$, $10^{20}$ or $10^{50}$, preferentially from a value above $10^{-20}$, $10^{-10}$, $10^{-5}$, $10^{-3}$, $10^{-1}$, 1, $10^{3}$, $10^{5}$, $10^{10}$, $10^{50}$ or $10^{100}$ μg of impurity(ies) per gram of nanoparticle(s) to a value below $10^{100}$, $10^{50}$, $10^{20}$, $10^{10}$, $10^{5}$, $10^{3}$, 10, 1, $10^{-1}$, $10^{-5}$, $10^{-10}$ or $10^{-100}$ μg of impurity(ies) per gram of nanoparticle(s), between before and after dissociation, disassembling, or removal of the impurity(ies).

The invention also relates to the method according to the invention, wherein the temperature $T_{iTmax}$ is determined, where $T_{iTmax}$ is the temperature of transformation of reagents, carbon, carbonaceous material, or impurity(ies), preferentially located at the surface of the nanoparticles, into products, or $CO_2$ gas, at which or for which: i) the maximum of energy is absorbed by the nanoparticle(s), ii) the maximum of energy is released by the nanoparticle(s), iii) the heat flow originating from the release of material or $CO_2$ from the nanoparticle(s) is maximal, or iv) the loss of mass of the nanoparticle(s) is larger than 1, 5, 10, 50, 75, 80, 90 or 95%. The percentage of loss in mass can in some cases be the ratio between the mass of the nanoparticles before heating the nanoparticles divided by the mass of the nanoparticles after heating the nanoparticles.

In one embodiment of the invention, the method according to the invention comprises a step of heating the nanoparticles at the temperature $T_i$, which has at least one of the following properties: i) it is lower than $T_{iTmax}$, ii) it is such that the slope of the variation of the heat flux as a function of temperature, $S_i$, is comprised between $10^{-6}$ and $10^{-3}$ W/g° C., iii) the derivative of the slope of the variation of the heat flux as a function of temperature, $\delta S_i/\delta T$, is positive, iv) it is maintained constant during the heating time $t_i$.

In one embodiment of the invention, the heating time $t_i$ is the duration of the second phase $t_{i2P}$.

In one embodiment of the invention, $S_i$ is lower than $10^{50}$, $10^{20}$, $10^{10}$, $10^5$, $10^3$, 10, 5, 1, $10^{-1}$, $10^{-3}$, $10^{-6}$, $10^{-9}$, $10^{-15}$ or $10^{-30}$ W/g° C.

In another embodiment of the invention, $S_i$ is larger than $10^{-50}$, $10^{-20}$, $10^{-10}$, $10^{-5}$, $10^{-2}$, $10^{-1}$, 1, 10, $10^3$ or $10^5$ W/g° C.

In still another embodiment of the invention, $S_i$ is between $10^{-50}$ and $10^{10}$, $10^{-50}$ and 10, $10^{-15}$ and 1, $10^{-9}$ and $10^{-1}$, or between $10^{-6}$ and $10^{-3}$ W/g° C.

The invention also relates to a method for removing at least one impurity from nanoparticles, comprising the following steps:

- During step 1, a thermal analysis of the nanoparticles is carried out, preferentially using a thermal analysis apparatus such as a TGA, a DTA, and/or a DSC. During this step, the temperature of the nanoparticles is increased from an initial temperature of the thermal analysis, $t_{iTA}$, up to a final temperature of the thermal analysis, $t_{fTA}$, at a rate $r_{TA}$. From this analysis, is deduced the at least one temperature, preferentially $T_i$, with at least one of the following properties: i) it is lower than the temperature $T_{fTA}$, preferentially 700° C., ii) it leads to a slope of the variation of the heat flow as a function of temperature, $S_i$, which is preferentially comprised between $10^{-6}$ and $10^{-3}$ W/g° C., iii) it leads to a derivative of the slope of the variation of the heat flux as a function of temperature, $\delta S_i/\delta T$, which is positive.
- During step 2, the temperature of the nanoparticles is increased up to the at least one temperature, preferentially $T_i$, and is maintained at $T_i$ during a heating time, preferentially $t_{i2P}$, preferentially comprised between 5 min and 24 hours.

In one embodiment of the invention, the thermal analysis includes a measurement of at least: i) the variation of the mass of the nanoparticles as a function of temperature, ii) the variation of the derivative of the mass of the nanoparticles as a function of temperature, iii) the variation of the heat flux of the nanoparticles as a function of temperature.

In one embodiment of the invention, $T_{iTA}$ is $T_{min-imp}$.

In another embodiment of the invention, $T_{fTA}$ is $T_{max-nano}$.

In another embodiment of the invention, $r_{TA}$ is lower than $10^5$, $10^4$, $10^3$, 500, 100, 50, 20, 10, 5, 2, 1, $10^{-1}$, $10^{-3}$ or $10^{-5}$° C. per minute. In some cases, a low value of $r_{TA}$ is desired when the release of the impurity(ies) from the nanoparticles and/or the monitoring of this release is/are achieved for low $r_{TA}$ values.

In another embodiment of the invention, $r_{TA}$ is larger than $10^{-5}$, $10^{-3}$, $10^{-1}$, 1, 2, 5, 10, $10^2$, $10^3$ or $10^5$° C. per minute. In some cases, a large value of $r_{TA}$ is desired when the release of the impurity(ies) from the nanoparticles and/or the monitoring of this release is/are achieved for large $r_{TA}$ values.

In one embodiment of the invention, $T_{iTA}$, and/or $T_{fTA}$, is/are larger than −250, −200, −150, −100, −50, −20, −10, 0, 5, 10, 50, 100, 200, 300, 500, 700, $10^3$ or $10^5$° C. In some cases, a large value of $T_{iTA}$ and/or $T_{fTA}$ is desired when the release of the impurity(ies) from the nanoparticles and/or the monitoring of this release is/are achieved for low values of $T_{iTA}$ and/or $T_{fTA}$.

In another embodiment of the invention, $T_{iTA}$ and/or $T_{fTA}$, is/are lower than $10^{50}$, $10^{20}$, $10^{10}$, $10^5$, $10^3$, $10^2$, 50, 20, 10, 5, 2, 1, 0, −10, −20, −50, −100, −200 or −250° C. In some cases, a low value of $T_{iTA}$ and/or $T_{fTA}$ is desired when the release of the impurity(ies) from the nanoparticles and/or the monitoring of this release is/are achieved for low values of $T_{iTA}$ and/or $T_{fTA}$.

In one embodiment of the invention, the percentage of impurity(ies) removed from the nanoparticles by the method is larger than $10^{-20}$, $10^{-10}$, $10^{-5}$, $10^{-2}$, $10^{-1}$, 1, 5, 10, 25, 50, 75, 80 or 90%. In some cases, this percentage is large when the method according to the invention is efficient or when the quantity of impurities can easily be removed from the nanoparticles, or when the binding energy of the impurity is lower $10^{50}$, $10^{20}$, $10^{10}$, $10^5$, $10^2$, 10, 5, 1, $10^{-1}$ or $10^{-5}$ eV, or when the impurity are located at a depth inside the nanoparticles that is lower than $10^3$, 100, 50, 20, 10, 5, 2, 1, 0.1 or 0.01 nm, or when the heating temperature(s) and/or heating time(s) used during the steps of the method enable to remove a large quantity of impurity.

In another embodiment of the invention, the percentage of impurity(ies) removed from the nanoparticles by the method is lower than 90, 80, 75, 50, 25, 10, 5, 1, $10^{-1}$, $10^{-2}$, $10^{-5}$, $10^{-10}$ or $10^{-20}$%. In some cases, this percentage is low when the method according to the invention is inefficient or when the quantity of impurities cannot easily be removed from the nanoparticles, or when the binding energy of the impurity is larger than $10^{-50}$, $10^{-20}$, $10^{-10}$, $10^{-5}$, $10^{-1}$, 1, 5, 10 or $10^5$ eV, or when the impurity are located at a depth inside the nanoparticles that is larger 0.001, 0.1, 1, 5, 10, 20, 50, $10^2$ or $10^3$ nm, or when the heating temperature(s) and/or heating time(s) used during the steps of the method do not enable to remove a large quantity of impurity.

In one embodiment of the invention, the percentage of impurity removed by the method is $Q_{IAT}/Q_{IBT}$ or $(Q_{IAT}-Q_{IBT})/Q_{IBT}$, where $Q_{IAT}$ is quantity, number, volume, mass, of impurity(ies) in the nanoparticles after the treatment of the nanoparticles by the method and $Q_{IBT}$ is the quantity, number, volume, mass, of impurity(ies) in the nanoparticles before the treatment of the nanoparticles by the method.

In another embodiment of the invention, the quantity of impurity(ies) removed from the nanoparticles by the method is larger than $10^{-50}$, $10^{-20}$, $10^{-10}$, $10^{-5}$, $10^{-1}$, 1, 5, 10, $10^3$, $10^5$, or $10^{10}$ μg of impurity(ies) per gram of nanoparticle(s).

In another embodiment of the invention, the quantity of impurity(ies) removed from the nanoparticles by the purifying step is lower than $10^{50}$, $10^{20}$, $10^{10}$, $10^{5}$, 10, 5, 1, $10^{-1}$, $10^{-3}$, $10^{-5}$, or $10^{-10}$ μg of impurity(ies) per gram of nanoparticle(s).

In another embodiment of the invention, impurity(ies) that are removed from the nanoparticles by the method possess at least one of the following property: i) a molecular weight larger than $10^{-50}$, $10^{-20}$, $10^{-10}$, $10^{-5}$, $10^{-3}$, $10^{-1}$, 1, 10, $10^{3}$, $10^{5}$, $10^{10}$, $10^{20}$, or $10^{50}$ kDa, ii) a molar mass larger than $10^{-50}$, $10^{-20}$, $10^{-10}$, $10^{-5}$, $10^{-3}$, $10^{-1}$, 1, 10, $10^{3}$, $10^{5}$, $10^{10}$, $10^{20}$, or $10^{50}$ gram of impurity per mol of impurity, iii) a size larger than $10^{-50}$, $10^{-20}$, $10^{-10}$, $10^{-5}$, $10^{-3}$, $10^{-1}$, 1, 10, $10^{3}$, $10^{5}$, $10^{10}$, $10^{20}$, or $10^{50}$ nm.

In another embodiment of the invention, impurity(ies) that are removed from the nanoparticles by the method according to the invention, possess at least one of the following property: i) a molecular weight lower than $10^{50}$, $10^{20}$, $10^{10}$, $10^{5}$, $10^{3}$, 10, 1, $10^{-1}$, $10^{-3}$, $10^{-5}$, $10^{-10}$, $10^{-20}$, or $10^{-50}$ kDa, ii) a molar mass lower than $10^{50}$, $10^{20}$, $10^{10}$, $10^{5}$, $10^{3}$, 10, 1, $10^{-1}$, $10^{-3}$, $10^{-5}$, $10^{-10}$, $10^{-20}$, or $10^{-50}$ gram of impurity per mol of impurity, iii) a size lower than $10^{50}$, $10^{20}$, $10^{10}$, $10^{5}$, $10^{3}$, 10, 1, $10^{-1}$, $10^{-3}$, $10^{-5}$, $10^{-10}$, $10^{-20}$ or $10^{-50}$ nm.

In another embodiment of the invention, the impurity(ies), which is/are preferentially removed by the method, possess(es) a binding energy with the nanoparticle(s) larger than $10^{-50}$, $10^{-20}$, $10^{-10}$, $10^{-5}$, $10^{-3}$, $10^{-1}$, 1, 5, 10, $10^{2}$, $10^{5}$, $10^{10}$, $10^{20}$ or $10^{50}$ eV or eV per nanoparticle or eV per nanoparticle per impurity or eV per bound between nanoparticle and impurity. In some cases, the binding energy can be large when the impurity is deeply inserted inside the nanoparticle, preferentially inserted at a depth larger than 0.001, 0.1, 1, 5, 10 or $10^{2}$ nm inside the nanoparticle, is comprised in the core of the nanoparticle, is comprised within the crystalline structure of the nanoparticle, is in strong interaction with the nanoparticle, or is in the nucleus of one chemical element of the nanoparticle.

In still another embodiment of the invention, the impurity(ies), which is/are preferentially removed by the method according to the invention, possess(es) a binding energy with the nanoparticle(s) lower than $10^{50}$, $10^{20}$, $10^{10}$, $10^{5}$, $10^{3}$, $10^{1}$, 1, 5, $10^{-1}$, $10^{-2}$, $10^{-5}$, $10^{-10}$, $10^{-20}$, or $10^{-50}$ eV or eV per nanoparticle or eV per nanoparticle per impurity or eV per bound between nanoparticle and impurity. In some cases, the binding energy can be low when the impurity is not deeply inserted inside the nanoparticle, preferentially inserted at a depth lower than $10^{2}$, 10, 5, 1, 0.1, or 0.001 nm inside the nanoparticle, is comprised in the coating of the nanoparticle, is not comprised in the crystalline structure of the nanoparticle, is in weak interaction with the nanoparticle, or is not in the nucleus of one chemical element of the nanoparticle.

In some cases, the binding energy of the impurity can be the minimum energy necessary to disassemble, remove, dissociate, and/or separate the impurity from the nanoparticle. It can be an atomic binding energy, the energy necessary to dissociate the chemical bound between the impurity and the nanoparticle, the nuclear binding energy.

In some cases, the binding energy is the binding energy between the nanoparticles and the impurities, preferentially the maximal, average, or minimal binding energy estimated over the whole assembly of nanoparticle(s) and/or impurity (ies).

In some cases, the binding energy is the energy necessary to detach, disassemble, desorb, or remove the impurity(ies) from the nanoparticle(s).

In one embodiment of the invention, the impurity(ies) is/are removed from the core and/or coating of the nanoparticles. In some cases, it/they are/is removed from a depth of at least $10^{-5}$, $10^{-3}$, $10^{-1}$, 1, 10 or $10^{2}$ nm inside the core and/or coating of the nanoparticles. In some other cases, it/they are/is removed from a depth of less than $10^{5}$, $10^{3}$, 10, 1, $10^{-1}$, $10^{-3}$, $10^{-5}$ nm inside the core and/or coating of the nanoparticles.

In one embodiment of the invention, the temperatures or temperature variations reached before, during, or after at least one step of the method are produced by a furnace or a heating apparatus, preferentially enabling to reach a temperature or temperature variation that is not produced or mainly produced by the nanoparticles.

In another apparatus of the invention, the temperatures or temperature variations reached before, during, or after at least one step of the method are produced by cooling air or gas or a cooling apparatus, preferentially enabling to reach a temperature or temperature variation that is not produced or mainly produced by the nanoparticles.

In another embodiment of the invention, the temperatures or temperature variations reached before, during, or after at least one step, are produced by the nanoparticles, preferentially through an exothermic or endothermic reaction of the nanoparticles.

The invention also relates to the method according to the invention, wherein the temperature of the nanoparticles is increased, preferentially during the first phase of step i, at a rate, preferentially $r_{i1P}$, that is comprised between $10^{-5}$ and $10^{5}$° C. per minute.

In one embodiment of the invention, the rate $r_{i1P}$ is comprised between $10^{-50}$ and $10^{10}$, $10^{-20}$ and $10^{5}$, $10^{-10}$ and $10^{3}$, $10^{-5}$ and 100, $10^{-2}$ and 50, $10^{-1}$ and 20, or between 1 and 10° C. per minute.

In one embodiment of the invention, $r_{i1P}$ is sufficiently large to avoid a stabilization of the furnace at a temperature that is different from $T_1$, $T_2$, and/or $T_3$, which could possibly modify the structure of the nanoparticles and/or possibly prevent the release of the impurity(ies) from the nanoparticles at $T_1$, $T_2$ and/or $T_3$.

In one embodiment of the invention, $r_{i1P}$ is sufficiently small to enable the stabilization of the furnace at $T_1$, $T_2$ and/or $T_3$.

The invention relates to the method according to the invention, wherein the heating time, $t_i$ (in minutes), is proportional to the quantity of heated nanoparticles, $Q_{nano}$ (in milligrams): $t_i = \alpha \cdot Q_{nano}$, where $\alpha$ is preferentially comprised between $10^{-5}$ and $10^{5}$.

In one embodiment of the invention, the heating time, $t_i$, is the duration of the second phase. This can be the case when the duration of the first and/or third phase(s) is/are small or smaller than the duration of the second phase or when the first and/or third phase are not responsible for the removal of the impurity(ies).

In another embodiment of the invention, the heating time, $t_i$, is the duration of the first and/or third phase(s). This can be the case when the duration of the second phase is small or smaller than the duration of the first and/or third phase(s) or when the second phase is not responsible for the removal of the impurity(ies).

In still another embodiment of the invention, the heating time, $t_i$, is the sum of the durations of the first and/or second and/or third phase.

In one embodiment of the invention, a is lower than $10^{50}$, $10^{20}$, $10^{10}$, $10^{5}$, $10^{3}$, 10, 5, 2, 1, $10^{-1}$, $10^{-5}$, $10^{-10}$ or $10^{-50}$.

In another embodiment of the invention, $\alpha$ is larger $10^{-50}$, $10^{-10}$, $10^{-5}$, $10^{-1}$, 1, 2, 5, 10, $10^{5}$, $10^{10}$, $10^{20}$ or $10^{50}$.

In still another embodiment of the invention a is comprised between $10^{-50}$ and $10^{50}$, $10^{-30}$ and $10^{30}$, $10^{-10}$ and $10^{10}$, $10^{-5}$ and $10^{5}$, $10^{-3}$ and $10^{3}$, $10^{-2}$ and 100, $10^{-2}$ and 10, $10^{-2}$ and 1, or between $10^{-1}$ and 1.

In one embodiment of the invention, the heating time increases, preferentially by: a factor of more than 1.000001, 1.001, 1.1, 1.2, 1.5, 2, 5, 10, $10^{3}$, $10^{5}$ or $10^{10}$ or above $10^{-50}$, $10^{-20}$, $10^{-10}$, $10^{-5}$, $10^{-3}$, 1, 5, 10, $10^{3}$, $10^{5}$, $10^{10}$, $10^{20}$ or $10^{50}$ minute(s), when the quantity of heated nanoparticles increases, preferentially by a factor of more than 1.000001, 1.001, 1.1, 1.2, 1.5, 2, 5, 10, $10^{3}$, $10^{5}$ or $10^{10}$ or above $10^{-50}$, $10^{-20}$, $10^{-10}$, $10^{-5}$, $10^{-3}$, 1, 5, 10, $10^{3}$, $10^{5}$, $10^{10}$, $10^{20}$ or $10^{50}$ gram of nanoparticles.

In one embodiment of the invention, the heating time increases, preferentially by: a factor of more than 1.000001, 1.001, 1.1, 1.2, 1.5, 2, 5, 10, $10^{3}$, $10^{5}$ or $10^{10}$ or above $10^{-50}$, $10^{-20}$, $10^{-10}$, $10^{-5}$, $10^{-3}$, 1, 5, 10, $10^{3}$, $10^{5}$, $10^{10}$, $10^{20}$ or $10^{50}$ minute(s), when the heating temperature increases, preferentially by a factor of more than 1.000001, 1.001, 1.1, 1.2, 1.5, 2, 5, 10, $10^{3}$, $10^{5}$ or $10^{10}$ or above $10^{-50}$, $10^{-20}$, $10^{-10}$, $10^{-5}$, $10^{-3}$, 1, 5, 10, $10^{3}$, $10^{5}$, $10^{10}$, $10^{20}$ or $10^{50}$° C.

In still another embodiment of the invention, the heating time increases, preferentially by: a factor of more than 1.000001, 1.001, 1.1, 1.2, 1.5, 2, 5, 10, $10^{3}$, $10^{5}$ or $10^{10}$ or above $10^{-50}$, $10^{-20}$, $10^{-10}$, $10^{-5}$, $10^{-3}$, 1, 5, 10, $10^{3}$, $10^{5}$, $10^{10}$, $10^{20}$ or $10^{50}$ minute(s), when the heating temperature decreases, preferentially by a factor of more than 1.000001, 1.001, 1.1, 1.2, 1.5, 2, 5, 10, $10^{3}$, $10^{5}$ or $10^{10}$ or below $10^{50}$, $10^{20}$, $10^{10}$, $10^{5}$, $10^{3}$, 5, 1, $10^{-3}$, $10^{-5}$, $10^{-10}$, $10^{-20}$ or $10^{-50}$° C.

The invention also relates to the method according to the invention, wherein the duration of temperature increase to reach $T_1$, $T_2$, or $T_3$, is decreased by reducing the percentage of humidity of the nanoparticles.

In one embodiment of the invention, the duration of temperature increases to reach $T_i$, $T_1$, $T_2$, or $T_3$, preferentially $t_{i1P}$, increases, preferentially by a factor of more than 1.00001, 1.001, 1.1, 1.2, 1.5, 2, 5, 10, $10^{3}$, $10^{5}$ or $10^{10}$ or above $10^{-50}$, $10^{-20}$, $10^{-10}$, $10^{-5}$, $10^{-3}$, $10^{-1}$, 1, 10, $10^{3}$, $10^{5}$ or $10^{10}$ minute(s) or from a value that is below $10^{-50}$, $10^{-20}$, $10^{-10}$, $10^{-5}$, $10^{-3}$, $10^{-1}$, 1, 10, $10^{3}$, $10^{5}$ or $10^{10}$ minute(s) to a value that is above $10^{-50}$, $10^{-20}$, $10^{-10}$, $10^{-5}$, $10^{-3}$, $10^{-1}$, 1, 10, $10^{3}$, $10^{5}$ or $10^{10}$ minute(s), preferentially when the percentage of humidity in the nanoparticles is larger than or increases above $10^{-50}$, $10^{-20}$, $10^{-10}$, $10^{-5}$, $10^{-1}$, 1, 5, 10, 25, 50, 75, 80, 99, 99.9 or 100%.

In one embodiment of the invention, the duration of temperature increase to reach $T_i$, $T_1$, $T_2$, or $T_3$, preferentially $t_{i1P}$, decreases, preferentially by a factor of more than 1.00001, 1.001, 1.1, 1.2, 1.5, 2, 5, 10, $10^{3}$, $10^{5}$ or $10^{10}$ or below $10^{50}$, $10^{20}$, $10^{10}$, $10^{5}$, $10^{3}$, 10, 1, $10^{-1}$, $10^{-3}$, $10^{-5}$ or $10^{-10}$ minute(s) or from a value $t_i$ that is above $10^{-50}$, $10^{-20}$, $10^{-10}$, $10^{-5}$, $10^{-3}$, $10^{-1}$, 1, 10, $10^{3}$, $10^{5}$ or $10^{10}$ minute(s) to a value that is below $10^{50}$, $10^{20}$, $10^{10}$, $10^{5}$, $10^{3}$, 10, 1, $10^{-1}$, $10^{-3}$, $10^{-5}$ or $10^{-10}$ minute(s), preferentially when the percentage of humidity in the nanoparticles decreases below 100, 99, 80, 70, 50, 20, 10, 5, 2, 1 or $10^{-5}$, $10^{-1}$ or $10^{-5}$%.

In some cases, the duration of temperature increases to reach $T_i$, $T_1$, $T_2$, or $T_3$ increases(s) or is large when the percentage of humidity in the nanoparticles increases or is large. In some other cases, the duration of temperature increases to reach $T_i$, $T_1$, $T_2$, or $T_3$ decreases or is low when the percentage of humidity in the nanoparticles decreases or is low.

In one embodiment of the invention, the percentage of humidity in the nanoparticles is larger than or increases above $10^{-50}$, $10^{-20}$, $10^{-10}$, $10^{-5}$, $10^{-1}$, 1, 5, 10, 25, 50, 75, 80, 99, 99.9 or 100%. In some cases, this situation can occur, preferentially before the treatment of the nanoparticles by the method, preferentially when the nanoparticles are not lyophilized or when the aqueous medium in which the nanoparticles are suspended or comprised is not removed.

In one embodiment of the invention, the percentage of humidity in the nanoparticles is lower than or decreases below 100, 99.9, 99, 80, 75, 50, 25, 10, 5, 1, $10^{-1}$, $10^{-5}$, $10^{-10}$, $10^{-20}$ or $10^{-50}$%. In some cases, this situation can occur, preferentially before the treatment of the nanoparticles by the method, preferentially when the nanoparticles are lyophilized or when the aqueous medium in which the nanoparticles are suspended or comprised is removed. In some other cases, this situation can occur, preferentially after or during the treatment of the nanoparticles by the method, preferentially when the heat treatment removes water from the nanoparticles.

In one embodiment of the invention, the percentage of humidity of the nanoparticles, which could also be designated as relative humidity (RH) in some cases, is the ratio between the partial pressure of water vapor, preferentially of the nanoparticles or of the medium or environment surrounding the nanoparticles, and the equilibrium vapor pressure of water, preferentially of the nanoparticles or of the medium or environment surrounding the nanoparticles, at a given temperature, preferentially before, during, or after the treatment of the nanoparticles by the method, preferentially of the nanoparticles or of the medium or environment surrounding the nanoparticles.

The invention also relates to the method according to the invention, resulting in a percentage in mass of carbon or carbonaceous material in the nanoparticles, which is below 0.4%.

In one embodiment of the invention, the percentage in mass of carbon or carbonaceous material is lower than 100, 90, 80, 70, 60, 50, 30, 20, 10, 5, 2, 1, $10^{-2}$, $10^{-5}$ or $10^{-10}$%. In some cases, this situation occurs before the treatment of the nanoparticles by the method. In some other cases, this situation occurs during the treatment of the nanoparticles by the method. In still some other cases, this situation occurs after the treatment of the nanoparticles by the method.

In another embodiment of the invention, the percentage in mass of carbon or carbonaceous material is larger than $10^{-10}$, $10^{-5}$, $10^{-2}$, 1, 2, 5, 10, 20, 30, 50, 70, 80, 90, 95 or 99%. In some cases, this situation occurs before the treatment of the nanoparticles by the method. In some other cases, this situation occurs during the treatment of the nanoparticles by the method. In still some other cases, this situation occurs after the treatment of the nanoparticles by the method.

In one embodiment of the invention, the heating time, preferentially $t_i$, most preferentially $t_{i2P}$, is increased or set at a value, preferentially above $10^{-100}$, $10^{-50}$, $10^{-20}$, $10^{-10}$, $10^{-5}$, $10^{-2}$, $10^{-1}$, 1, 5, 10, $10^{2}$, $10^{5}$, $10^{10}$, $10^{20}$ or $10^{50}$ hour(s), until or so that the percentage in mass of carbon or carbonaceous material in the nanoparticle(s) is lower than 99, 90, 70, 50, 30, 20, 10, 5, 2, 1, 0.1, 0.001 or 0.0001%. In some cases, this situation can occur, preferentially when it is necessary to increase the heating time or to reach a large heating time to remove a large quantity of impurity(ies) from the nanoparticle(s).

In one embodiment of the invention, the heating temperature, preferentially $T_i$ or $T_{i2P}$, is increased or set at a value, preferentially above −273, −250, −200, −200, −100, 0, 5, 10, 50, 100, 200, 300, 400, 500, $10^{3}$, $10^{5}$ or $10^{9}$° C., until or so that the percentage in mass of carbon or carbonaceous material in the nanoparticle(s) is lower than 99, 90, 70, 50, 30, 20, 10, 5, 2, 1, 0.1, 0.001 or 0.0001%.

In one embodiment of the invention, the heating time, preferentially $t_i$, most preferentially $t_{i2P}$, is decreased or set at a value, preferentially below $10^{100}$, $10^{50}$, $10^{20}$, $10^{10}$, $10^5$, $10^2$, 10, 1, $10^{-1}$, $10^{-2}$, $10^{-5}$, $10^{-20}$, or $10^{-50}$ hour(s), until or so that the percentage in mass of carbon or carbonaceous material in the nanoparticle(s) is lower than 99, 90, 70, 50, 30, 20, 10, 5, 2, 1, 0.1, 0.001 or 0.0001%. In some cases, this situation can occur, preferentially when a too large heating time can destroy or denature the nanoparticles.

In one embodiment of the invention, the heating temperature, preferentially $T_i$ or $T_{i2P}$, is decreased or set at a value, preferentially below $10^9$, $10^5$, $10^3$, 500, 250, 100, 50, 30, 20, 10, 5, 1, −10, −20, −50, −100, −150, −200, −250 or −273° C., until or so that the percentage in mass of carbon or carbonaceous material in the nanoparticle(s) is lower than 99, 90, 70, 50, 30, 20, 10, 5, 2, 1, 0.1, 0.001 or 0.0001%.

In one embodiment of the invention, carbonaceous material is non-denatured carbonaceous material, for example non-denatured organic material, DNA, RNA, protein, lipid or enzyme. In some cases, non-denatured material is material that has not lost its primary, secondary, tertiary, and/or quaternary structure. In some cases, non-denatured material is material that has not lost its activity or function or some of its activity or function.

In one embodiment of the invention, carbonaceous material is denatured carbonaceous material, for example denatured organic material, DNA, RNA, protein, lipid or enzyme. In some cases, denatured material is material that has lost its primary, secondary, tertiary, and/or quaternary structure. In some cases, denatured material is material that has not lost its activity or function or some of its activity or function.

In one embodiment of the invention, carbonaceous material is material that comprises a percentage in mass of carbon larger than $10^{-50}$, $10^{-20}$, $10^{-10}$, $10^{-5}$, $10^{-1}$, 1, 5, 10, 50, 75, 80, 90, 99 or 100%.

In one embodiment of the invention, carbonaceous material is material that comprises a percentage in mass of carbon lower than 100, 99, 90, 80, 70, 50, 20, 10, 5, 2, 1, $10^{-1}$, $10^{-3}$, $10^{-5}$ or $10^{-10}$%.

The invention also relates to the method according to the invention, wherein the heating time $t_i$ is set at a value that yields a percentage in mass of impurity(ies) in the nanoparticle(s), which is below 0.4%, preferentially following step i.

In one embodiment of the invention, when the percentage in mass of impurity(ies) in the nanoparticle(s) is lower than 0.4%, it is possible to add a surrounding coating to the nanoparticles and/or to stabilize the nanoparticles and/or to avoid nanoparticle aggregation.

In another embodiment of the invention, when the percentage in mass of impurity(ies) in the nanoparticles is larger than 0.4%, it is not possible to add a surrounding coating to the nanoparticles and/or to stabilize the nanoparticles and/or to avoid nanoparticle aggregation.

In one embodiment of the invention, the heating time, preferentially $t_i$, most preferentially $t_{i2P}$, is increased, preferentially above $10^{-100}$, $10^{-50}$, $10^{-20}$, $10^{-10}$, $10^{-5}$, $10^{-2}$, $10^{-1}$, 1, 5, 10, $10^2$, $10^5$, $10^{10}$, $10^{20}$ or $10^{50}$ hours, until the percentage in mass of impurity(ies) in the nanoparticle(s) is lower than 99, 90, 70, 50, 30, 20, 10, 5, 2, 1, 0.1, 0.001 or 0.0001%.

In one embodiment of the invention, the heating time, preferentially $t_i$, most preferentially $t_{i2P}$, is decreased or set at a value, preferentially below $10^{100}$, $10^{50}$, $10^{20}$, $10^{10}$, $10^5$, $10^2$, 10, 1, $10^{-1}$, $10^{-2}$, $10^{-5}$, $10^{-20}$, or $10^{-50}$ hour(s), until the percentage in mass of impurity(ies) in the nanoparticle(s) is above $10^{-50}$, $10^{-20}$, $10^{-5}$, $10^{-3}$, $10^{-2}$, $10^{-1}$, 1, 5, 10, 50 or 75%.

The invention also relates to the method according to the invention, wherein more than 50% of impurities are removed from the nanoparticles, where this percentage is based on the ratio $Q_{AP}/Q_{BP}$, where $Q_{AP}$ and $Q_{BP}$ are the quantity of impurity in the nanoparticle after and before the treatment of the nanoparticles by the method, respectively.

In one embodiment of the invention, $Q_{AP}/Q_{BP}$ is lower than $10^{50}$, $10^{20}$, $10^{10}$, $10^5$, $10^3$, 100, 50, 20, 10, 5, 2, 1, $10^{-1}$, $10^{-5}$, $10^{-10}$ or $10^{-20}$%.

In another embodiment of the invention, $Q_{AP}/Q_{BP}$ is larger than $10^{-50}$, $10^{-20}$, $10^{-10}$, $10^{-5}$, $10^{-3}$, $10^{-1}$, 1, 5, 10, 50, 100, $10^5$, $10^{10}$ or $10^{20}$%.

In some cases, $Q_{AP}/Q_{BP}$ can be larger than 1, for example if the method does not successfully remove impurity(ies) from the nanoparticles and/or impurity(ies) are captures by or inserted in the nanoparticles during the treatment by the method, for example when the chemicals used in the method comprise impurity(ies) that become adsorbed at the surface of the nanoparticles during the treatment.

In some other cases, $Q_{AP}/Q_{BP}$ can be lower than 1, for example when the method successfully removes the impurity(ies) from the nanoparticles.

In one embodiment of the invention, the heating time $t_i$ is, is increased, or is set at a value, preferentially above $10^{-100}$, $10^{-50}$, $10^{-20}$, $10^{-10}$, $10^{-5}$, $10^{-2}$, $10^{-1}$, 1, 5, 10, $10^2$, $10^5$, $10^{10}$, $10^{20}$ or $10^{50}$ hour(s), until or so that $Q_{AP}/Q_{BP}$ is lower than 99, 90, 70, 50, 30, 20, 10, 5, 2, 1, 0.1, 0.001 or 0.0001%.

The invention also relates to the method, preferentially purifying method, according to the invention, wherein more than 90% in mass of carbon or carbonaceous material is removed from the nanoparticles, where this percentage is based on the ratio (% $C_{AT}$−% $C_{BT}$)/% $C_{BT}$, where % $C_{AT}$ and % $C_{BT}$ are the percentages of carbon or carbonaceous material after and before treating the nanoparticles with the method, respectively.

In some cases, (% $C_{AT}$−% $C_{BT}$)/% $C_{BT}$ is larger than $10^{-50}$, $10^{-20}$, $10^{-5}$, $10^{-2}$, $10^{-1}$, 1, 5, 10, 50, 75, 90, 95 or 99%. This can be the case when the method, preferentially purifying method, is efficient or when the quantity of carbon or carbonaceous material comprised in the nanoparticle before the treatment of the nanoparticles with the method is lower than a certain threshold, preferentially lower than 99, 90, 70, 60, 50, 40, 30, 20, 10 or 1%.

In some other cases, (% $C_{AT}$−% $C_{BT}$)/% $C_{BT}$ is lower than 99, 90, 70, 60, 50, 40, 30, 20, 10 or 1%. This can be the case when the purifying method is not efficient or when the quantity of carbon or carbonaceous material comprised in the nanoparticle before the treatment of the nanoparticles with the method is larger than a certain threshold, preferentially larger than 99, 90, 70, 60, 50, 40, 30, 20, 10 or 1%.

In still some other cases, (% $C_{AT}$−% $C_{BT}$)/% $C_{BT}$ is between 0.1 and 100, 1 and 99, 10 and 99, 50 and 99, or between 80 and 99%.

In one embodiment of the invention, the heating temperature, preferentially $T_{iav}$, is, is increased, or is set at a value, preferentially above −250, −200, −150, −100, −50, 0, 10, 50, 100, 150, 200, 250, 300, 350, 400, 450, 500, 550, 600, 650, 700, $10^3$, $10^4$ or $10^{6°}$ C., until or so that $Q_{AP}/Q_{BP}$ is lower than 99, 90, 70, 50, 30, 20, 10, 5, 2, 1, 0.1, 0.001 or 0.0001%.

In some cases, the heating time and/or heating temperature is/are increased to remove impurity(ies) from the nanoparticles, for example when impurity(ies) is/are released from the nanoparticles at high temperatures or for large heating time.

In one embodiment of the invention, the heating time $t_i$ is, is decreased, or is set at a value, preferentially below $10^{100}$, $10^{50}$, $10^{20}$, $10^{10}$, $10^5$, $10^2$, 10, 1, $10^{-1}$, $10^{-2}$, $10^{-5}$, $10^{-20}$, or $10^{-50}$ hour(s), until $Q_{AP}/Q_{MP}$ or so that is larger than $10^{-50}$, $10^{-20}$, $10^{-5}$, $10^{-3}$, $10^{-2}$, $10^{-1}$, 1, 5, 10, 50 or 75%.

In one embodiment of the invention, the heating temperature, preferentially $T_i$ or $T_{iav}$, is, is decreased, or is set at a value, preferentially below $10^6$, $10^4$, $10^3$, 700, 650, 600, 550, 500, 450, 400, 350, 300, 250, 200, 150, 100, 50, 10, 0, −50, −100, −150, −200 or −250° C., preferentially until $Q_{AP}/Q_{BP}$ or so that is larger than $10^{-50}$, $10^{-20}$, $10^{-5}$, $10^{-3}$, $10^{-2}$, $10^{-1}$, 1, 5, 10, 50 or 75%.

In some cases, the heating temperature and/or heating time is/are decreased or kept below a certain threshold to remove impurity(ies), for example when impurity(ies) is/are removed from nanoparticles at low temperatures.

In some other cases, the heating temperature and/or heating time is/are decreased or kept below a certain threshold to avoid the destruction, denaturation, or oxidation, preferentially a change in oxidation state, of the nanoparticles.

The invention also relates to the method according to the invention, wherein at least one step or one phase of step i of the method is carried out in the presence of oxygen.

In some cases, oxygen can be a gas comprising oxygen or $O_2$.

The invention also relates to the method according to the invention, wherein at least one step or one phase of step i of the method is carried out in the presence of a carrying gas or $CO_2$.

In one embodiment of the invention, the carrying gas can be $CO_2$ or a gas that carries the impurity(ies), carbon, or carbonaceous material. In some cases, the carrying gas or $CO_2$ carries or removes more than $10^{-50}$, $10^{-20}$, $10^{-5}$, $10^{-3}$, $10^{-1}$, 1, 5, 10, 25, 50, 75, 80, 90, 99 or 100% of impurity (ies), carbon, or carbonaceous material. In some cases, this situation can occur when the time and/or temperature of heating is/are such that it/they enable to remove a lot of impurity(ies) using the carrying gas. In some other cases, the carrying gas or $CO_2$ carries less than 100, 99, 90, 80, 75, 50, 25, 10, 5, 1, $10^{-1}$, $10^{-3}$, $10^{-5}$, $10^{-20}$ or $10^{-50}$° % of impurity(ies), carbon, or carbonaceous material. In some cases, this situation can occur when the time and/or temperature of heating is/are such that it/they does/do not enable to remove a lot of impurity(ies) using the carrying gas. In some cases, the carrying gas or $CO_2$ carries or removes the impurity(ies) during the second phase of step i, or carries or removes more impurity, preferentially by a factor of more than 1.000001, 1.0001, 1.1, 1.2, 1.5, 2, 5, 10, 50, $10^2$, $10^3$ or $10^5$, during the second phase of step i than during the first or third phase of step i.

In one embodiment of the invention, the method, preferentially the second phase of step i, is a combustion, preferentially when the carrying gas or $CO_2$ is involved in or is responsible for or leads to the removal of the impurity(ies) from the nanoparticles.

In one embodiment of the invention, the carrying gas is air or is a gas comprising a percentage in oxygen or $O_2$ larger than $10^{-100}$, $10^{-50}$, $10^{-10}$, $10^{-5}$, $10^{-2}$, $10^{-1}$, 1, 5, 10, 20, 50, or 75%.

In one embodiment of the invention, the percentage of $O_2$ in the carrying gas is increased or is sufficiently large to enable the combustion or transformation of the carbonaceous material, preferentially comprised in or at the surface of the nanoparticles, to occur.

In one embodiment, the carrying gas comprises a percentage in oxygen or $O_2$ lower than 99.9, 99, 70, 50, 20, 10, 5, 2, or 1%.

In one embodiment of the invention, the percentage of $O_2$ in the carrying gas is decreased or is sufficiently low to prevent the oxidation of the nanoparticles, or to prevent a change of oxidation state of the nanoparticles.

In one embodiment of the invention, the method according to the invention does not oxidize or does not change the oxidation state of the nanoparticles.

In one embodiment of the invention, the change in the oxidation state of the nanoparticle is a change that results in the loss of magnetic properties from the nanoparticles, for example a change from maghemite or magnetite to hematite.

In one embodiment of the invention, the carrying gas comprises a percentage in Oxygen comprised between $10^{-20}$ and 100%, $10^{-10}$ and 99, $10^{-5}$ and 90, $10^{-1}$ and 80, 1 and 70, or between 10 and 50% of $O_2$.

In one embodiment of the invention, the carrying gas comprises less than 99, 90, 80, 70, 50, 20, 10, 5, 2 or 1% of noble gas. In some cases, a too large percentage of noble gas is avoided since it could prevent the removal of impurity(ies) from the nanoparticles.

In another embodiment of the invention, the carrying gas comprises more than 1, 2, 5, 10, 20, 50, 70, 80, 90 or 99% of noble gas. In some cases, a significant percentage of noble gas, preferentially mixed with $O_2$, is desired, for example to avoid that $O_2$ is inflammable.

In one embodiment of the invention, the percentage of a gas is the percentage by volume of this gas, preferentially when this gas is dry.

In one embodiment of the invention, the quantity of impurity that is removed can be increased, preferentially by a factor of more than factor of more than 1.00001, 1.001, 1.1, 2, 5, 10, 50, $10^2$, $10^3$, $10^5$, $10^{10}$, $10^{20}$ or $10^{50}$, when the percentage of $O_2$ in the carrying gas is increased, preferentially by a factor of more than 1.00001, 1.001, 1.1, 2, 5, 10, 50, $10^2$, $10^3$, $10^5$, $10^{10}$, $10^{20}$, or $10^{50}$.

In one embodiment of the invention, the quantity of impurity that is removed can be decreased, preferentially by a factor of more than factor of more than 1.00001, 1.001, 1.1, 2, 5, 10, 50, $10^2$, $10^3$, $10^5$, $10^{10}$, $10^{20}$, or $10^{50}$, when the percentage of $O_2$ in the carrying gas is decreased, preferentially by a factor of more than 1.00001, 1.001, 1.1, 2, 5, 10, 50, $10^2$, $10^3$, $10^5$, $10^{10}$, $10^{20}$, or $10^{50}$.

In one embodiment of the invention, the first and/or third phase, is/are carried out in the presence of a gas with a lower concentration in $O_2$, preferentially by a factor of more than 1.00001, 1.001, 1.1, 2, 5, 10, 50, $10^2$, $10^3$, $10^5$, $10^{10}$, $10^{20}$, or $10^{50}$, than during the second phase, to prevent the removal of impurity(ies) during the first and/or third phase, or to remove less impurity(ies), preferentially by a factor of more than 1.00001, 1.001, 1.1, 2, 5, 10, 50, $10^2$, $10^3$, $10^5$, $10^{10}$, $10^{20}$, or $10^{50}$ during the first and/or third phase(s) than during the second phase.

The invention also relates to the method according to the invention, wherein the impurities removed from the nanoparticles are located at a depth of less than 100 nm inside the nanoparticles.

In one embodiment of the invention, the impurity(ies) is/are located at a certain depth in the nanoparticle, which is larger than 0.01, 0.1, 1, 5, 10, 25, 50, or 75% of the diameter or largest dimension of the nanoparticle.

In another embodiment of the invention, the impurity(ies) is/are located at a certain depth in the nanoparticle, which is lower than 75, 50, 25, 10, 5, 1, 0.1 or 0.01% of the diameter or largest dimension of the nanoparticle.

According to the invention, this percentage can be the ratio between the depth at which the impurity is located in the nanoparticle and the diameter or largest dimension of the nanoparticle.

In one embodiment of the invention, the impurity(ies) is/are located at a certain depth in the nanoparticles, which is larger than 0.01, 0.1, 0.5, 1, 5, 10, 15 or 20 nm.

In another embodiment of the invention, the impurity(ies) is/are located at a certain depth in the nanoparticles, which is lower than 100, 50, 20, 5, 2, 1 or 0.1 nm.

In some cases, deep impurity(ies) can be located inside the core, preferentially the crystal of the core, of the nanoparticles.

In some cases, shallow impurity(ies) can be located in the coating of the nanoparticles.

In another embodiment of the invention, the impurity(ies) is/are located at a certain depth in the nanoparticles, which is comprised between 0.01 and $10^3$, 0.1 and 500, 0.1 and 100, 0.1 and 50, 0.1 and 20, 0.1 and 10, or between 0.1 and 5 nm.

In some cases, the depth in the nanoparticles is the distance, preferentially measured, from the external surface of the nanoparticles to the location of the impurity(ies) in the nanoparticles.

The invention also relates to the method according to the invention, wherein the heating temperature and/or heating time is/are determined by measuring the temperature at which the at least one impurity is removed from the nanoparticles.

In another embodiment of the invention, an apparatus such as TGA (Thermogravimetry analysis) is used to determine the temperature, preferentially $T_{iav}$, and/or heating time, preferentially $t_i$, that can remove the impurity(ies) from the nanoparticle(s).

The invention also relates to the method according to the invention, wherein the at least one impurity consists of or comprises or originates from carbon or carbonaceous material.

In one embodiment of the invention, the carbonaceous material is removed by the carrying gas or $CO_2$ gas.

The invention also relates to the method according to the invention, wherein the at least one impurity consists of or comprises or originates from a cell, preferentially the cell synthetizing the nanoparticles.

In one embodiment of the invention, the cells synthetizing the nanoparticles are nanoparticle-producing cells.

In one embodiment of the invention, the at least one impurity is or comprises or originates from the medium or environment surrounding the nanoparticles.

In one embodiment of the invention, the at least one impurity is or comprises or originates from endotoxins or lypopolysaccharides.

In one embodiment of the invention, the at least one impurity is or comprises or originates from the chemicals or chemical elements used to produce the nanoparticles.

The invention also relates to the method according to the invention, wherein the at least one impurity is selected from the group consisting of compounds, which are or consist of or comprise or originate from: aldehydes, acid anhydrides, acyl halides, aliphatic amine polymer, amidines, alcohols, amides, amines, carboxylic acids, cell, CMR agents, cyclic molecules, cytotoxic molecules, endotoxins, esters, ethers, fatty acid, hydroperoxides, imines, ketones, lipids, lipopolysaccharides, macromolecules, nanoparticle coating, nitriles, organic solvents, organic material, peroxides, phenols, phosphates, phospholipids, phosphoric acids, polysaccharide, sulfides, sulfonic acids, sugars, polymers, polymers of amino acids, polymeric or non-polymeric silica, solvents, thiols, and derivatives, acidic, basic, or neutral derivatives, positively, negatively, or neutrally charged derivatives, or component, of at least one of these compounds.

The invention also relates to high purity nanoparticle(s) obtained by the method according to the invention.

The invention also relates to high purity nanoparticle(s) or high purity nanoparticles that are not obtained by the method.

In one embodiment of the invention, the high purity nanoparticles are the nanoparticles treated by the method.

In one embodiment of the invention, high purity nanoparticles are nanoparticles that comprise less than $10^{50}$, $10^{30}$, $10^{20}$, $10^{10}$, $10^5$, $10^3$, 10, 5, 2, 1, $10^{-1}$, $10^{-3}$, $10^{-5}$, $10^{-10}$ μg of impurity(ies) per gram of nanoparticles.

In one embodiment of the invention, high purity nanoparticles are nanoparticles that comprise a percentage in mass of impurity than is lower 100, 90, 80, 70, 50, 20, 10, 5, 2, 1, 0.1 or 0.001%. In some cases, the percentage in mass of impurity in the nanoparticles can be the ratio between the mass of the impurity(ies) in the nanoparticles and the mass of the nanoparticles.

The invention also relates to the high purity nanoparticle(s) according to the invention, comprising: i) at least 0.8 g or between 0.8 g and 0.99999999999 g of iron oxide per gram of nanoparticle or per gram of nanoparticle core, ii) optionally a doping material at a concentration comprised between 0.5 and 0.8 g of doping material per gram of nanoparticle, and iii) impurities that are different from iron, oxygen, and the doping material, at a concentration, which is lower than 0.5 g per gram of nanoparticle or per gram of nanoparticle coating or which is comprised between $10^{-9}$ g and 0.5 g of impurities per gram of nanoparticle or per gram of nanoparticle coating.

The invention also relates to the high purity nanoparticle(s) according to the invention, wherein: i) at least 0.8 g or between 0.8 g and 0.99999999999 g of iron oxide per gram of nanoparticle are comprised in the nanoparticle core, ii) optionally a doping material at a concentration comprised between 0.5 and 0.8 g of doping material per gram of nanoparticle is comprised in the core and/or coating of the nanoparticles, iii) impurities that are different from iron, oxygen, and the doping material, are comprised in the coating of the nanoparticles at a concentration, which is lower than 0.5 g per gram of nanoparticles or which is comprised between $10^{-9}$ g and 0.5 g of impurities per gram of nanoparticles or coating.

In one embodiment of the invention, the high purity nanoparticles, preferentially the cores of the high purity nanoparticles, comprise more than $10^{-50}$, $10^{-30}$, $10^{-20}$, $10^{-10}$, $10^{-5}$, $10^{-3}$, 0.1, 0.2, 0.3, 0.4, 0.5, 0.7, 0.8, 0.9, 0.99, 0.999 or 0.9999999999 g of iron oxide per gram of nanoparticles or nanoparticle cores.

In another embodiment of the invention, the high purity nanoparticles, preferentially the cores of the high purity nanoparticles, comprise less than 0.9999999999, 0.999, 0.99, 0.9, 0.8, 0.7, 0.5, 0.3, 0.2, 0.1, $10^{-3}$, $10^{-5}$, $10^{-10}$ or $10^{-50}$ g of iron oxide per gram of nanoparticles or nanoparticle cores.

In still another embodiment of the invention, the high purity nanoparticles, preferentially the cores of the high purity nanoparticles, comprise between $10^{-50}$ and 0.9999999999, 0.01 and 0.9999999999, 0.1 and 0.9999999999, 0.5 and 0.9999999999, 0.7 and 0.9999999999, 0.8 and 0.9999999999, 0.9 and 0.9999999999, 0.99999 and 0.9999999999, or between 0.9999999 and 0.9999999999 g of iron oxide per gram of nanoparticle or nanoparticle core.

In one embodiment of the invention, the high purity nanoparticles, preferentially the cores of the high purity nanoparticles, comprise more than $10^{-50}$, $10^{-30}$, $10^{-20}$, $10^{-10}$, $10^{-5}$, $10^{-3}$, 0.1, 0.2, 0.3, 0.4, 0.5, 0.7, 0.8, 0.9, 0.99, 0.999 or 0.9999999999 g of doping material per gram of nanoparticles or nanoparticle cores.

In another embodiment of the invention, the high purity nanoparticles, preferentially the cores of the high purity nanoparticles, comprise less than 0.9999999999, 0.999, 0.99, 0.9, 0.8, 0.7, 0.5, 0.3, 0.2, 0.1, $10^{-3}$, $10^{-5}$, $10^{-10}$ or $10^{-50}$ g of doping material per gram of nanoparticles or nanoparticle cores.

In still another embodiment of the invention, the high purity nanoparticles, preferentially the cores of the high purity nanoparticles, comprise between 0.000001 and 0.99999, 0.1 and 0.9, 0.2 and 0.8, 0.3 and 0.7, or between 0.5 and 0.8 g of doping material per gram of nanoparticle.

In still another embodiment of the invention, the high purity nanoparticles, preferentially the cores of these nanoparticles, comprise less doping material than iron oxide or predominant material, preferentially by a factor of more than 1.0000000001, 1.1, 1.2, 1.5, 2, 5, 10, $10^3$, $10^5$, $10^{10}$ or $^{100}$.

In still another embodiment of the invention, the high purity nanoparticles, preferentially the cores of these nanoparticles, comprise more doping material than impurity(ies), preferentially by a factor of more than 1.0000000001, 1.1, 1.2, 1.5, 2, 5, 10, $10^3$, $10^5$, $10^{10}$ or $^{100}$.

In one embodiment of the invention, the high purity nanoparticles, preferentially the coating of these nanoparticles, comprise more than $10^{-50}$, $10^{-30}$, $10^{-20}$, $10^{-10}$, $10^{-5}$, $10^{-3}$, 0.1, 0.2, 0.3, 0.4, 0.5, 0.7, 0.8, 0.9, 0.99, 0.999 or 0.9999999999 g of impurity(ies) per gram of nanoparticles or nanoparticle coating. In some cases, this situation can occur when the method does not enable to purify efficiently the nanoparticles.

In another embodiment of the invention, the high purity nanoparticles, preferentially the coating of these nanoparticles, comprise less than 0.9999999999, 0.999, 0.99, 0.9, 0.8, 0.7, 0.5, 0.3, 0.2, 0.1, $10^{-3}$, $10^{-5}$, $10^{-10}$ or $10^{-50}$ g of impurity(ies) per gram of nanoparticles or nanoparticle coating. In some cases, this situation can occur when the method enables to purify efficiently the nanoparticles.

In still another embodiment of the invention, the high purity nanoparticles comprise less impurity(ies) than doping material and/or iron oxide, preferentially by a factor of more than 1.0000000001, 1.1, 1.2, 1.5, 2, 5, 10, $10^3$, $10^5$, $10^{10}$ or $10^{100}$.

The invention also relates to the high purity nanoparticles according to the invention, wherein the doping material is selected from the group consisting of: Aluminum, antimonite, barium, chrome, copper, gold, manganese, silver, tin, titanium, and zinc.

In one embodiment of the invention, compared with nanoparticles with a large concentration of impurity, preferentially with more than 15000 μg of impurities per gram of nanoparticles, designated as $N_1$, nanoparticles with a low concentration of impurities, preferentially with less than 15000 μg of impurities per gram of nanoparticles, designated as $N_2$, possess at least one of the following advantageous property: i) better magnetic properties, such as a higher coercivity, remanent magnetization, saturating magnetization, preferentially by a factor larger than f, for N2 than for N1, ii) larger specific absorption rate (SAR), preferentially by a factor larger than f, for N2 than for N1, iii) a nanoparticle size distribution lower, preferentially by factor larger than f, for N2 than for N1, iv) a larger size, preferentially by factor larger than f, for N2 than for N1, v), a lower toxicity for N2 than for N1, and/or vi), an improvement in the medical, therapeutic, diagnostic, or cosmetic activity for N2 than for N1, and/or vi), less immunogenicity for N2 than for N1.

In one embodiment of the invention, the factor f is 1.0000001, 1.00001, 1.0001, 1.01, 1.1, 1.2, 1.5, 2, 5, 10, $10^3$, $10^5$, $10^7$ or $10^9$, or by a factor comprised between 1.000001 and $10^9$, 1.00001 and $10^7$, 1.0001 and $10^5$, 1.01 and $10^3$, 1.1 and $10^3$, 1.5 and $10^3$, 2 and $10^3$, 5 and $10^3$ or 5 and 100.

In one embodiment of the invention, the SAR is proportional to slope, preferentially initial slope, of the temperature variation with time of the nanoparticles, ($\Delta T/\delta t$), preferentially surrounded by a medium such as water, biological material, body part, or tissue, where ($\Delta T/\delta t$) is preferentially estimated in ° C./sec., where SAR=$\alpha(\Delta T/\delta t)$. In some cases, $\alpha=C_v/C_{nano}$, where $C_v$ is the specific heat capacity, preferentially of water, biological material, body part, or tissue, comprising the nanoparticles, and $C_{nano}$ is the nanoparticle concentration or quantity or number of nanoparticles, preferentially comprised in water, biological material, body part, or tissue.

In one embodiment, the SAR is measured by exposing the nanoparticles to a radiation, preferentially a radiation that produces heat, preferentially a laser, magnetic field, alternating magnetic field, acoustic wave, ultrasound, radiofrequency.

In one embodiment of the invention, the SAR of the nanoparticles is larger than $10^{-100}$, $10^{-50}$, $10^{-20}$, $10^{-10}$, $10^{-5}$, $10^{-3}$, $10^{-1}$, 1, 10, $10^3$ or $10^5$ Watt per gram of nanoparticles. In some cases, the SAR is large when the removal of impurities increases the SAR.

In another embodiment of the invention the SAR of the nanoparticles is lower than $10^{100}$, $10^{50}$, $10^{30}$, $10^{20}$, $10^{10}$, $10^5$, $10^2$, 10, 1, $10^{-1}$, $10^{-3}$ or $10^{-5}$ Watt per gram of nanoparticles. In some cases, the SAR is low when the removal of impurities partly or fully destroys or denatures the nanoparticles.

In one embodiment of the invention, the nanoparticle size distribution is larger than $10^{-50}$, $10^{-20}$, $10^{-10}$, $10^{-5}$, $10^{-2}$, $10^{-1}$, 1, 5, 10, $10^2$ or $10^5$ nm. In some cases, the nanoparticle size distribution is large when the removal of impurity(ies) partly or fully destroys or denatures or reduces or increases the size of the nanoparticles, preferentially by a factor of more than 1.00001, 1.001, 1.1, 2, 5, 10, 50, $10^2$, $10^3$, $10^5$, $10^{10}$, $10^{20}$ or $10^{50}$ between before and after the method.

In another embodiment of the invention, the nanoparticle size distribution is lower than $10^{50}$, $10^{20}$, $10^{10}$, $10^5$, $10^3$, $10^2$, 10, 1, $10^{-1}$, $10^{-2}$ or $10^{-5}$ nm. In some cases, the nanoparticle size distribution is low when the removal of impurity(ies) does not partly or fully destroy or denature or does not reduce or increase the size of the nanoparticles, preferentially by a factor of more than 1.00001, 1.001, 1.1, 2, 5, 10, 50, $10^2$, $10^3$, $10^5$, $10^{10}$, $10^{20}$ or $10^{50}$ between before and after the method.

In another embodiment of the invention, the nanoparticles, preferentially at a concentration larger than $10^{-6}$, $10^{-3}$, $10^{-1}$, 1, 10 mg of nanoparticles per ml or $mm^3$, destroy more than 1, 10, $10^3$, $10^6$, $10^9$ cell(s), preferentially when the nanoparticles and cells are comprised in a volume lower than 1 $cm^3$ or 1 $mm^3$. In some cases, preferentially when the impurity(ies) is/are toxic or induce(s) toxicity, the nanoparticles destroy more cells, preferentially by a factor of more than 1.00001, 1.001, 1.1, 2, 5, 10, 50, $10^2$, $10^3$, $10^5$, $10^{10}$, $10^{20}$ or $10^{50}$ before the method, where the quantity of impurities is the largest, than after the method, where the quantity of impurities is the lowest.

In another embodiment of the invention, the nanoparticles after the method or after being treated by the method yield an improved: i) medical or therapeutic activity, for example by enabling the destruction of a larger number of pathological cells, viruses, cancer cells, or by being less toxic towards healthy tissues, ii) diagnostic activity, for example by enabling the detection of a larger number of pathological cells, viruses, cancer cells, or by being less toxic towards healthy tissues, and/or, iii) cosmetic activity, for example by improving the appearance of a larger number of cells or by being less toxic towards healthy tissues.

In another embodiment of the invention, the nanoparticles after the method or after being treated by the method are less immunogenic than before the method or before being treated by the method. Preferentially, they attract a less important number of immune cells, preferentially under the application (or not) of radiation, preferentially by a factor of more than 1.00001, 1.001, 1.1, 2, 5, 10, 50, $10^2$, $10^3$, $10^5$, $10^{10}$, $10^{20}$ or $10^{50}$, after than before the method.

In another embodiment of the invention, the nanoparticles after the method or after being treated by the method are more immunogenic than before the method or before being treated by the method. Preferentially, they attract a more important number of immune cells, preferentially under the application (or not) of radiation, preferentially by a factor of more than 1.00001, 1.001, 1.1, 2, 5, 10, 50, $10_2$, $10^3$, $10^5$, $10^{10}$, $10^{20}$ or $10^{50}$, after than before the method.

In another embodiment of the invention, the nanoparticles after the method or after being treated by the method are less pyrogenic than before the method or before being treated by the method. Preferentially, they induce an increase in temperature, preferentially of the organism or cell or cell assembly in which they are comprised or administered, which is lower than 50, 20, 10, 5, 2, 1 or 0.5° C. Preferentially, they induce an increase in temperature, preferentially of the organism or cell or cell assembly in which they are comprised or administered, which is lower by at least 50, 20, 10, 5, 2, 1, 0.5, or 0.00001° C. after the method than before the method. In some cases, this situation can occur when the impurity(ies) is/are pyrogenic or increase(s) the pyrogenicity of the nanoparticles.

In another embodiment of the invention, the nanoparticles after the method or after being treated by the method are more pyrogenic than before the method or before being treated by the method. Preferentially, they induce an increase in temperature, preferentially of the organism or cell or cell assembly in which they are comprised or administered, which is larger than 50, 20, 10, 5, 2, 1 or 0.5° C. Preferentially, they induce an increase in temperature, preferentially of the organism or cell or cell assembly in which they are comprised or administered, which is larger by at least 50, 20, 10, 5, 2, 1, 0.5, or 0.00001° C. after the method than before the method. In some cases, this situation can occur when the impurity(ies) reduce the pyrogenicity of the nanoparticles.

The invention also relates to the nanoparticle(s) obtained by the method according to the invention, wherein the yield of nanoparticle production is larger than $10^{-50}$, $10^{-30}$, $10^{-10}$, $10^{-5}$, $10^{-2}$, $10^{-1}$, 1, 5, 10, 50, $10^2$, $10^3$, or $10^5$ mg of nanoparticle(s), preferentially per cell, preferentially per liter of pre-growth and/or growth medium/media.

The invention also relates to the nanoparticle(s) obtained by the method according to the invention, wherein the yield of nanoparticle production is lower than $10^{50}$, $10^{30}$, $10^{10}$, $10^5$, $10^2$, 10, 5, 1, $10^{-1}$, $10^{-2}$, $10^{-3}$, or $10^{-5}$ mg of nanoparticle(s), preferentially per cell, preferentially per liter of pre-growth and/or growth medium/media.

The invention also relates to the high purity nanoparticle(s) according to the invention, which is/are magnetosomes.

In one embodiment of the invention, the magnetosomes are nanoparticles produced by magnetotactic bacteria that are preferentially treated in the following fashion: i), nanoparticles are extracted and/or isolated from the bacteria to obtain magnetosomes comprising crystallized minerals surrounded by a biological membrane, ii), the biological membrane is removed, preferentially using the purifying step, iii), the magnetosomes are coated with a synthetic coating that does not originate from the magnetotactic bacteria for stabilization, preferentially to avoid that the magnetosomes aggregate and/or sediment.

The invention also relates to a composition, drug, medical device, diagnostic composition, therapeutic composition, or cosmetic composition, comprising the high purity nanoparticle(s) according to the invention.

In still another embodiment of the invention, the property(ies) or features, preferentially of the nanoparticle(s) or method, described in each individual embodiment or section or sentence of this patent application can be combined to result in a combination of property(ies) or features, preferentially of the nanoparticle(s) or method.

In still another embodiment of the invention, when a compound such as the nanoparticle or chemical element has a property in a condition 1 (P1) that is higher, longer, or larger by a factor $\alpha$ than a property in a condition 2 (P2), it means that $P1=\alpha P2$.

In still another embodiment of the invention, when a compound such as as the nanoparticle or chemical element has a property in a condition 1 (P1) that is smaller, or shorter by a factor $\alpha$ than a property in a condition 2 (P2), it means that $P1=P2/\alpha$.

The invention will be further disclosed by the following non-limiting examples.

EXAMPLES

Materials and Methods

Equipment Used to Analyze and Heat the Various Samples

TGA-DSC: "Thermogravimetric analysis" (TGA) coupled to "Differential Scanning calorimetry" (DSC) is used to measure heat flow (in mW) or the percentage of mass loss of powders comprising lyophilized magnetosomes (treated or not) or lyophilized whole bacteria or lyophilized SIGMA nanoparticles as a function of the heating temperature of these powders. For the measurements, the powders are heated at a rate of 6° C. per minute between 20° C. and 600° C. The derivative of the percentage of mass variation of the powders is also plotted as a function of temperature. The TGA-DSC profiles make it possible to define the temperatures for which the material, preferentially organic material, located in or at the surface of the magnetosomes or nanoparticles will be degraded, removed from the nanoparticles, or transformed. ATG and DSC analyzes were performed with the SDT Q600 (TA Instrument). It consists of a sealed enclosure, a furnace with temperature control, a micro-balance, and a thermocouple to measure the temperature.

CHNS: "Elemental Carbon, Hydrogen Nitrogen and Sulfur Analyzer" CHNS measurements are carried out using a CHNS analyzer (Flash Elemental Analyzer EA 1112 from Thermo Fischer scientific) using a mass of 3 mg per measurement of lyophilized magnetosomes (conditions of treatment n°1, 2, 3, 4, 5, 6, 7, 8, 9, 10, 11), lyophilized whole bacteria, lyophilized SIGMA nanoparticles (not treated). CHNS measurements enable to determine the percentages in mass of carbon and nitrogen in the different powders.

Furnace: A muffle furnace (Nabertherm L9/11/B410) is used to heat 30 mg or 500 mg of magnetosomes extracted from magnetotactic bacteria following condition n°1 or 2 without heat treatment above 200° C. or with heat treatment above 200° C. (following condition n° 3, 4, 5, 6, 7, 8, 9, 10 or 11). For that, the 30 or 500 mg powder of each sample is deposited in an uncovered porcelain cup and placed at the center of the furnace. A program is used to carry out the different heating conditions. The furnace enables to maintain the temperature of the nanoparticles or the temperature inside the furnace at a given temperature plus or minus 2° C., or the furnace enables to obtain a stable temperature between 20° C. and 380° C. with a fluctuation of 2° C. maximum.

Preparation of the Different Samples

Growth of whole MSR-1 magnetotactic bacteria: 50 mL of MSR-1 magnetotactic bacteria purchased from DSMZ were first divided into 83 samples/Eppendorf of 600 μL and then frozen at −80° C. MSR-1 magnetotactic bacteria were grown in a 70-liter fermenter, using four steps. During the first three steps, called pre-growth steps, the bacteria were amplified without producing a large quantity of magnetosomes. During the last step, called the growth step, the bacteria produced magnetosomes. The pre-growth step 1 took place according to the following protocol. We used a 500 ml flask that we filled with 250 ml of deionized water, 1.3 g of 60% sodium lactate (2.6 g/l), 0.2 g of ammonium (0.4 g/L), 0.05 g of yeast extract (0.1 g/L), 0.05 g magnesium sulfate heptahydrate (0.1 g/L), 0.25 g of potassium phosphate dibasic trihydrate (0.5 g/L), 250 μL of a solution of mineral elixir at pH 7 that comprises in 1 liter of deionized water: 15 g of trisodium nitriloacetic acid, 3 g of magnesium sulfate heptahydrate, 2 mg of manganese (II) sulfate monohydrate, 10 g of sodium chloride, 3 mg of cobalt (II) nitrate hexahydrate, 30 g of calcium chloride, 1 g of iron (II) sulfate heptahydrate, 3 mg of zinc sulfate heptahydrate, 2 mg of copper sulfate pentahydrate, 5 mg of potassium aluminum disulfate dodecahydrate, 100 mg of boric acid, 100 mg of sodium molybdate (VI) dihydrate, 2 mg of nickel chloride hexahydrate, 3 mg of disodium selenite pentahydrate. We added deionized water to the pre-growth medium until the total volume of the pre-growth medium was 500 mL. The pre-growth medium thus obtained was homogenized and filtered using a filtration unit (with filters of pore size of 0.45 μm) for sterilization. A 600 μl aliquot of MSR-1 magnetotactic bacteria was thawed in a water bath at 37° C. for 5 min and the bacteria were introduced into 250 mL of the previously filtered pre-growth medium. The bacteria were then incubated at 29.5° C. during 5 days without agitation. For the pre-growth step number 2, a volume of 3 liters of pre-growth medium was prepared by mixing 500 mL of deionized water with 7.8 g of 60% sodium lactate (2.6 g/L), 1.2 g of ammonium chloride (0.4 g/L), 0.3 g of yeast extract (0.1 g/L), 0.3 g of magnesium sulfate heptahydrate (0.1 g/L), 1.5 g of potassium phosphate dibasic trihydrate (0.5 g/L), 1500 μL of a solution of mineral elixir prepared as previously described. The final volume of the pre-growth medium was adjusted with deionized water to reach 3 liter. The pre-growth medium was homogenized and filtered using a filtration unit (using filters with pore sizes of 0.45 μm) to sterilize the pre-growth medium. In a 5 L bottle, 1.5 L of pre-growth medium was introduced with 250 mL of bacteria originating from the pre-growth step 1. The whole medium comprising the bacteria was stirred at 110 rpm at a temperature of 29.5° C. for 72 hours. For the pre-growth step 3, a volume of 8 liters of pre-growth medium was prepared by mixing 1 L of deionized water with 20.8 g of 60% sodium lactate (2.6 g/L), 3.2 g of ammonium chloride (0.4 g/L), 0.8 g of yeast extract (0.1 g/L), 0.8 g of magnesium sulfate heptahydrate (0.1 g/L), 4 g of potassium phosphate dibasic trihydrate (0.5 g/L), 4000 μL of a solution of mineral elixir prepared as previously described. The volume of the growth medium was adjusted to 8 liters using deionized water. The pre-growth medium was homogenized and filtered using a filtration unit (filters with pore sizes of 0.45 μm) to sterilize the pre-growth medium. In a 10 L bottle, 4 L of pre-growth medium was introduced with 1.5 L of magnetotactic bacteria originating from the pre-growth step 2. The whole medium was stirred at 110 rpm at a temperature of 29.5° C. for 24 hours. To start the growth step in the 70 liter fermenter, a volume of 5 L of fermentation medium was first prepared by mixing 2 L of deionized water, 46.8 g of 60% sodium lactate (9.4 g/L), 7.8 g of ammonium chloride (1.5 g/L), 2.3 g of yeast extract (0.5 g/L), 0.95 g of magnesium sulfate heptahydrate (0.19 g/L), 2.3 g of potassium phosphate dibasic trihydrate (0.5 g/L), 2800 μL of a solution of mineral elixir prepared as previously described. The final volume of the fermentation medium was adjusted to 5 liters with deionized water. The whole medium was homogenized and filtered using a filtration unit (using filters with pores of 0.45 μm) to sterilize the fermentation medium. A volume of 15 L of fed-batch medium was prepared by mixing 5 L of deionized water with 1500 g of lactic acid at 90% (100 g/L), 270 mL of a solution of ammonia at 28% (5 g/L), 90 g of potassium phosphate dibasic trihydrate (6 g/L), 36 g of magnesium sulfate heptahydrate (2.4 g/L), 30 g of iron chloride hexahydrate (2 g/L), 90 g of yeast extract (6 g/L), 105 mL of a solution of mineral elixir prepares as previously described. The final volume of the fed-batch medium was adjusted to 15 L with deionized water. The whole medium was homogenized and filtered using a filtration unit (filters with pores of 0.45 μm) for sterilization. Finally, a volume of 1 mL of polypropylene was added aseptically in the fed-batch medium after filtration to prevent the formation of foam that could occur for a density of bacteria increased above an optical density of 2. After pasteurization of the 70 liters fermenter, 10 liters of water, 5 liters of fermentation medium, and 4 or 8 liters of bacteria resulting from pre-growth step 3, were introduced in the fermenter, so that the optical density (measured at 565 nm) of the growth medium comprising the bacteria was at the start of the fermentation between 0.09 and 0.11. The temperature of the fermentation medium was maintained at 29.5° C. throughout the duration of the fermentation. The pH of the fermentation medium was maintained at 6.9 for the duration of the fermentation by adding a Fed-Batch medium, which comprises iron and hence enables magnetosome production in large quantities. The total fermentation time was 75 hours, with a decrease in oxygen content from 21% at the beginning of fermentation to 0.9% 12 hours afterwards. Between 12 hours and 75 hours, the percentage of dissolved oxygen in the growth medium is maintained above 0% to allow the growth of bacteria and below 0.9% to allow the synthesis of magnetosomes. To maintain this oxygen concentration in the growth medium, an increasing concentration of oxygen was provided to the fermentation medium with a flow rate at 0.5 L/min between 0 and 16 hours and a flow rate between 0.5 L/min and 5 L/min between 16 and 75 hours throughout the fermentation step. 75 hours following the beginning of the growth step, that is to say when the optical density, measured at 565 nm, reaches a plateau between 10 and 20, the fermentation is stopped by stopping the oxygenation, Fed-Batch, and agitation. Magnetotactic bacteria are then collected and concentrated using a tangential filtration system to an optical density, measured at 565 nm ($OD_{565}$), between 100 and 200.

Sample 0: A volume of 1 mL of concentrated bacteria is lyophilized. A mass of 3 mg of lyophilized bacteria is used for TGA-DSC analysis and another mass of 12 mg of lyophilized bacteria is used for 3 CHNS measurements. Sample 0 was prepared from 8 different fermentations.

Samples Comprising Magnetosomes Extracted from Magnetotactic Bacteria Without Heat Treatment Above 200° C.:

Condition 1 of lysis: 100 ml of cultivated magnetotactic bacteria, concentrated at an $OD_{565}$ nm of 120, were mixed with 400 ml of 5M NaOH and sonicated and heated at 60° C. for 1 hour using a sonic bath to lyse the bacteria. The treated magnetosomes were then isolated from the bacterial debris by placing a Neodinium magnet overnight against the wall of the container containing the lysed bacteria suspension and by replacing the supernatant containing the medium and bacterial debris by 1×PBS. The resulting suspension was then sonicated for 20 seconds at 10 W in the presence of 1×PBS, placed against a Neodinium magnet for 15 minutes, the supernatant was removed and the treated magnetosomes were resuspended in 1×PBS. This sequence of sonication and magnetic separation was repeated four times. For an entire fermenter, this treatment was repeated 10 times in 10 different volumes. Pyrogenic magnetosome chains extracted from MSR-1 magnetotactic bacteria were thus obtained, i.e. approximately 500 mg in iron of magnetosomes comprised in 1.7 ml of water.

Sample 1: It comprises magnetosomes obtained from condition 1 of lysis. 100 μL the suspension of magnetosomes resulting from condition 1 of lysis was lyophilized to carry out 3 measurements of 3 mg of magnetosome powder with the CHNS. This type of CHNS measurements was made for 4 different cultures in fermenter.

Condition 2 of lysis: Concentrated magnetotactic bacteria were frozen at −80° C. for 48 hours. After thawing and dilution of the concentrate with MilliQ water to obtain an $OD_{565nm}$ of 30, an amount of KOH was added to obtain to the concentrated bacteria to obtain a final KOH concentration of 1M. This solution was transferred to a polypropylene (PP) tank and placed in the water bath at 80° C. with stirring at 150 rpm with a mechanical stirring pad (Fisher Scientific), for 30 minutes. Then, the content of the tank was transferred into 4 glass bottles of 2 L. Each bottle was placed against a NdFeB magnet for 12 hours to magnetically select the extracted magnetosomes. The magnetosomes were then washed 6 times in 500 mL bottles by magnetic selection, until a clear supernatant is obtained. The first two washes were carried out with 10×PBS, which makes it possible to return to a neutral pH more rapidly with respect to water. Then the other four washes were carried out with water. After lysis, the basic pH of the lysate, caused by the KOH, was brought back to a neutral pH so as not to damage the magnetosomes. For an entire fermenter, this treatment was carried out 5 times. Pyrogenic magnetosome chains extracted from the strain MSR-1 were thus obtained, i.e. about 500 mg in iron of magnetosomes in 1.7 ml.

Sample 2: It comprises magnetosomes obtained after condition 2 of lysis. 100 μL the suspension of magnetosomes resulting from condition 2 of lysis was lyophilized to carry out one measurement of 3 mg of magnetosome powder with TGA-DSC and 3 measurements of 3 mg of magnetosome powder with the CHNS. This type of CHNS measurements was made for 4 different cultures in fermenter.

Samples Comprising Magnetosome Extracted from Magnetotactic Bacteria and Treated with Phenol-Chloroform:

Condition 3 of treatment: 100 μl of the suspension containing 30 mg in iron of magnetosomes obtained following condition 1 of lysis were mixed with 200 ml of a solution containing 1% Triton X-100 and 1% SDS. The mixture was heated overnight at 50° C., was placed against a Neodinium magnet, the supernatant was removed and replaced with 80 mL of phenol at pH 8. The obtained suspension was heated for 2 hours under sonication at 60° C., held overnight at 60° C. without sonication, placed against a magnet, the supernatant of the suspension was removed and replaced with 80 mL of chloroform. The suspension containing the chloroform was placed against a magnet of Neodinium, the supernatant was removed and the residual chloroform adsorbed at the surface of the treated magnetosomes was removed by heating these magnetosomes for 2 hours under a hood. Finally, the cores of the magnetosomes thus obtained were desorbed from the glass wall from the tubes containing them by adding 80 ml of 1M NaOH heated for 1 hour at 60° C. in a sonic bath. The suspension containing the cores of the magnetosomes was placed against a Neodinium magnet. The supernatant was removed and replaced with sterile MilliQ water. The suspension was sonicated for 20 seconds at 10 W. This washing sequence was repeated four times. Purified pyrogen-free magnetosomes were obtained in a small volume of pyrogen-free water.

Sample 3: It comprises magnetosomes obtained after condition 3 of treatment. 300 μL the suspension of magnetosomes resulting from condition 3 of treatment was lyophilized to carry out one measurement of 3 mg of magnetosome powder with TGA-DSC and 3 measurements of 3 mg of magnetosome powder with the CHNS. This type of CHNS measurements was made for 4 different cultures in fermenter.

Samples Comprising Magnetosome Extracted from Magnetotactic Bacteria and Heated at Temperatures Above 200° C.:

Condition 4 of heat treatment: 100 μl of the suspension containing approximately 30 mg in iron of magnetosomes extracted from MSR-1 magnetotactic bacteria following condition 2 of lysis were lyophilized, introduced into a porcelain crucible, and baked in the furnace Nabertherm L9/11/B410. The heating protocol was as follows. The temperature of the furnace was increased from 20° C. to 200° C. at a rate of 6° C./min until the temperature of the furnace reaches 200° C. and the temperature of 200° C. in the furnace was maintained during one hour. Then the temperature of the furnace was decreased from 200° C. to 25° C. in 12 hours Sample 4: It comprises magnetosomes obtained after condition 4 of treatment. 12 mg of magnetosome powder resulting from condition 4 of treatment were lyophilized to carry out 3 measurements of 3 mg of magnetosome powder with the CHNS. This type of CHNS measurements was made for 4 different cultures in fermenter.

Condition 5 of heat treatment: 100 μl of the suspension containing approximately 30 mg in iron of magnetosomes extracted from MSR-1 magnetotactic bacteria following condition 2 of lysis were lyophilized, introduced into a porcelain crucible, and baked in the furnace Nabertherm L9/11/B410. The heating protocol was as follows. The temperature of the furnace was increased from 20° C. to 400° C. at a rate of 6° C./min until the temperature of the furnace reaches 400° C. The temperature in the furnace was maintained at 400° C. for one hour. Then the temperature of the furnace was decreased from 400° C. to 25° C. in 20 hours Sample 5: It comprises magnetosomes obtained after condition 5 of treatment. 12 mg of magnetosome powder resulting from condition 5 of treatment were used to carry out 3 measurements of 3 mg of magnetosome powder with the CHNS. This type of CHNS measurements was made for 4 different cultures in fermenter.

Condition 6 of heat treatment: 100 μl of a suspension comprising 30 mg in iron of magnetosomes prepared according to condition 2 of lysis, were lyophilized and then introduced into a porcelain crucible and heated in the furnace Nabertherm L9/11/B410. The heat treatment was as follows. The temperature of the furnace was increased from 20° C. to 200° C. in 20 min at a rate of 9° C./min. The temperature of the furnace was then maintained at 200° C. for 30 minutes. The temperature of the furnace was then increased from 200° C. to 300° C. in 10 min at a rate of 10° C./min. The temperature of the furnace was then maintained at 300° C. for 1 hour. Then the temperature of the furnace was decreased from 300° C. to 25° C. in 12 hours Sample 6: It comprises magnetosomes obtained after condition 6 of treatment. 12 mg of magnetosome powder resulting from condition 6 of treatment were used to carry out 3 measurements of 3 mg of magnetosome powder with the CHNS. This type of CHNS measurements was made for 4 different cultures in fermenter.

Condition 7 of heat treatment: 100 μl of a suspension comprising 30 mg in iron of magnetosomes prepared according to condition 2 of lysis, were lyophilized and then introduced into a porcelain crucible and heated in the furnace Nabertherm L9/11/B410. The heat treatment was as follows. The temperature of the furnace was increased from 20° C. to 200° C. in 20 min at a rate of 9° C./min. The temperature of the furnace was then maintained at 200° C. for 30 minutes. The temperature of the furnace was then increased from 200° C. to 300° C. in 10 min at a rate of 10° C./min. The temperature of the furnace was then maintained at 300° C. for 1 hour. The temperature of the furnace was then increased from 300 to 380° C. in 10 min at a rate of 8° C./min. The temperature of the furnace was then maintained at 380° C. for 1 hour. The temperature of the furnace was then increased from 380° C. to 550° C. in 20 min at a rate of 8.5° C./min. The temperature of the furnace was then maintained at 550° C. for 1 h. Then the temperature of the furnace was decreased from 550° C. to 25° C. in 20 hours.

Sample 7: It comprises magnetosomes obtained after condition 7 of treatment. 12 mg of magnetosome powder resulting from condition 7 of treatment were used to carry out 3 measurements of 3 mg of magnetosome powder with the CHNS. This type of CHNS measurements was made for 4 different cultures in fermenter.

Condition 8 of heat treatment: 100 μl of the suspension containing 30 mg in iron of magnetosomes prepared according to condition 2 of lysis, were lyophilized and then introduced into a porcelain crucible and baked in the furnace Nabertherm L9/11/B410. The heat treatment was as follows. The temperature of the furnace was increased from 20° C. to 200° C. in 20 min at a rate of 9° C./min. The temperature of the furnace was then maintained at 200° C. for 30 minutes. The temperature of the furnace was then increased from 200° C. to 300° C. in 10 min at a rate of 10° C./min. The temperature of the furnace was then maintained at 300° C. for 1 hour. The temperature of the furnace was increased from 300° C. to 380° C. in 10 min at a rate of 8° C./min. The temperature of the furnace was then maintained at 380° C. for 1 h. Then the temperature of the furnace was decreased from 380° C. to 25° C. in 12 hours Sample 8: It comprises magnetosomes obtained after condition 8 of treatment. 12 mg of magnetosome powder resulting from condition 8 of treatment were used to carry out 3 measurements of 3 mg of magnetosome powder with the CHNS. This type of CHNS measurements was made for 4 different cultures in fermenter.

Condition 9 of heat treatment: 100 μl of the suspension containing 30 mg in iron of magnetosomes prepared according to condition 1 of lysis, were lyophilized and then introduced into a porcelain crucible and heated in the furnace Nabertherm L9/11/B410. The heat treatment was as follows. The temperature of the furnace was increased from 20° C. to 200° C. in 20 min at a rate of 9° C./min. The temperature of the furnace was then maintained at 200° C. for 30 minutes. The temperature of the furnace was then increased from 200° C. to 300° C. in 10 min at a rate of 10° C./min. The temperature of the furnace was then maintained at 300° C. for 1 hour. The temperature of the furnace was increased from 300° C. to 380° C. in 10 min at a rate of 8° C./min. The temperature of the furnace was then maintained at 380° C. for 1 h. Then the temperature of the furnace was decreased from 380° C. to 25° C. in 12 hours.

Sample 9: It comprises magnetosomes obtained after condition 9 of treatment. 12 mg of magnetosome powder resulting from condition 9 of treatment were used to carry out 3 measurements of 3 mg of magnetosome powder with the CHNS. This type of CHNS measurements was made for 4 different cultures in fermenter.

Condition 10 of heat treatment: 1.7 mL of a suspension containing 500 mg in iron of magnetosomes prepared according to condition n°2 of lysis, were lyophilized and then introduced into a porcelain crucible and heated in the furnace Nabertherm L9/11/B410. The heat protocol was as follows. The temperature of the furnace was increased from 20° C. to 200° C. in 2 hours 30 min at a rate of 1.2° C./min. The temperature of the furnace was then maintained at 200° C. for 1 hour. The temperature of the furnace was then increased from 200° C. to 300° C. in 1h20 min at a rate of 1.25° C./min. The temperature of the furnace was then maintained at 300° C. for 2 hours. The temperature of the furnace was then increased from 300° C. to 380° C. in 1 hour 20 min at a rate of 1° C./min. The temperature of the furnace was then maintained at 380° C. for 2 h. Then the temperature of the furnace was decreased from 380° C. to 25° C. in 12 hours.

Sample 10: It comprises magnetosomes obtained after condition 10 of treatment. 12 mg of magnetosome powder resulting from condition 10 of treatment were used to carry out 3 measurements of 3 mg of magnetosome powder with the CHNS. This type of CHNS measurements was made for 4 different cultures in fermenter.

Condition 11 of heat treatment: 1.7 mL of a suspension containing 500 mg in iron of magnetosomes prepared according to condition n°1 of lysis, were lyophilized and then introduced into a porcelain crucible and heated in the furnace Nabertherm L9/11/B410. The heat treatment was as follows. The temperature of the furnace was increased from 20° C. to 200° C. in 2 hours and 30 minutes at a rate of 1.2° C./min. The temperature of the furnace was then maintained at 200° C. for 1 hour. The temperature of the furnace was then increased from 200° C. to 300° C. in 1h20 min at a rate of 1.25° C./min. The temperature of the furnace was then maintained at 300° C. for 2 hours. The temperature of the furnace was then increased from 300° C. to 380° C. in 1 hour 20 min at a rate of 1° C./min. The temperature of the furnace was then maintained at 380° C. for 2 h. Then the temperature of the furnace was decreased from 380° C. to 25° C. in 12 hours.

Sample 11: It comprises magnetosomes obtained after condition 11 of treatment. 12 mg of magnetosome powder resulting from condition 11 of treatment were used to carry out 3 measurements of 3 mg of magnetosome powder with the CHNS. This type of CHNS measurements was made for 4 different cultures in fermenter.

Chemically synthesized nanoparticles (SIGMA, reference: 637106, batch n°: MKBK2270V): Powder of chemically synthesized nanoparticles have been purchased from SIGMA. They have a size of 35±13 nm and they comprise in addition to iron oxide, 198 ppm of Aluminum (Al), 600 ppm of Calcium (Ca) 74 ppm of Chromium (Cr), 72 ppm of Magnesium (Mg), 642.5 ppm of Manganese (Mn), 30 ppm of Nickel (Ni), 128 ppm of Sodium (Na), 34 ppm of Titanium (Ti), 8.3 ppm of Vanadium (V), 56.5 ppm of Zinc (Zn).

Sample comprising SIGMA nanoparticles: A mass of 3 mg of powder of SIGMA nanoparticle is used for TGA-DSC analysis and another mass of 12 mg of powder of SIGMA nanoparticle is used for 3 CHNS measurements.

FIG. 1 (*a*) shows the percentage of weight loss of a sample comprising 3 mg of lyophilized whole MSR-1 magnetotactic bacteria (Sample 0) as a function of sample temperature, when the temperature of the sample is increased from 20° C. to 600° C. at a rate of 6° C. per minute, as well as the first derivative of this percentage. These measurements have been carried out with a combined TGA-DTA/DSC apparatus, measuring both heat flow using Differential Scanning calorimetry and weight changes using Thermogravimetry in a material as a function of temperature. CHNS measurements of 3 mg of lyophilized whole MSR-1 magnetotactic bacteria (Sample 0) have shown that they contain a large percentage of carbon of 44%, before being heated (FIG. 3(*a*)). The percentage in weight of this sample decreases from 100% at 20° C. down to 5.5% at 600° C., indicating that the sample loses most of its mass between 20 and 600° C. More specifically, it appears in FIG. 1(*a*) that the slope of the variation of the percentage of weight as a function of temperature is the largest within two temperature ranges: between 200 and 400° C. (interval 1) and between 400 and 540° C. (interval 2). Between 200 and 400° C., the variation as a function of temperature of the slope of the percentage of weight as a function of temperature displays a double peak whose maximum are at 260° C. and 315° C. This double peak could be due to the loss by the whole magnetotactic bacteria of organic material, preferentially of type 1, for the peak centered at 260° C. and of organic material, preferentially of a different type than type 1 such as type 2, for the peak centered at 315° C. Between 400 and 540° C., the variation as a function of temperature of the slope of the percentage of weight variation as a function of temperature displays a peak. This peak could be due to the loss by the nanoparticles of organic material, preferentially of a different type than type 1 or type 2 such as type 3.

FIG. 1(*b*) shows the heat flow in milliwatt of a sample comprising 3 mg of lyophilized whole magnetotactic bacteria as a function of sample temperature, when the temperature of the sample is increased from 20° C. to 600° C. at a rate of 6° C. per minute. These measurements have been carried out with a TGA-DSC apparatus. FIG. 1(*b*) shows two peaks with maximum heat flow observed at temperatures of 330° C. and 500° C. The peak centered at 330° C. could be attributed to the combustion of the mass of nanoparticles that has been lost or removed from the nanoparticles or transformed between 200 and 400° C. The peak at 500° C. could be attributed to the combustion of the mass of nanoparticles that has been lost between 500 and 540° C.

FIG. 1(*c*) shows the percentage of variation of the weight of a sample comprising 3 mg of lyophilized chains of magnetosomes prepared according to condition 2 of lysis as a function of sample temperature, when the temperature of the sample is increased from 20° C. to 600° C. at a rate of 6° C. per minute, as well as the first derivative of this percentage. These measurements have been carried out with a TGA-DSC apparatus. CHNS measurements of lyophilized chains of magnetosomes (condition n°2) have shown that they contain a percentage of carbon of 7%, before being heated, which is much lower than the percentage of carbon in whole magnetotactic bacteria (FIG. 3(*a*)). The percentage in weight of the sample comprising chains of magnetosomes decreases from 100% at 20° C. down to 91.4% at 600° C., indicating that the sample comprising chains of magnetosomes loses much less mass, i.e. 8.6%, than the sample comprising whole magnetotactic bacteria between 20° C. and 600° C.

More specifically, it appears in FIG. 1(*c*) that the slope of the variation of the percentage in weight of the chains of magnetosomes as a function of temperature is the largest within the temperature range of 200 to 400° C. Between 200 and 400° C., the variation as a function of temperature of the slope of the percentage in weight of the chains of magnetosomes as a function of temperature displays a double peak whose maximum are at 260° C. and 315° C., similar positions than those of the double peak observed with whole bacteria. This double peak could be due to the loss by the chains of magnetosomes of organic material, preferentially organic material of type 1, for the peak centered at 260° C. and of organic material, preferentially organic material of type 2 for the peak centered at 315° C., where this organic material likely comes from the organic membrane layer surrounding the mineral iron oxide core of the magnetosomes. FIG. 1(*d*) shows the heat flow in milliwatt of a sample comprising 3 mg of lyophilized chains of magnetosomes as a function of the sample temperature, when the temperature of the sample is increased from 20° C. to 600° C. at a rate of 6° C. per minute. These measurements have been carried out with a TGA-DSC apparatus. FIG. 1(*d*) shows three peaks with maximum heat flow observed at temperatures of 250° C., 360° C., and 525° C. The peaks centered at 250° C. and 360° C. could be attributed to the combustion of the mass of nanoparticles that has been lost between 200 and 400° C. The peak at 525° C. could be attributed to the combustion of the mass of nanoparticles that has been lost above 500° C. and/or to the oxidation of the magnetosomes from an iron oxide composition of magnetite, maghemite, or an intermediate composition between magnetite and maghemite into hematite, which could result in heat flow possibly caused by an exothermic reaction.

Figure 2:
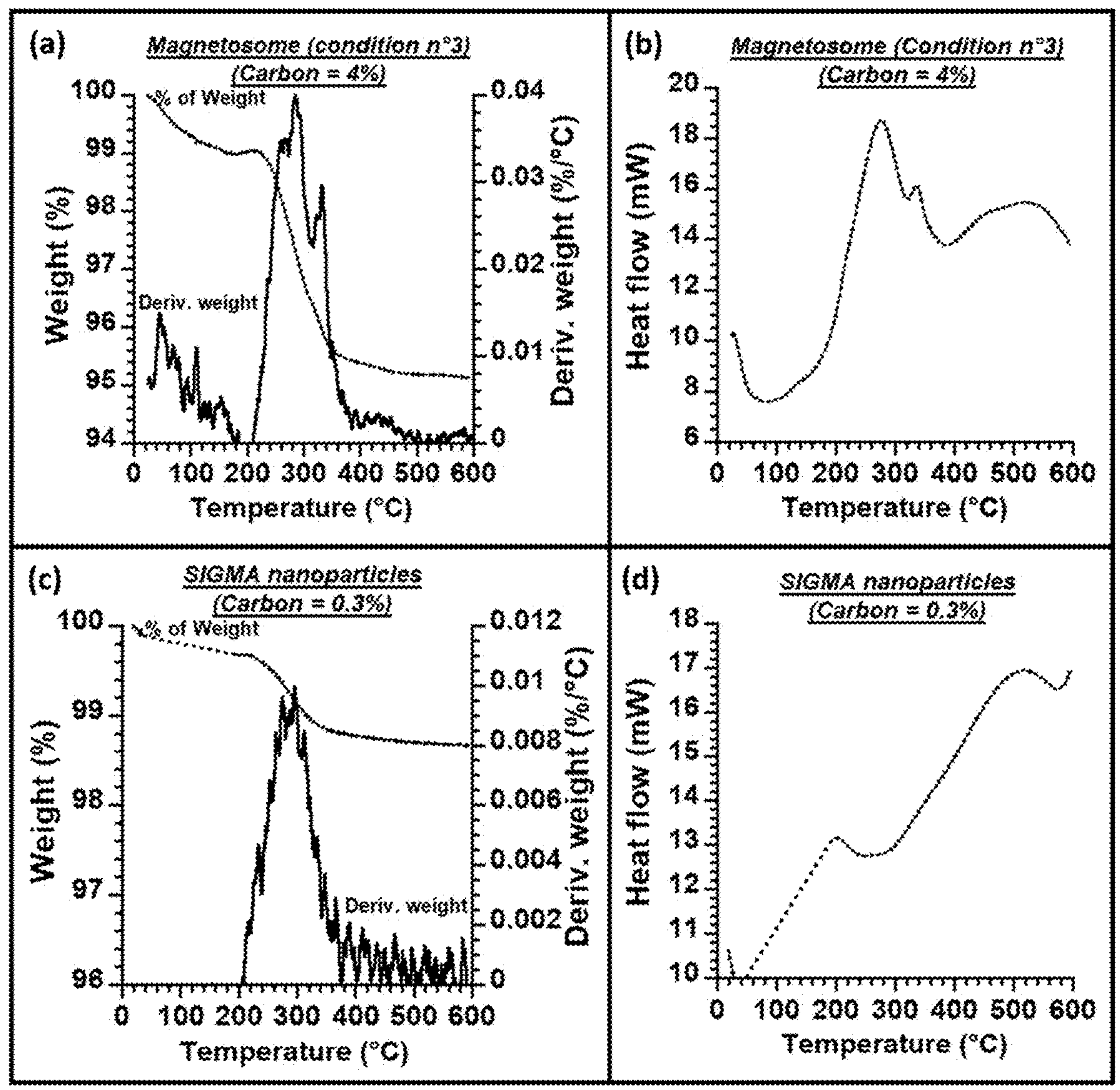
FIG. 2: TGA-DSC analysis of magnetosomes extracted from magnetotactic bacteria according to condition 3 and of chemically synthesized SIGMA nanoparticles. (a) Variation of the percentage in weight as a function of temperature as well as the derivative of this variation as a function of temperature for a sample comprising 3 mg of lyophilized magnetosomes extracted from magnetotactic bacteria according to condition 3. (b) Heat flow in mW as a function of temperature produced by a sample comprising 3 mg of lyophilized magnetosomes extracted from magnetotactic bacteria according to condition 3. (c) Variation of the percentage in weight as a function of temperature as well as the derivative of this variation as a function of temperature for a sample comprising 3 mg of lyophilized SIGMA nanoparticles. (d) Heat flow in mW as a function of temperature produced by a sample comprising 3 mg of lyophilized SIGMA nanoparticles. Concerning (a) and (c), the y axis can be replaced by the percentage in mass, leading to the same plots.

FIG. 2(*a*) shows the variation of the percentage in weight of a sample comprising 3 mg of lyophilized magnetosomes (Sample 3), prepared according to condition 3 as a function of the sample temperature, when the temperature of the sample is increased from 20° C. to 600° C. at a rate of 6° C. per minute, as well as the first derivative of this percentage. These measurements have been carried out with a TGA-DSC apparatus. CHNS measurements of lyophilized magnetosomes prepared according to condition 3 have shown that they contain a percentage of carbon of 4%, before being heated, which is lower than the percentage of carbon in magnetosomes prepared according to condition 2. The percentage in weight of the sample comprising magnetosomes (Sample 3) decreases from 100% at 20° C. down to 95.1% at 600° C., indicating that sample 3 comprising magnetosomes prepared according to condition 3 loses less weight, i.e. 4.9%, than sample 2 comprising magnetosomes prepared according to condition 2. More specifically, it appears in FIG. 2(*a*) that the slope of the variation of the percentage of weight as a function of temperature is the largest within the temperature range of 200 to 400° C. Between 200 and 400° C., the variation as a function of temperature of the slope of the percentage of weight as a function of temperature displays a quadruple peak whose maximum are at 264° C., 286° C., 325, and 331° C. The two peaks at 264° C. and 325° C. can be associated to peak shoulders. This quadruple peak could be due to the loss by the nanoparticles of organic material, preferentially of type 1, for the peak centered at 264° C., of organic material, preferentially of type 3, for the peak centered at 286° C., of organic material, preferentially of type 2 for the peak centered at 325° C., and of organic material, preferentially of type 4, for the peak centered at 331° C., where this organic material likely comes from some organic material surrounding or at the surface of the mineral iron oxide core of the magnetosomes. FIG. 2(*b*) shows the heat flow in milliwatt of a sample comprising 3 mg of lyophilized magnetosomes, prepared according to condition 3 (Sample3), as a function of the sample temperature, when the temperature of the sample is increased from 20° C. to 600° C. at a rate of 6° C. per minute. These measurements have been carried out with out with a TGA-DSC apparatus. FIG. 2(*b*) shows four peaks with maximum heat flow observed at temperatures of 277° C., 335° C., 455° C. and 522° C. The peaks centered at 277° C. and 335° C. could be attributed to the combustion of the mass of nanoparticles that has been lost between 200 and 400° C. The peaks at 455 and 522° C. could be attributed to the combustion of the mass of nanoparticles that has been lost above 500° C. and/or to the oxidation of the magnetosomes from an iron oxide composition of magnetite, maghemite, or an intermediate composition between magnetite and maghemite into hematite, that could result in heat flow possibly caused by an exothermic reaction.

FIG. 2(*c*) shows the variation of the percentage in weight of a sample comprising 3 mg of powder of SIGMA nanoparticles, purchased from Merck Sigma, as a function of the sample temperature, when the temperature of the sample is increased from 20° C. to 600° C. at a rate of 6° C. per minute, as well as the first derivative of this percentage. These measurements have been carried out with a TGA-DSC apparatus. CHNS measurements of lyophilized SIGMA nanoparticles have shown that they contain a percentage of carbon of 0.3%, before being heated, which is lower than the percentage of carbon in magnetosomes prepared according to condition 3 (Sample 3). The percentage in weight of the sample comprising SIGMA nanoparticles decreases from 100% at 20° C. down to 98.7% at 600° C., indicating that the sample comprising SIGMA nanoparticles loses less mass, i.e. 1.3%, than the magnetosomes prepared according to conditions 2 and 3. More specifically, it appears in FIG. 2(*c*) that the slope of the variation of the percentage in weight of SIGMA nanoparticles as a function of temperature is the largest within the temperature range of 200 to 400° C. Between 200 and 400° C., the variation as a function of temperature of the slope of the percentage of weight of SIGMA nanoparticles as a function of temperature displays a peak whose maximum is at 296° C. This peak could be due to the loss by the nanoparticles of organic material, preferentially of type 5, where this organic material could come from organic material adsorbed at the surface or comprised in or at the surface of the SIGMA nanoparticles. FIG. 2(*d*) shows the heat flow in milliwatt of a sample comprising 3 mg of powder of SIGMA nanoparticles as a function of the sample temperature, when the temperature of the sample is increased from 20° C. to 600° C. at a rate of 6° C. per minute. These measurements have been carried out with a TGA-DSC apparatus. FIG. 2(*d*) shows two peaks with maximum heat flow observed at temperatures of 200° C., and 515° C. The peak centered at 200° C. could be attributed to the combustion of the mass of nanoparticles that has been lost between 200 and 400° C. The peak centered at 515° C. could be attributed to the combustion of the mass of nanoparticles that has been lost above 500° C. and/or to the oxidation of the magnetosomes from an iron oxide composition of magnetite, maghemite, or an intermediate composition between magnetite and maghemite into hematite, that could result in heat flow possibly caused by an exothermic reaction resulting from the oxidation.

Determination of the different types of impurities, preferentially organic material, that can be removed, released, or dissociated from the nanoparticles: Each temperature corresponding or leading to the maximum value of the derivative of the variation of the percentage in weight of magnetosomes or Sigma nanoparticles as a function of temperature could be associated to a certain type of organic material that is removed from the nanoparticles. Hence, by knowing the values of these temperatures, it is possible to compare between different samples the type of organic material that can be removed from nanoparticles.

Determination of the temperatures at which the magnetosomes were heated in the furnace: In the different samples studied (whole magnetotactic bacteria, FIG. 1(*a*), chains of magnetosomes extracted from magnetotactic bacteria, FIG. 1(*c*), extracted and heated magnetosomes, FIG. 2(*a*)), the majority of organic material is removed or released from the magnetosomes extracted from magnetotactic bacteria between 200 and 400° C., i.e. the weight variation (%) and the derivative of the variation in weight (%/° C.) are the largest within this temperature range. We have therefore chosen to heat the magnetosomes extracted from magnetotactic bacteria at different temperatures comprised between 200 and 400° C.

Determination of the lysis method that leads to the lowest quantity of carbon in the magnetosomes: The magnetosomes extracted from magnetotactic bacteria with KOH have a lower quantity of carbon than the magnetosome extracted from magnetotactic bacteria with NaOH (7.1% with KaOH, Sample 2, compared with 14% with NaOH, Sample 1). The magnetosomes extracted from magnetotactic bacteria with KOH and heated at 200° C. for 30 min, 300° C. for 1 hour, and 380° C. for 1 hour have a lower percentage of carbon than the magnetosomes extracted from magnetotactic bacteria with NaOH and heated at 200° C. for 30 min, 300° C. for 1 hour, and 380° C. for 1 hour (0.3% with KOH, Sample 8, compared with 1% with NaOH, Sample 9). The magnetosomes extracted from magnetotactic bacteria with KOH and heated at 200° C. for 1 hour, 300° C. for 2 hours, and 380° C. for 2 hours have a lower percentage of carbon than the magnetosomes extracted from magnetotactic bacteria with NaOH and heated at 200° C. for 1 hour, 300° C. for 2 hours, and 380° C. for 2 hours (0.23% with KOH, Sample 10, compared with 0.8% with NaOH). This indicates that KOH is the best lysis method to yield a low percentage of carbon in the magnetosomes and therefore to have a high level of purification.

The magnetosomes extracted from magnetotactic bacteria with NaOH and then purified by a chemical method using phenol and chloroform possess a percentage in carbon, which is larger than that of the magnetosomes extracted from magnetoatctic bacteria with NaOH and heated at 200° C. during 30 minutes, 300° C. during 1 hour and 380° C. during 1 hour (1% of carbon with sample 9 compared with 5% of carbon with sample 3).

Determination of the heating temperature that leads to the lowest quantity of carbon in the magnetosomes: Considering the magnetosomes lysed with KOH, heating them at 400° C. during 1 hour leads to a lower quantity of carbon than heating them at 200° C. during 1 hour (3% of carbon at 400° C., Sample 5, compared with 5% of carbon at 200° C., Sample 4), indicating that increasing the heating temperature enables to remove more carbon.

Determination of the number of heating steps that leads to the lowest quantity of carbon in the magnetosomes: Considering the magnetosomes lysed with KOH, heating them at two different temperatures of 200 and 300° C. (Sample 6) or three different temperatures of 200° C., 300° C., and 380° C. (Sample 8), enables to remove more carbon than heating them at only one temperature (0.65% of carbon remains in the magnetosomes when they are heated at 200° C. and 300° C., Sample 6, and 0.3% of carbon remains in the magnetosomes when they are heated at 200, 300, and 380° C., Sample 8). This suggests that in order to reach a low level of carbon in the magnetosomes, magnetosomes can be heated at more than two different temperatures comprised between 200° C. and 380° C., such as 200° C., 300° C., and 380° C.

Determination of the heating time that leads to the lowest quantity of carbon in the magnetosomes: Considering the magnetosomes lysed with KOH and heated at 200° C., 300° C., and 380° C., increasing the heating time at 200° C. from 30 min to 1 hour and increasing the heating time at 300° C. and 380° C. from 1 hour to 2 hours slightly decreases the percentage of carbon that remains in the magnetosomes after heat treatment (0.23% for Sample 10 compared with 0.3% for Sample 8).

In conclusion, we have developed a method for heating nanoparticles, called magnetosomes, which are produced by specific cells called magnetotactic bacteria, which enables to reach a very low percentage in carbon, similar to that found in chemically synthesized nanoparticles, which are not synthesized by cells.

TABLES

Table 1: Conditions of treatments for the different samples (Sample 0 to sample 11), including the condition of lysis (using NaOH, KOH, or NaOH+Phenol and chloroform), the initial temperature before heating the sample ($T_i$), the temperature $T_1$, the rate $r_{i1}$ at which the temperature is increased from $T_i$ to $T_1$, the time $t_1$ during which the temperature is maintained at $T_1$, the temperature $T_2$, the rate $r_{12}$ at which the temperature is increased from $T_1$ to $T_2$, the rate $r_{i2}$ at which the temperature is increased from $T_i$ to $T_2$, the time $t_2$ during which the temperature is maintained at $T_2$, the temperature $T_3$, the rate $r_{13}$ at which the temperature is increased from $T_1$ to $T_3$, the rate $r_{32}$ at which the temperature is increased from $T_3$ to $T_2$, the time $t_3$ during which the temperature is maintained at $t_3$, the temperature $T_4$, the rate $r_{34}$ at which the temperature is increased from $T_3$ to $T_4$, the time $t_4$ during which the temperature is maintained at $T_4$, the final temperature $T_f$, the rate $r_{1f}$ at which the temperature is decreased from $T_1$ to $T_f$, the rate $r_{2f}$ at which the temperature is decreased from $T_2$ to $T_f$, the rate $r_{3f}$ at which the temperature is decreased from $T_3$ to $T_f$, the rate $r_{4f}$ at which the temperature is decreased from $T_4$ to $T_f$.

Table 2:

For the different samples (Sample 3 to Sample 11), the percentages in mass of carbon (% C) and nitrogen (% N) after the treatment of the nanoparticles by conditions 3 to 11, the percentages in mass of carbon and (% Ci) and nitrogen (% Ni) for the magnetosomes extracted from magnetotactic bacteria following condition 1 or 2 before heat treatment (samples 4 to 11) or before treatment with phenol-chloroform (sample 3). Values of Δ% C=% Ci−% C, Δ% N=% Ni−% N, (100 Δ% C)/% Ci, 100Δ% N)/Δ% Ni.

TABLE 1

| Samples | Lysis | Treatment | $T_1$ | $T_1$, $r_{i1}$, $t_1$ | $T_2$, $r_{i2}$, $r_{i2}$, $t_2$ | $T_3$, $r_{i3}$, $r_{32}$, $t_3$ | $T_4$, $r_{34}$, $t_4$ | $T_f$, $r_{1f}$, $r_{2f}$ $r_{3f}$ $r_{4f}$ |
|---|---|---|---|---|---|---|---|---|
| Sample 0 | None | No | 20° C. | NA | NA | NA | NA | 25° C. |
| Sample 1 | NaOH | No | 20° C. | NA | NA | NA | NA | 25° C. |
| Sample 2 | KOH | No | 20° C. | NA | NA | NA | NA | 25° C. |
| Sample 3 | NaOH | Phenol-chloroform | 20° C. | NA | NA | NA | NA | 25° C. |
| Sample 4 | KOH | Heat | 20° C. | $T_1$ = 200° C.<br>$r_{i1}$ = 6° C./min<br>$t_1$ = 1 hour | NA | NA | NA | $T_i$ = 25° C.<br>$r_{1f}$ = 0.3° C./min |
| Sample 5 | KOH | Heat | 20° C. | NA | $T_2$ = 400° C.<br>$r_{12}$ = 6° C./min<br>$t_2$ = 1 hour | NA | NA | $T_i$ = 25° C.<br>$r_{2f}$ = 0.3° C./min |
| Sample 6 | KOH | Heat | 20° C. | $T_1$ = 200° C.<br>$r_{i1}$ = 9° C./min<br>$t_1$ = 30 min | NA | $T_3$ = 300° C.<br>$r_{13}$ = 10° C./min<br>$t_3$ = 1 hour | NA | $T_i$ = 25° C.<br>$r_{3f}$ = 0.4° C./min |
| Sample 7 | KOH | Heat | 20° C. | $T_1$ = 200° C.<br>$r_{i1}$ = 9° C./min<br>$t_1$ = 30 min | $T_2$ = 380° C.<br>$r_{12}$ = 8° C./min<br>$t_2$ = 1 hour | $T_3$ = 300° C.<br>$r_{32}$ = 10° C./min<br>$t_3$ = 1 hour | $T_3$ = 550° C.<br>$r_{34}$ = 8.5° C./min<br>$t_4$ = 1 hour | $T_i$ = 25° C.<br>$r_{4f}$ = 0.4° C./min |
| Sample 8 | KOH | Heat | 20° C. | $T_1$ = 200° C.<br>$r_{i1}$ = 9° C./min<br>$t_1$ = 30 min | $T_2$ = 380° C.<br>$r_{12}$ = 8° C./min<br>$t_2$ = 1 hour | $T_3$ = 300° C.<br>$r_{32}$ = 10° C./min<br>$t_3$ = 1 hour | NA | $T_i$ = 25° C.<br>$r_{3f}$ = 0.5° C./min |
| Sample 9 | NaOH | Heat | 20° C. | $T_1$ = 200° C.<br>$r_{i1}$ = 9° C./min<br>$t_1$ = 30 min | $T_2$ = 380° C.<br>$r_{12}$ = 8° C./min<br>$t_2$ = 1 hour | $T_3$ = 300° C.<br>$r_{32}$ = 10° C./min<br>$t_3$ = 1 hour | NA | $T_i$ = 25° C.<br>$r_{3f}$ = 0.5° C./min |
| Sample 10 | KOH | Heat | 20° C. | $T_1$ = 200° C.<br>$r_{i1}$ = 1.2° C./min<br>$t_1$ = 1 hour | $T_2$ = 380° C.<br>$r_{12}$ = 1° C./min<br>$t_2$ = 2 hours | $T_3$ = 300° C.<br>$r_{32}$ = 1.25° C./min<br>$t_3$ = 2 hours | NA | $T_i$ = 25° C.<br>$r_{3f}$ = 0.5° C./min |

TABLE 1-continued

| Samples | Lysis | Treatment | $T_1$ | $T_1$, $r_{i1}$, $t_1$ | $T_2$, $r_{i2}$, $r_{i2}$, $t_2$ | $T_3$, $r_{i3}$, $r_{32}$, $t_3$ | $T_4$, $r_{34}$, $t_4$ | $T_f$, $r_{1f}$, $r_{2f}$ $r_{3f}$ $r_{4f}$ |
|---|---|---|---|---|---|---|---|---|
| Sample 11 | NaOH | Heat | 20° C. | $T_1$ = 200° C.<br>$r_{i1}$ = 1.2° C./min<br>$t_1$ = 1 hour | $T_2$ = 380° C.<br>$r_{12}$ = 81° C./min<br>$t_2$ = 2 hours | $T_3$ = 300° C.<br>$r_{32}$ = 1.25° C./min<br>$t_3$ = 2 hours | NA | $T_i$ = 25° C.<br>$r_{3f}$ = 0.5° C./min |

$R_i$: rate of temperature increase to reach $T_i$ $T_i$: temperature maintained during step i NA: Not applicable.

TABLE 2

| Samples | Lysis | Treat-ment | % C | % N | % $C_i$ | % $N_i$ | Δ % C = % $C_i$-% C | Δ % N = % $N_i$-% N | $\frac{100*\Delta\ \%\ C}{\%\ C_i}$ | $\frac{100*\Delta\ \%\ N}{\%\ N_i}$ |
|---|---|---|---|---|---|---|---|---|---|---|
| Sample 0 | None | No | 44 ± 4 | 9.9 ± 0.7 | | | | | | |
| Sample 1 | NaOH | No | 14 ± 6 | 2.5 ± 0.9 | 44 ± 4 | 9.9 ± 0.7 | −30 ± 10 | −7 ± 2 | −68 ± 17 | −75 ± 15 |
| Sample 2 | KOH | No | 7.1 ± 0.7 | 0.8 ± 0.2 | 44 ± 4 | 9.9 ± 0.7 | −37 ± 5 | −9.1 ± 0.9 | −84 ± 4 | −92 ± 3 |
| Sample 3 | NaOH | Phenol-chloro-form | 5 ± 2 | 0.3 ± 0.2 | 14 ± 6 | 2.5 ± 0.9 | −9 ± 8 | −2 ± 1 | −64 ± 30 | −88 ± 8 |
| Sample 4 | KOH | Heat | 5 ± 1 | 0.28 ± 0.08 | 7.1 ± 0.7 | 0.8 ± 0.2 | −2 ± 2 | −0.5 ± 0.2 | −30 ± 25 | −65 ± 9 |
| Sample 5 | KOH | Heat | 3 ± 1 | 0.2 ± 0.1 | 7.1 ± 0.7 | 0.8 ± 0.2 | −4 ± 2 | −0.6 ± 0.3 | −58 ± 22 | −75 ± 19 |
| Sample 6 | KOH | Heat | 0.65 ± 0.01 | 0.099 ± 0.001 | 7.1 ± 0.7 | 0.8 ± 0.2 | −6.5 ± 0.7 | −0.7 ± 0.2 | −91 ± 1 | −88 ± 3 |
| Sample 7 | KOH | Heat | 0.3 ± 0.1 | 0.03 ± 0.01 | 7.1 ± 0.7 | 0.8 ± 0.2 | −6.8 ± 0.8 | −0.8 ± 0.2 | −96 ± 2 | −96 ± 1 |
| Sample 8 | KOH | Heat | 0.3 ± 0.1 | 0.03 ± 0.01 | 7.1 ± 0.7 | 0.8 ± 0.2 | −6.8 ± 0.8 | −0.8 ± 0.2 | −96 ± 2 | −96 ± 1 |
| Sample 9 | NaOH | Heat | 1.0 ± 0.3 | 0.4 ± 0.1 | 14 ± 6 | 2.5 ± 0.9 | −13 ± 1 | −2 ± 1 | −93 ± 33 | −84 ± 10 |
| Sample 10 | KOH | Heat | 0.23 ± 0.07 | 0.01 ± 0.01 | 7.1 ± 0.7 | 0.8 ± 0.2 | −6.9 ± 0.7 | −0.8 ± 0.2 | −96.8 ± 0.3 | −98.8 ± 0.3 |
| Sample 11 | NaOH | Heat | 0.8 ± 0.2 | 0.25 ± 0.03 | 14 ± 6 | 2.5 ± 0.9 | −13 ± 1 | −2.3 ± 0.9 | −94 ± 33 | −90 ± 4 |

The invention claimed is:

1. A method for removing at least one impurity from at least one metal-based nanoparticle, comprising at least two heating steps:

heating step 1 during which the at least one nanoparticle is heated to a heating temperature that is between 50° C. and 500° C. and remains or is maintained at the heating temperature that is between 50° C. and 500° C. for a heating time that is between 1 second and 1 month, and heating step 2 during which the at least one nanoparticle is heated to a heating temperature that is between 350° C. and 500° C. and remains or is maintained at the heating temperature that is between 350° C. and 500° C. for a heating time that is between 1 second and 1 month wherein each of the heating step 1 and the heating step 2 comprises at least two phases:

(i) a second phase of each of the heating step 1 and heating step 2 during which the temperature of the at least one nanoparticle remains or is maintained at the heating temperature, which is:

a) between 50° C. and 500° C. for heating step 1, and b) between 350° C. and 500° C. for the heating step 2, and (ii) at least one other phase selected from the groups consisting of:

a first phase during which the temperature of the at least one nanoparticle increases or is increased from an initial temperature to the heating temperature of the second phase, wherein the initial temperature is smaller than $10^{2}$° C. or smaller than the heating temperature of the second phase, and a third phase during which the temperature of the at least one nanoparticle decreases or is decreased from the heating temperature of the second phase to a final temperature, wherein the at least one nanoparticle has a crystalline structure, and the heating temperature of the second phase and the final temperature reached by the at least one nanoparticle of the third phase do not induce melting of the at least one nanoparticle, destruction of the at least one nanoparticle, denaturation of the at least one nanoparticle, or a modification of the crystalline structure of the at least one nanoparticle that is different from that resulting from oxidation or that differs from a change in an oxidation state of the at least one nanoparticle, wherein the at least one nanoparticle has at least one property selected from the group consisting of magnetic, diamagnetic, ferromagnetic, ferrimagnetic, and paramagnetic, and wherein the at least one impurity is removed from the at least one nanoparticle by the method.

2. The method according to claim 1, wherein the temperature of the at least one nanoparticle is increased during at least one of the heating step 1 and the heating step 2 at a rate that is between $10^{-5}$ and $10^{5}$° C./min.

3. The method according to claim 1, wherein the heating time for the second phase in each of the heating step 1 and the heating step 2, $t_i$ in minutes, is proportional to a quantity of heated nanoparticles, $Q_{nano}$ in milligrams, which is a property that is mathematically expressed as: $t_i = \alpha{:}Q_{nano}$, where α is a proportionality coefficient that is between $10^{-5}$ and $10^{5}$.

4. The method according to claim 1, wherein the duration of at least one phase is decreased by reducing the percentage of humidity of the at least one nanoparticle.

5. The method according to claim 1, wherein the at least one impurity consists of or comprises or originates from carbon or carbonaceous material, and the at least one nanoparticle has a percentage in mass of carbonaceous material or carbon that is lower than 90% after the at least one of the heating step 1 and the heating step 2.

6. The method according to claim 1, wherein the at least one impurity consists of or comprises or originates from carbon or carbonaceous material, and more than 10% in mass of carbon or carbonaceous material is removed from the at least one nanoparticle, said more than 10% in mass is equal to $|(\% C_{AT} - \% C_{BT})/\% C_{BT}|$, where $\% C_{AT}$ and $\% C_{BT}$ are the percentages of carbon or carbonaceous material after and before treating the at least one nanoparticle with the method.

7. The method according to claim 1, wherein at least one of the at least two heating steps is carried out in the presence of oxygen.

8. The method according to claim 1, wherein the at least one impurity is removed from the at least one nanoparticle, and the at least one impurity is located at a depth of less than 100 nm inside the at least one nanoparticle.

9. The method according to claim 1, wherein the at least one impurity consists of or comprises or originates from carbon or carbonaceous material.

10. The method according to claim 1, wherein the at least one impurity consists of or comprises or originates from a cell synthesizing the at least one nanoparticle.

11. The method according to claim 1, wherein the at least one impurity consists of carbonaceous material and the method removes the carbonaceous material from the at least one nanoparticle.

12. The method according to claim 1, wherein the at least one nanoparticle comprises a core and a coating, and the least one impurity is removed from the coating of the at least one nanoparticle.

13. The method according to claim 1, wherein the method is carried out in the presence of a carrying gas or $CO_2$.

14. The method according to claim 13, wherein the carrying gas or $CO_2$ removes the at least one impurity from the at least one nanoparticle.

* * * * *